(12) United States Patent
Yamada et al.

(10) Patent No.: US 12,193,323 B2
(45) Date of Patent: Jan. 7, 2025

(54) ORGANIC COMPOUND AND ORGANIC LIGHT-EMITTING DEVICE

(71) Applicant: CANON KABUSHIKI KAISHA, Tokyo (JP)

(72) Inventors: Naoki Yamada, Tokyo (JP); Jun Kamatani, Tokyo (JP); Yosuke Nishide, Kanagawa (JP); Hirokazu Miyashita, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 558 days.

(21) Appl. No.: 17/512,435

(22) Filed: Oct. 27, 2021

(65) Prior Publication Data
US 2022/0140249 A1     May 5, 2022

(30) Foreign Application Priority Data
Nov. 2, 2020 (JP) .................. 2020-183751

(51) Int. Cl.
*H10K 85/60* (2023.01)
*C07D 311/96* (2006.01)
(Continued)

(52) U.S. Cl.
CPC ......... *H10K 85/636* (2023.02); *C07D 311/96* (2013.01); *C07D 335/04* (2013.01);
(Continued)

(58) Field of Classification Search
CPC ............... H10K 85/636; H10K 85/633; H10K 85/6572; H10K 85/6574; H10K 50/11;
(Continued)

(56) References Cited

U.S. PATENT DOCUMENTS

2004/0076853 A1\*   4/2004  Jarikov .................. C09K 11/06
                                                              428/917

FOREIGN PATENT DOCUMENTS

JP    2017515817 A    6/2017
JP    2018503619 A    2/2018
(Continued)

OTHER PUBLICATIONS

Jesuraj, P. Justin, et al. "Intramolecular charge transfer-based spirobifluorene-coupled heteroaromatic moieties as efficient hole transport layer and host in phosphorescent organic light-emitting diodes." Organic Electronics 85 (2020): 105825. (Year: 2020).\*
(Continued)

*Primary Examiner* — Dawn L Garrett
(74) *Attorney, Agent, or Firm* — Canon U.S.A., Inc. I.P. Division

(57) ABSTRACT

An organic compound represented by formula [1] or [2]:

(Continued)

-continued

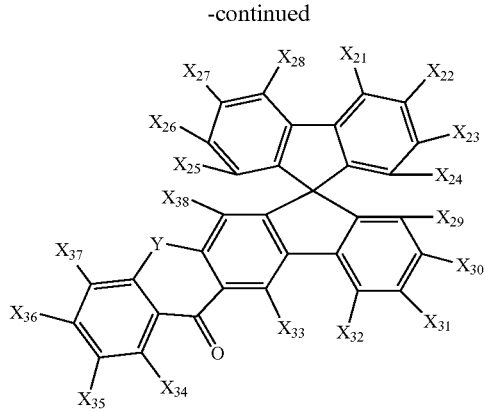

[2]

where $X_1$ to $X_{18}$ and $X_{21}$ to $X_{38}$ are each independently selected from a hydrogen atom, a halogen atom, an alkyl group, an alkoxy group, an amino group, an aryl group, a heterocyclic group, an aryloxy group, a heteroaryloxy group, a silyl group, and a cyano group, in which at least one of $X_1$ to $X_8$ and at least one of $X_{21}$ to $X_{28}$ are substituted or unsubstituted amino groups; and each Y is oxygen, sulfur, selenium, tellurium, or a $CR_1CR_2$ group and may be the same or different, in which $R_1$ and $R_2$ are each independently selected from a hydrogen atom, an alkyl group, an alkoxy group, an amino group, an aryl group, a heterocyclic group, an aryloxy group, a heteroaryloxy group, a silyl group, or a cyano group.

17 Claims, 8 Drawing Sheets

(51) Int. Cl.
C07D 335/04 (2006.01)
C07D 405/04 (2006.01)
C07D 409/12 (2006.01)
C09K 11/06 (2006.01)
H10K 50/11 (2023.01)
H10K 101/10 (2023.01)

(52) U.S. Cl.
CPC ......... *C07D 405/04* (2013.01); *C07D 409/12* (2013.01); *C09K 11/06* (2013.01); *H10K 85/633* (2023.02); *H10K 85/6572* (2023.02); *H10K 85/6574* (2023.02); *C09K 2211/1018* (2013.01); *H10K 50/11* (2023.02); *H10K 85/615* (2023.02); *H10K 85/6576* (2023.02); *H10K 2101/10* (2023.02)

(58) Field of Classification Search
CPC ............. H10K 85/615; H10K 85/6576; H10K 2101/10; H10K 50/121; H10K 85/624; C07D 311/96; C07D 335/04; C07D 405/04; C07D 409/12; C07D 11/06; C09K 2211/1018
See application file for complete search history.

(56) References Cited

FOREIGN PATENT DOCUMENTS

| JP | 2018511572 A | 4/2018 | |
| WO | 2009139580 A1 | 11/2009 | |
| WO | WO-2014071836 A1 * | 5/2014 | ........... C07D 335/10 |
| WO | WO-2016116522 A1 * | 7/2016 | ............. C09K 11/06 |
| WO | 2017092476 A1 | 6/2017 | |

OTHER PUBLICATIONS

Qu, Yang-Kun, et al. "Spiro compounds for organic light-emitting diodes." Accounts of Materials Research 2.12 (2021): 1261-1271. (Year: 2021).*

* cited by examiner

| No. | COMPOUND | HOMO DISTRIBUTION | LUMO DISTRIBUTION | S1-T1 DIFFERENCE (eV) | S1 (nm) |
|---|---|---|---|---|---|
| B-1 |  |  |  | 0.01 | 475 |
| B-2 |  |  |  | 0.13 | 444 |
| B-3 |  |  |  | 0.01 | 485 |
| b-1 |  |  |  | 0.64 | 362 |
| b-2 |  |  |  | 0.65 | 351 |
| b-3 |  |  |  | 0.37 | 453 |
| b-4 |  |  |  | 0.75 | 364 |
| b-5 |  |  |  | 0.004 | 665 |

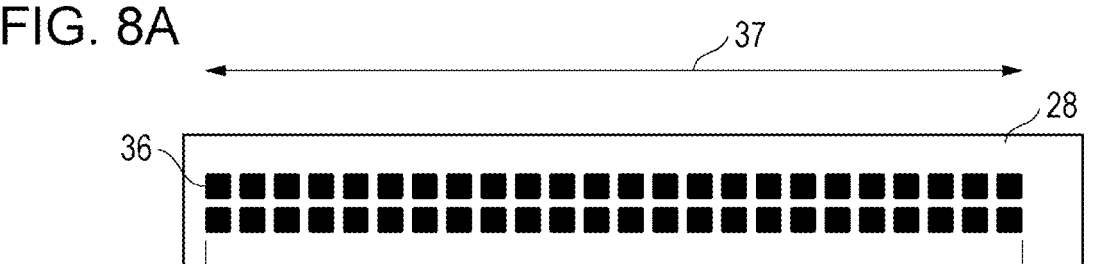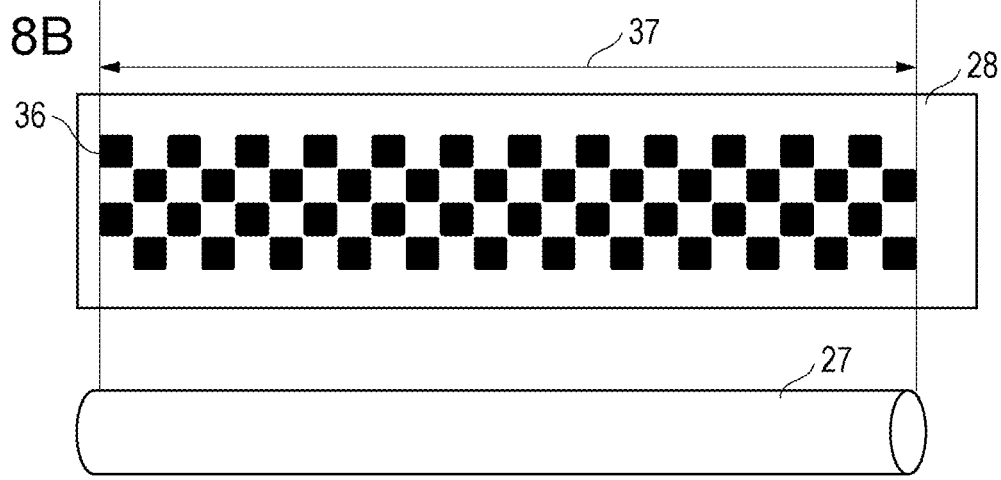

ORGANIC COMPOUND AND ORGANIC LIGHT-EMITTING DEVICE

BACKGROUND OF THE INVENTION

Field of the Invention

The present disclosure relates to an organic compound and an organic light-emitting device containing the organic compound.

Description of the Related Art

Organic light-emitting devices (hereinafter, also referred to as "organic electroluminescent devices" or "organic EL devices") are electronic devices each including a pair of electrodes and an organic compound layer disposed between these electrodes. The injection of electrons and holes from these pairs of electrodes generates excitons in the light-emitting organic compound in the organic compound layer, and when the excitons return to the ground state, the organic light-emitting device emits light.

Recently, organic light-emitting devices have made remarkable progress and have achieved low-driving voltage, various emission wavelengths, and fast response time. The use thereof has enabled the development of thinner and lighter light-emitting apparatuses.

Examples of high-efficiency light-emitting devices include devices containing high-efficiency materials, such as phosphorescent materials and delayed fluorescent materials.

International Publication No. 2017/092476 discloses compound A-1 below. International Publication No. 2009/139580 discloses compound A-2 below.

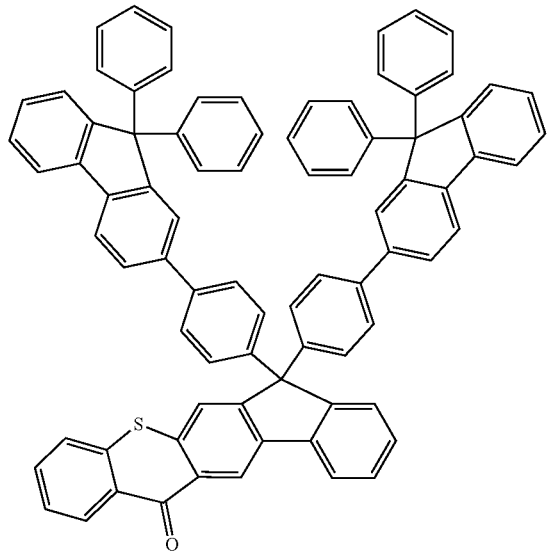

A-1

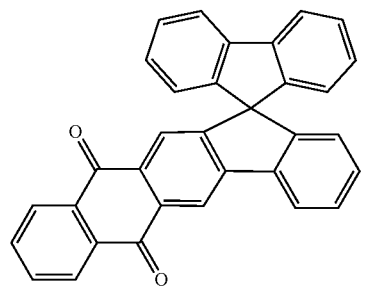

A-2

When compounds A-1 and A-2 described in International Publication Nos. 2017/092476 and 2009/139580 are used for light-emitting layers of organic light-emitting devices, there is a disadvantage with luminous efficiency.

SUMMARY OF THE INVENTION

The present disclosure has been accomplished to solve the above-mentioned disadvantage and provides an organic compound and an organic light-emitting device that have excellent luminous efficiency. The present disclosure also provides an organic light-emitting device excellent in luminous efficiency and driving durability characteristics.

According to one aspect of the present disclosure, there is provided an organic compound represented by formula [1] or [2]:

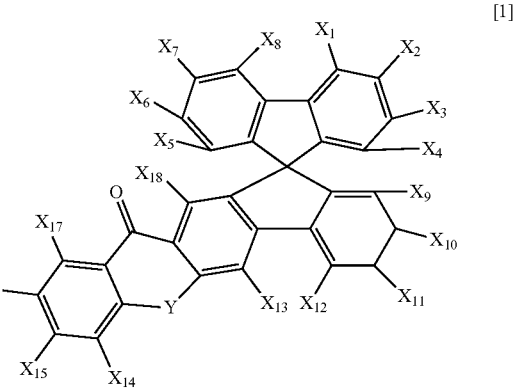

[1]

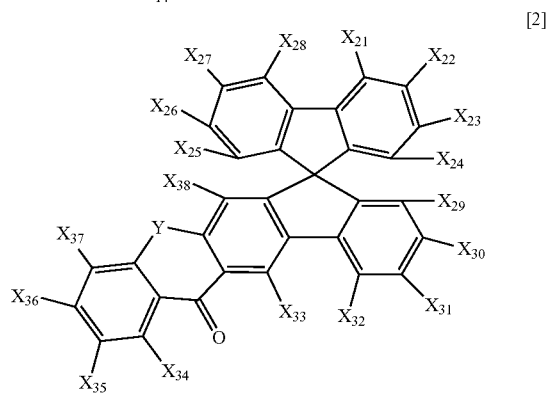

[2]

where in formula [1] or [2], $X_1$ to $X_{18}$ and $X_{21}$ to $X_{38}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a substituted or unsubstituted heteroaryloxy group, a silyl group, and a cyano group, in which at least one of $X_1$ to $X_8$ and at least one of $X_{21}$ to $X_{28}$ are substituted or unsubstituted amino groups, groups bonded to nitrogen atoms of the substituted or unsubstituted amino groups are optionally taken together to form a ring structure, the groups bonded to the nitrogen atoms of the substituted or unsubstituted amino groups are each optionally taken together with any of adjacent $X_1$ to $X_8$ or any of adjacent $X_{21}$ to $X_{28}$ to form a ring, and the groups bonded to the nitrogen atoms of the substituted or unsubstituted amino groups are each optionally taken together with any of adjacent $X_1$ to $X_8$ or any of adjacent $X_{21}$ to $X_{28}$ with oxygen or sulfur provided therebetween to form a ring; and each Y is oxygen, sulfur, selenium, tellurium, or a $CR_1CR_2$ group and may be the same or different, in which $R_1$ and $R_2$ are each independently selected from a hydrogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a substituted or unsubstituted heteroaryloxy group, a silyl group, and a cyano group.

Further features of the present disclosure will become apparent from the following description of exemplary embodiments with reference to the attached drawings.

BRIEF DESCRIPTION OF THE DRAWINGS

FIGS. 8A and 8B are schematic views of examples of an exposure light source for an image-forming apparatus according to an embodiment of the present disclosure.

DESCRIPTION OF THE EMBODIMENTS

Organic Compound

Figure 1:
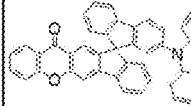
FIG. 1 is a table presenting molecular models of HOMO distributions and LUMO distributions of exemplified compounds and the S1–T1 differences of the exemplified compounds.
Figure 1:
Figure 1:
Figure 1:
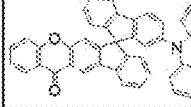
Figure 1:
Figure 1:
Figure 1:
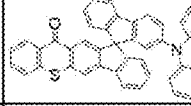
Figure 1:
Figure 1:
Figure 1:
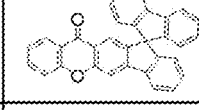
Figure 1:
Figure 1:
Figure 1:
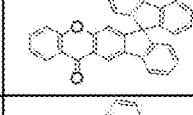
Figure 1:
Figure 1:
Figure 1:
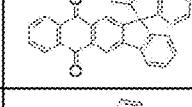
Figure 1:
Figure 1:
Figure 1:
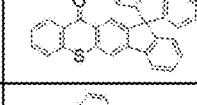
Figure 1:
Figure 1:
Figure 1:
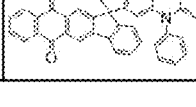
Figure 1:
Figure 1:

An organic compound according to an embodiment will be described. The organic compound according to this embodiment is represented by formula [1] or [2].

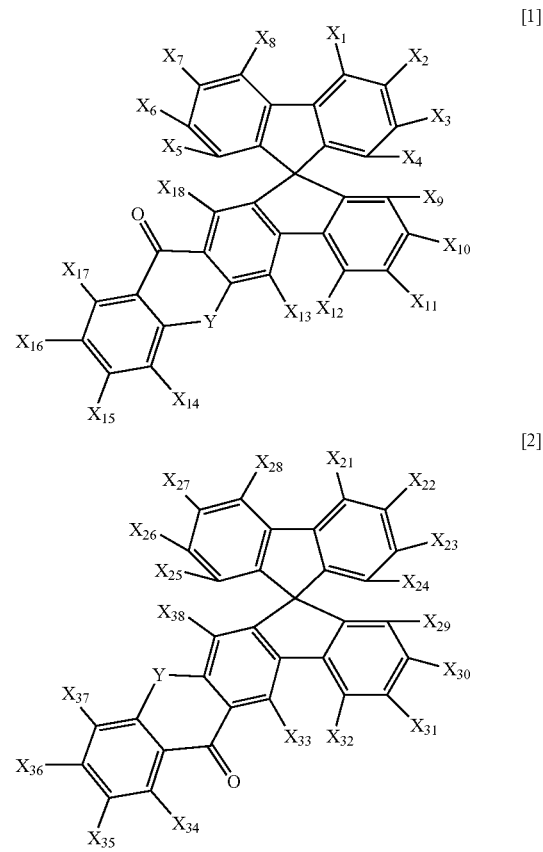

$X_1$ to $X_{18}$ and $X_{21}$ to $X_{38}$ $X_1$ to $X_{18}$ and $X_{21}$ to $X_{38}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a substituted or unsubstituted heteroaryloxy group, a silyl group, and a cyano group. At least one of $X_1$ to $X_8$ and at least one of $X_{21}$ to $X_{28}$ are each a substituted or unsubstituted amino group. Groups bonded to nitrogen atoms of the substituted or unsubstituted amino groups may be taken together to form a ring structure. The groups bonded to the nitrogen atoms of the substituted or unsubstituted amino groups may each be taken together with any of adjacent $X_1$ to $X_8$ or any of adjacent $X_{21}$ to $X_{28}$ to form a ring. The groups bonded to the nitrogen atoms of the substituted or unsubstituted amino groups may each be taken together with any of adjacent $X_1$ to $X_8$ or any of adjacent $X_{21}$ to $X_{28}$ with oxygen or sulfur provided therebetween to form a ring.

Non-limiting examples of the halogen atom include fluorine, chlorine, bromine, and iodine.

Non-limiting examples of the alkyl group include a methyl group, an ethyl group, a n-propyl group, an isopropyl group, a n-butyl group, a tert-butyl group, a sec-butyl group, an octyl group, a cyclohexyl group, a 1-adamantyl group, and a 2-adamantyl group. As the alkyl group, an alkyl group having 1 to 10 carbon atoms can be used.

Non-limiting examples of the alkoxy group include a methoxy group, an ethoxy group, a propoxy group, a 2-ethyloctyloxy group, and a benzyloxy group. As the alkoxy group, an alkoxy group having 1 to 10 carbon atoms can be used.

Non-limiting examples of the amino group include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, ab N-mesityl-N-phenylamino group, an N,N-dimesitylamino group, an N-phenyl-N-(4-tert-butylphenyl)amino group, an N-phenyl-N-(4-trifluoromethylphenyl)amino group, an N-piperidyl group, a carbazolyl group, and an acridyl group.

Non-limiting examples of the aryl group include a phenyl group, a naphthyl group, an indenyl group, a biphenyl group, a terphenyl group, a fluorenyl group, a phenanthryl group, a triphenylenyl group, a pyrenyl group, an anthracenyl group, a perylenyl group, a chrysenyl group, and a fluoranthenyl group. As the aryl group, an aromatic hydrocarbon group having 6 to 60 carbon atoms can be used.

Non-limiting examples of the heterocyclic group include a pyridyl group, a pyrimidyl group, a pyrazyl group, a triazinyl group, a benzofuranyl group, a benzothiophenyl group, a dibenzofuranyl group, a dibenzothiophenyl group, an oxazolyl group, an oxadiazolyl group, a thiazolyl group, a thiadiazolyl group, a carbazolyl group, an acridinyl group, and a phenanthrolinyl group. As the heterocyclic group, a heterocyclic group having 3 to 60 carbon atoms can be used.

Non-limiting examples of the aryloxy group include a phenoxy group and a naphthoxy group.

Non-limiting examples of the heteroaryloxy group include a furanyloxy group and a thienyloxy group.

Non-limiting examples of the silyl group include a trimethylsilyl group and a triphenylsilyl group.

Non-limiting examples of substituents that may be further contained in the alkyl group, the alkoxy group, the amino group, the aryl group, the heterocyclic group, the aryloxy group, and the heteroaryloxy group include alkyl groups, such as a methyl group, an ethyl group, a n-propyl group, an isopropyl group, a n-butyl group, and a tert-butyl group; aralkyl groups, such as a benzyl group; aryl groups, such as a phenyl group and a biphenyl group; heterocyclic groups, such as a pyridyl group and a pyrrolyl group; amino groups, such as a dimethylamino group, a diethylamino group, a dibenzylamino group, a diphenylamino group, and a ditolylamino group; alkoxy group, such as a methoxy group, an ethoxy group, and a propoxy group; aryloxy groups, such as a phenoxy group; halogen atoms, such as fluorine, chlorine, bromine, and iodine atoms; and a cyano group.

At least one of $X_2$, $X_3$, $X_6$, and $X_7$ and at least one of $X_{22}$, $X_{23}$, $X_{26}$, and $X_{27}$ can each be a substituted or unsubstituted amino group. At least one of $X_1$, $X_4$, $X_5$, and $X_8$ and at least one of $X_{21}$, $X_{24}$, $X_{25}$, and $X_{28}$ can each be a substituted or unsubstituted amino group.

Y

Each Y is oxygen, sulfur, selenium, tellurium, or a $CR_1CR_2$ group and may be the same or different. Each Y can be oxygen.

$R_1$ and $R_2$ are each independently selected from a hydrogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryl group, a silyl group, and a cyano group.

Specific examples of the alkyl group, the alkoxy group, the amino group, the aromatic hydrocarbon group, the heterocyclic group, the aryloxy group, the heteroaryloxy group, and the silyl group that are represented by $R_1$ and $R_2$ are, but not limited to, the same as those described for $X_1$ to $X_{18}$ and $X_{21}$ to $X_{38}$. As the alkyl group, an alkyl group having 1 to 10 carbon atoms can be used. As the alkoxy group, an alkoxy group having 1 to 10 carbon atoms can be used. As the aromatic hydrocarbon group having 6 to 60 carbon atoms can be used. As the heterocyclic group, a heterocyclic group having 3 to 60 carbon atoms can be used. Specific examples of substituents that may further be contained in the alkyl group, the alkoxy group, the amino group, the aromatic hydrocarbon group, the heterocyclic group, the aryloxy group, and the heteroaryloxy group are, but not limited to, the same as those described for $X_1$ to $X_{18}$ and $X_{21}$ to $X_{38}$.

A method for synthesizing an organic compound according to this embodiment of the present disclosure will be described below. The organic compound according to the embodiment of the present disclosure is synthesized, for example, by a reaction scheme described below.

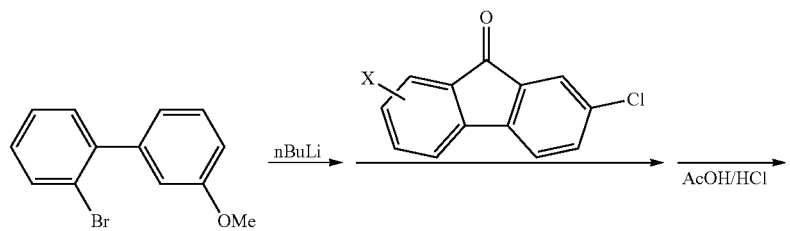

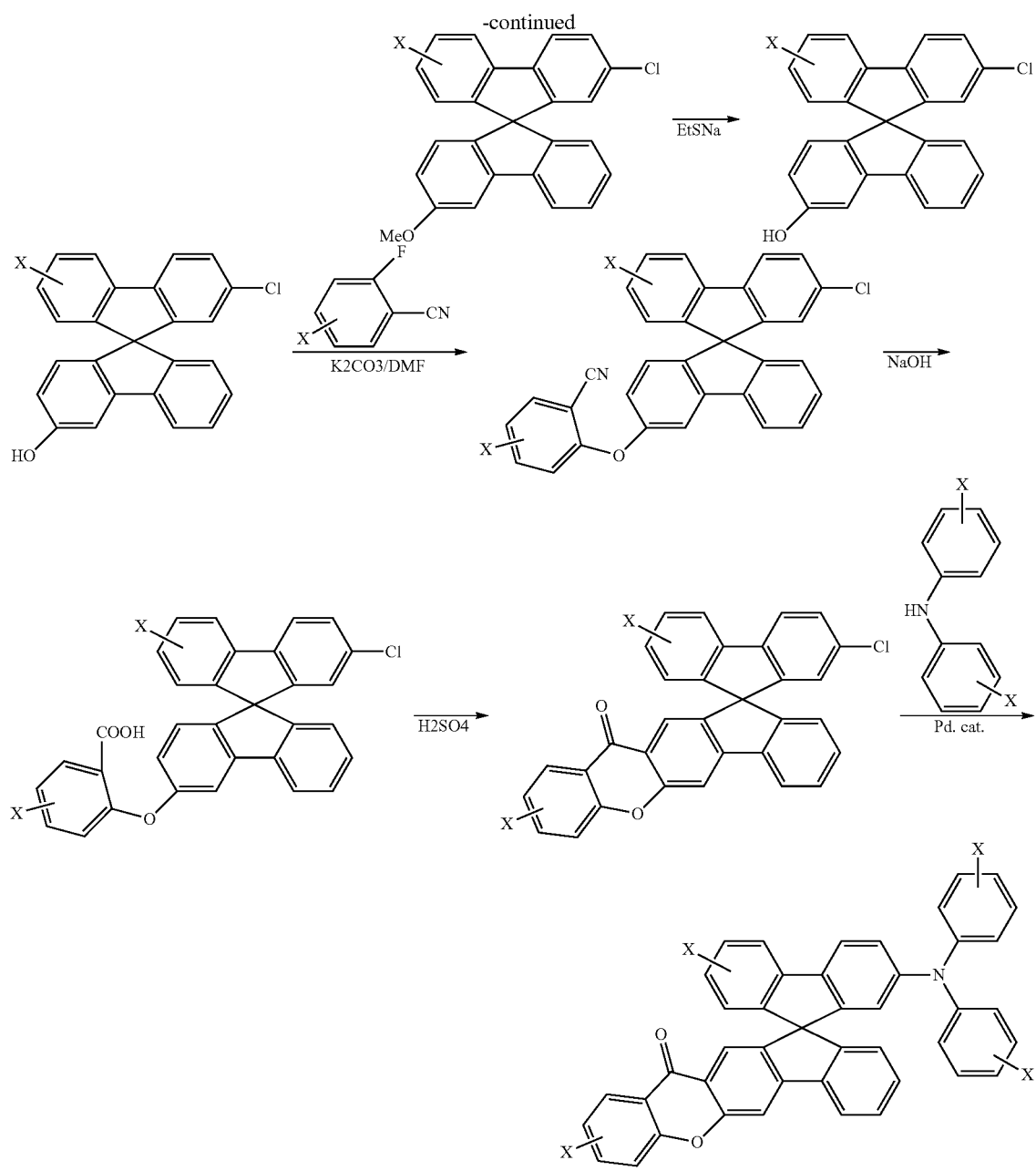

Here, each of the compounds represented by formulae [1] and [2] can be synthesized by appropriately changing the substituent X and appropriately changing Y into oxygen, sulfur, selenium, tellurium, or a $CR_1CR_2$ group. The synthesis method is not limited to the above.

The organic compound according to the embodiment has the following features. Thus, the use of the organic compound in an organic light-emitting device provides an organic light-emitting device having high luminous efficiency and excellent driving durability characteristics. A basic skeleton in this embodiment is a skeleton in which in the compound represented by formula [1] or [2], $X_1$ to $X_{18}$ and $X_{21}$ to $X_{38}$ are each a hydrogen atom, and when Y is a $CR_1CR_2$ group, $R_1$ and $R_2$ are each a hydrogen atom.

(1) The spirofluorene contains an electron-withdrawing carbonyl group on one fluorene ring and an electron-donating amino group on the other fluorene ring, thus resulting in a small energy gap between S1 and T1.

(2) The use of an electron-donating group as Y results in the molecule having a wider band gap more suitable for a light-emitting layer.

(3) The presence of the spiro structure is less likely to lead to molecular association.

(4) The presence of the spiro structure is less likely to lead to cleavage of a bond in the quaternary carbon moiety.

These features will be described below.

(1) The spirofluorene contains an electron-withdrawing carbonyl group on one fluorene ring and an electron-donating amino group on the other fluorene ring, thus resulting in a small energy gap between S1 and T1.

In the compound according to the embodiment, a moiety occupying the electron orbital distribution of the lowest unoccupied molecular orbital (LUMO) and a moiety occupying the electron orbital distribution of the highest occupied molecular orbital (HOMO) are separated by the spiro moiety of the spirofluorene, as B-1 to B-3 illustrated in FIG. 1. It can be seen that a portion occupying both the HOMO and LUMO is small. This leads to a small overlap integral and a small difference between the excited singlet state (S1) and the excited triplet state (T1).

The above feature is the effect due to the presence of an electron-withdrawing carbonyl group in one fluorene ring of the spirofluorene and an electron-donating amino group in the other fluorene ring. For amino group-free structures, such as b-1 to b-4, it can be seen that the moiety occupying the electron orbital distribution of the LUMO and the moiety occupying the electron orbital distribution of the HOMO are not separated by the spiro moiety of spirofluorene. B-1, B-2, and B-3 are exemplary compounds C-1, D-1, and E-1, respectively, described below. In addition, b-3 and b-4 are compound A-2 (comparative compound J-2 described below) described in International Publication No. 2009/139580 and comparative compound J-1, respectively.

The above calculation results were visualized using molecular orbital calculations. As the molecular orbital calculation method, the density functional theory (DFT), which is widely used at present, was used with the B3LYP functional and 6-31G* as the basis function.

The molecular orbital calculation method was performed using Gaussian 09 (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010), which is widely used at present.

As described above, compounds B-1 to B-3 according to the embodiment are characterized in that the difference between S1 and T1 is small. When the compound according to the embodiment is used in the light-emitting layer of an organic light-emitting device, the device having high luminous efficiency is provided. The reason for this is as follows: For excitons consisting of singlet and triplet excitons in a ratio of 1:3, the triplet excitons, which undergo thermal deactivation normally, can be used for delayed fluorescence from the excited singlet state due to the small difference between S1 and T1. To convert the triplet excitons into the excited singlet state, a smaller difference between S1 and T1 is advantageous because of a smaller energy barrier. The compound according to the embodiment is advantageous for that condition. Thus, the device having high luminous efficiency is provided.

Comparative compounds b-1 to b-4 contain no amino group as a substituent. Thus, the large difference between S1 and T1 results in a large energy barrier, resulting in a disadvantage for delayed fluorescence.

(2) The use of an electron-donating group as Y results in the molecule having a wider band gap more suitable for a light-emitting layer.

When Y is a carbonyl group, which is an electron-withdrawing group, in the compound according to the embodiment, the basic skeleton contains two carbonyl groups. This results in excessively strong electron-withdrawing property, thus leading to a narrow band gap of the molecule. The emission wavelength is longer than that required for the light-emitting device. Specifically, b-5 in FIG. 1 is a compound in which Y is a carbonyl group, which is an electron-withdrawing group. The value of S1 is 665 nm, indicating that the absorption wavelength of the compound is already longer than the red light-emitting region. In contrast, when Y is an oxygen, sulfur, selenium, tellurium, or $CR_1CR_2$ group, as in the compound according to the embodiment, Y has the electron-donating property. Thus, the value of S1 is in the range of 444 nm to 485 nm. This indicates that the value is suitable for emission in the visible region, i.e., blue, green, and red light emission. In other words, the compound has a band gap suitable for a light-emitting layer that emits light in the visible light region.

(3) The presence of the spiro structure is less likely to lead to molecular association.

The compound according to the embodiment has a spiro structure and thus is less likely to undergo molecular association. The two fluorene rings are almost orthogonal to each other with respect to the spiro structure, thus resulting in a low degree of flatness of the molecule. The spiro structure is at the molecular center where the HOMO and LUMO are separated. Thus, the molecules are less likely to stack together and are less likely to undergo molecular association. In contrast, in the case of spiro structure-free compound b-4 as illustrated in FIG. 1, the two phenyl groups attached to the fluorene ring can rotate freely, resulting in a high degree of flatness. Thus, molecular association occurs easily. In the case of a molecule having a spiro structure and containing a moiety that is not involved in the HOMO or LUMO, or in the case of a molecule having a spiro structure at the end thereof, it is difficult to avoid molecular stacking.

The above feature provides the following effects: in the case where the compound according to the embodiment is used in the organic layer of an organic light-emitting device, a stable amorphous film that is less likely to crystallize is provided, and the organic light-emitting device has high durability without the occurrence of crystallization even in the case of long-term operation.

In addition, in the case where the compound according to the embodiment is used in the light-emitting layer of an organic light-emitting device, molecular association is less likely to occur, and thus concentration quenching is less likely to occur. Accordingly, the organic light-emitting device has high luminous efficiency.

The above effect also improves sublimability. The improvement of sublimability enables the purification of the material by sublimation and the production of an organic light-emitting device by vapor deposition. This can reduce the amount of impurities contained in the organic light-emitting device and can inhibit deteriorations in luminous efficiency and driving durability due to impurities.

(4) The presence of the spiro structure is less likely to lead to cleavage of a bond in the quaternary carbon moiety.

In the compound according to the embodiment, the quaternary carbon surrounded by a dotted line in the chemical formula below has a spiro structure. Even if the molecule is cleaved, the cleaved phenyl group is bonded to the structure of the main body and thus easily returns to its original structure. In the case of a non-spiro structure, such as compound A-1 described in International Publication No. 2017/092476, when the molecule is cleaved, the structure does not easily return to its original structure because the cleaved phenyl group is not bonded to the structure of the main body. The compound is easily cleavage and structural changes, thus deteriorating the device durability.
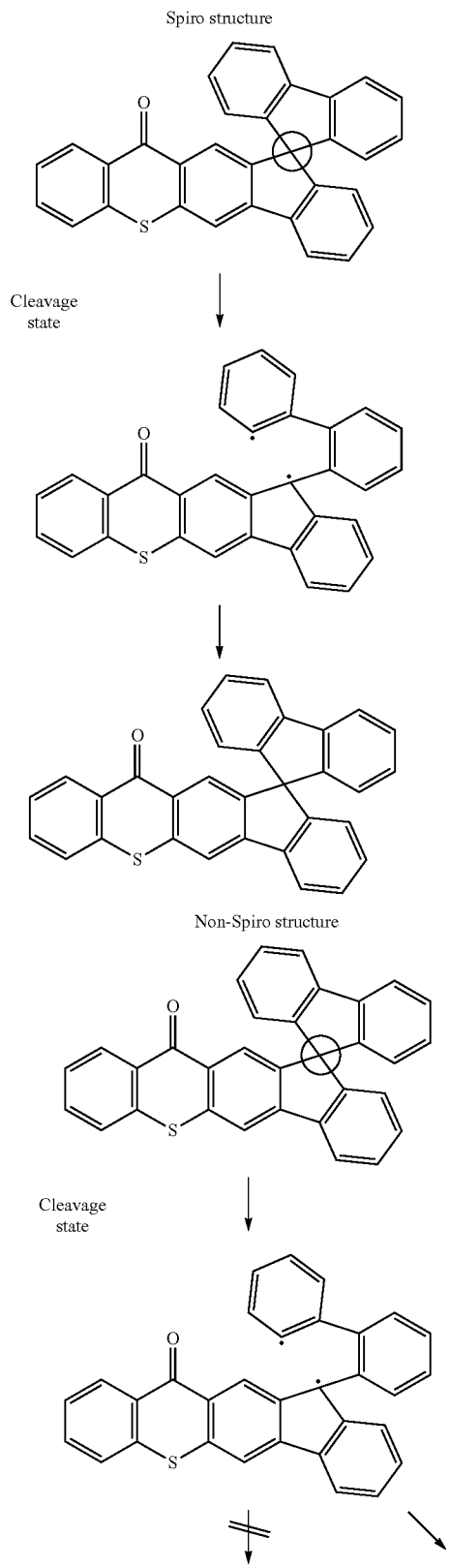

-continued

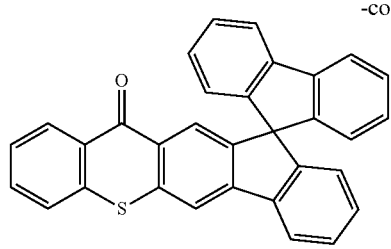
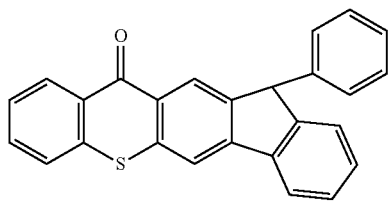

In addition, the compound according to the embodiment can have the following features (5) and (6) with respect to the position of the amino group.

(5) When at least one of $X_2$, $X_3$, $X_6$, and $X_7$ and at least one of $X_{22}$, $X_{23}$, $X_{26}$, and $X_{27}$ are each an amino group, the energy gap between S1 and T1 can be further reduced.

In this case, as presented in Table 1, a device having higher luminous efficiency is provided. When at least one of $X_2$, $X_3$, $X_6$, and $X_7$ and at least one of $X_{22}$, $X_{23}$, $X_{26}$, and $X_{27}$ are each an amino group, the energy gap between S1 and T1 can be further reduced. In this case, the device can have higher efficiency. B-2 and B-4 are exemplary compound D-1 and D-5, respectively, as described below.

TABLE 1

| No. | Compound | S1-T1 difference (eV) | S1 (nm) |
|---|---|---|---|
| B-2 | [structure] | 0.13 | 444 |
| B-2 | [structure] | 0.10 | 424 |
| B-3 | [structure] | 0.54 | 478 |

TABLE 1-continued

| No. | Compound | S1-T1 difference (eV) | S1 (nm) |
|---|---|---|---|
| B-4 | 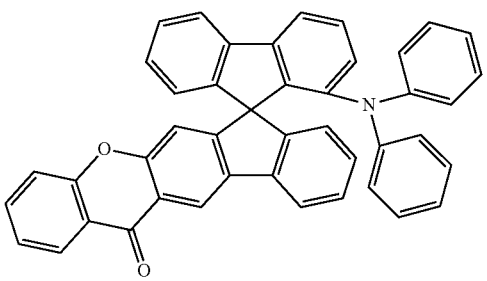 [SMILES: O=c1c2ccccc2oc2cc3c(cc12)-c1ccccc1C31c2ccccc2-c2cccc(N(c3ccccc3)c3ccccc3)c21] | 0.55 | 498 |

(6) When at least one of $X_1$, $X_4$, $X_5$, and $X_8$ and at least one of $X_{21}$, $X_{24}$, $X_{25}$, and $X_{28}$ are each an amino group, molecular stacking is less likely to occur, and thus molecular association can be less likely to occur.

When at least one of $X_1$, $X_4$, $X_5$, and $X_8$ and at least one of $X_{21}$, $X_{24}$, $X_{25}$, and $X_{28}$ are each an amino group, the basic skeleton is subjected to steric hindrance by the amino groups, somewhat distorting the molecule to lower the degree of flatness of the molecule. Thus, molecular stacking is less likely to occur, and molecular association can be less likely to occur.

In this case, when the compound according to the embodiment is used in the organic layer of an organic light-emitting device, a stable amorphous film that is less likely to crystallize is provided, and the organic light-emitting device can have high durability without the occurrence of crystallization even in the case of long-term operation.

In addition, in the case where the compound according to the embodiment is used in the light-emitting layer of an organic light-emitting device, molecular association is less likely to occur, and thus concentration quenching is less likely to occur. Accordingly, the organic light-emitting device can have high luminous efficiency.

Moreover, the compound is effective in improving the sublimability. The improvement of sublimability enables the purification of the material by sublimation and the production of an organic light-emitting device by vapor deposition. This can reduce the amount of impurities contained in the organic light-emitting device and can inhibit deteriorations in luminous efficiency and driving durability due to impurities.

Furthermore, the compound according to the embodiment can be used in the light-emitting layer of an organic light-emitting device. In this case, the compound has the following features below.

(7) The compound according to the embodiment is mixed with a host material in the light-emitting layer to facilitate exciton recombination of the compound according to the embodiment, thereby providing the light-emitting device with high efficiency.

(8) The mixture of the compound according to the embodiment and the host material in the light-emitting layer and the presence of a light-emitting material provide the light-emitting device with high efficiency and high color purity.

(9) The use of a hydrocarbon compound as the light-emitting material provides the light-emitting device with high efficiency and good durability characteristics.

These features will be described below.

(7) The compound according to the embodiment is mixed with a host material in the light-emitting layer to facilitate exciton recombination of the compound according to the embodiment, thereby providing the light-emitting device with high efficiency.

The compound according to the embodiment contains an electron-withdrawing carbonyl group and an electron-donating amino group. When the compound according to the embodiment is mixed with the host material in the light-emitting layer of the organic light-emitting device, the LUMO of the compound according to the embodiment is at a lower level (farther from the vacuum level) than that of the host material, and the HOMO of the compound according to the embodiment is at a higher level (closer to the vacuum level) than that of the host material. Accordingly, in the light-emitting layer, electrons and holes fed from the transport layer are trapped by the compound according to the embodiment, and exciton recombination occurs. As described in feature (1) above, the compound according to the embodiment has a small difference between S1 and T1, can efficiently produce delayed fluorescence in the light-emitting layer, and can use a larger number of triplet excitons for light emission. This effect is especially significant when the host material is a hydrocarbon compound. The reason for this is that the larger energy difference between the HOMO and LUMO of the host and those of the compound according to the embodiment leads to easier trapping of electrons and holes. The hydrocarbon compound is a compound that consists of only carbon and hydrogen in its molecule.

As described in feature (3) above, the compound according to the embodiment is less likely to undergo molecular association and thus is less likely to undergo concentration quenching in the host material. This effect leads to the prevention of quenching due to exciton interaction when the compound according to the embodiment is in the excited state, and is effective in efficiently producing delayed fluorescence in the light-emitting layer.

(8) The mixture of the compound according to the embodiment and the host material and the presence of a light-emitting material in the light-emitting layer provide the light-emitting device with high efficiency and high color purity.

The use of the light-emitting layer that contains the compound according to the embodiment and that is doped with a light-emitting material having a high emission quantum yield or a light-emitting material whose emission spectrum has a spectrum suitable for exhibiting high color purity provides a light-emitting device having even higher efficiency and high color purity. In this case, the compound according to the embodiment needs to be contained in a concentration sufficient to preferentially trap electrons and holes in the light-emitting layer in order to facilitate exciton recombination. The concentration of the organic compound according to the embodiment is preferably 0.1% or more by mass and 45% or less by mass, more preferably 1% or more by mass and 30% or less by mass based on the entire light-emitting layer.

As a light-emitting material, a smaller doping concentration is less susceptible to the influence of concentration quenching and a change in emission spectrum due to the interaction between molecules. Thus, the light-emitting layer can be doped with the light-emitting material other than the compound according to the embodiment. The concentration of the light-emitting material is preferably 0.01% or more by mass and 20% or less by mass, more preferably 1% or more by mass and 15% or less by mass based on the entire light-emitting layer. This provides the light-emitting device with high efficiency and high color purity.

(9) The use of a hydrocarbon compound as the light-emitting material provides the light-emitting device with high efficiency and good durability characteristics.

The compound according to the embodiment contains a strong electron-withdrawing carbonyl group. Because of this, as a light-emitting material serving as a dopant described in feature (8) above, a light-emitting material that does not contain an amino group, which is an electron-donating group, can be used, and a hydrocarbon compound can be used. The reason for this is that an amino group-containing light-emitting material may interact with the carbonyl group of the compound according to the embodiment in the light-emitting layer to cause a decrease in luminous efficiency due to exciplex formation and a change in the emission spectrum of the light-emitting material, thereby deteriorating the color purity of the light-emitting device.

An amino group-containing light-emitting material is easily oxidized due to its low ionization potential and thus has poor device durability. For this reason, a hydrocarbon compound can be used as a light-emitting material, and a five-membered ring-containing fused polycyclic compound can be used. This is because the structure is less susceptible to oxidation due to its higher ionization potential. A hydrocarbon compound is a compound consisting of only carbon and hydrogen in its molecule.

As described above, the organic light-emitting device having high luminous efficiency can be provided by mixing the compound according to the embodiment with the host material in the light-emitting layer. Here, the light-emitting material may be the compound according to the embodiment. In addition, a light-emitting material may be mixed, and the compound according to the embodiment may function as an assist material.

The use of a light-emitting material with good color purity makes it possible to provide an organic light-emitting device with high efficiency and high color purity. When the host material is a hydrocarbon compound, the compound according to the embodiment can easily trap electrons and holes to contribute to higher efficiency.

Specific examples of the organic compound according to the embodiment are illustrated below. However, the present disclosure is not limited thereto.

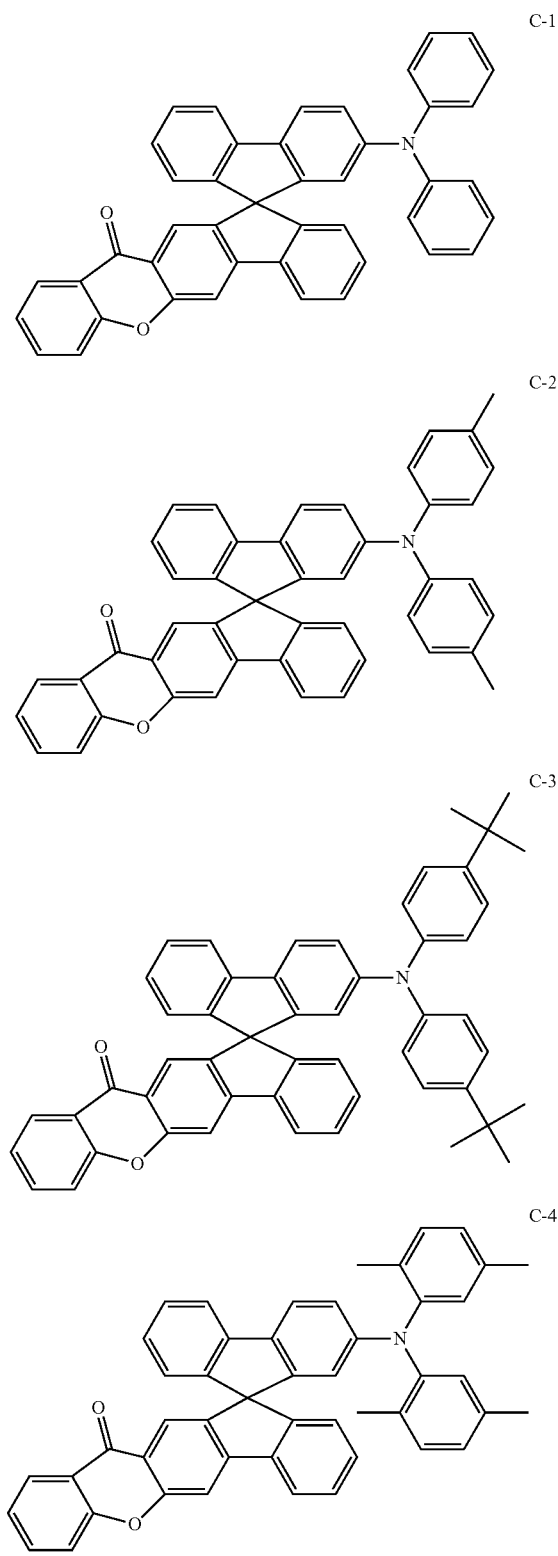

-continued
C-5
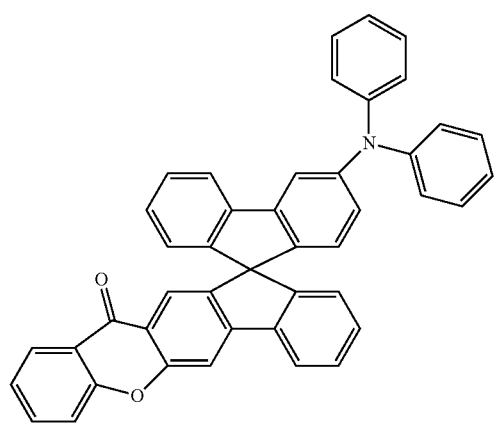
C-8
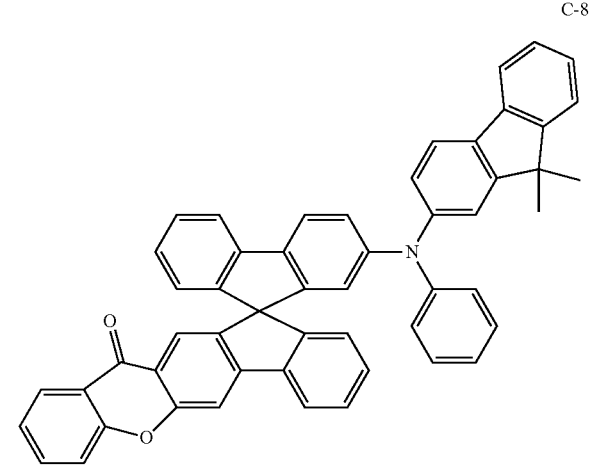
C-6
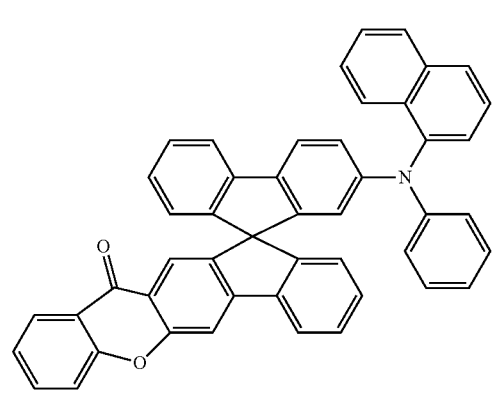
C-9
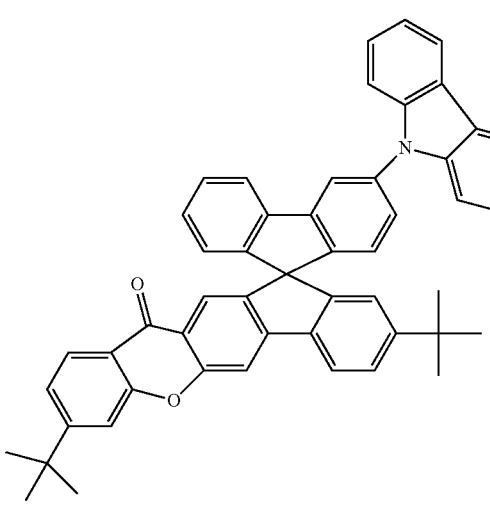
C-7
C-10
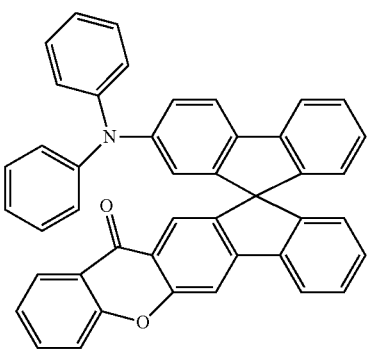

C-11
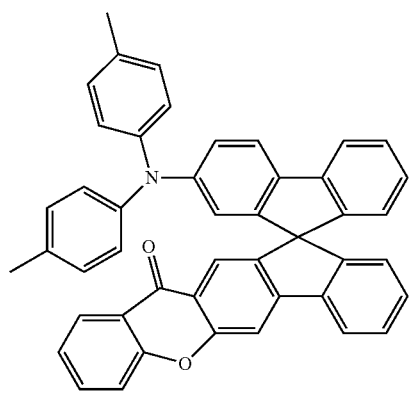
C-12
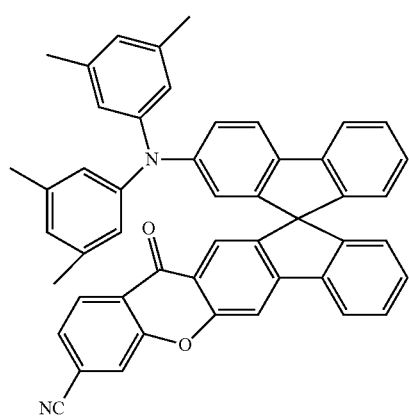
C-13
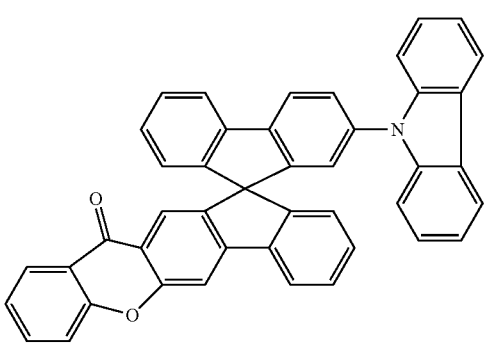
C-14
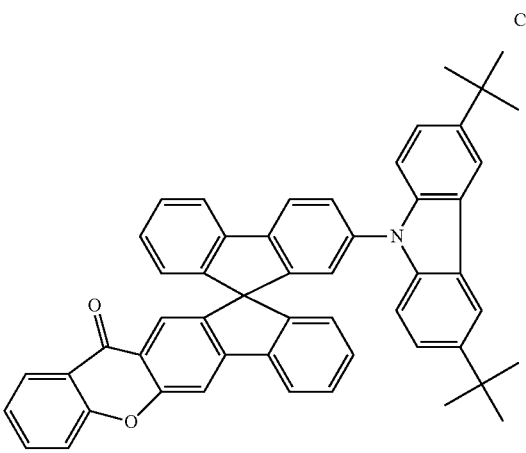
C-15
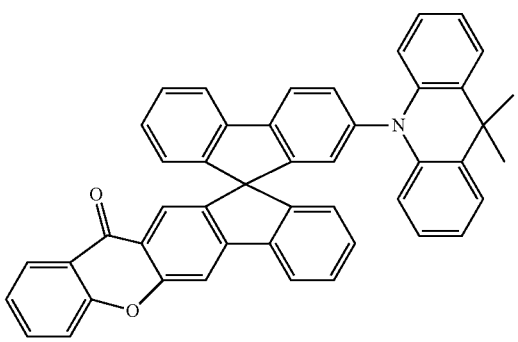
C-16
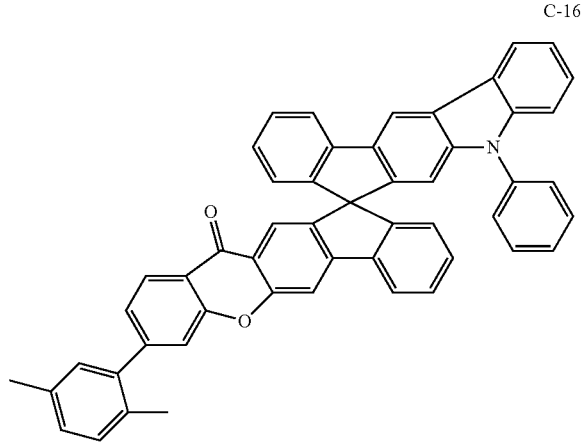
C-17
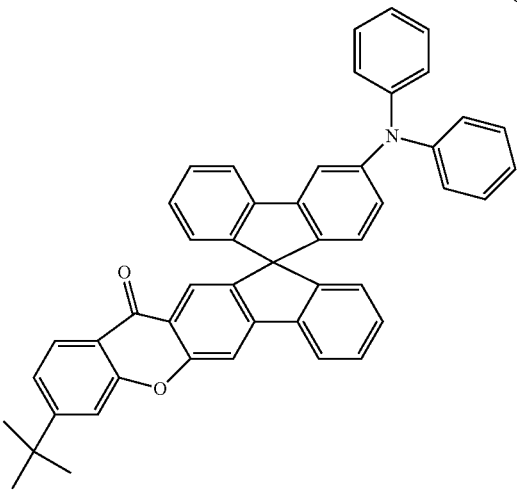

-continued
C-18
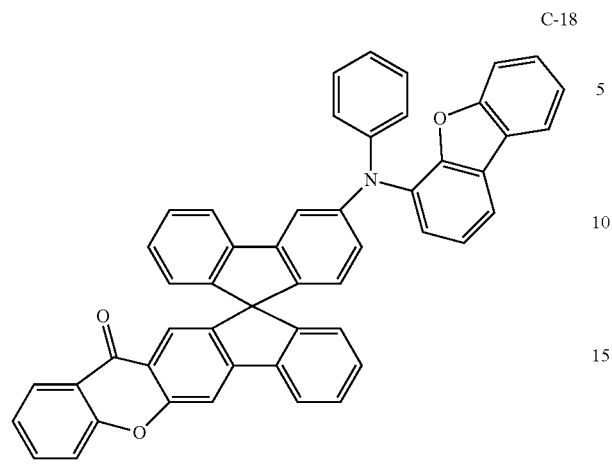
C-19
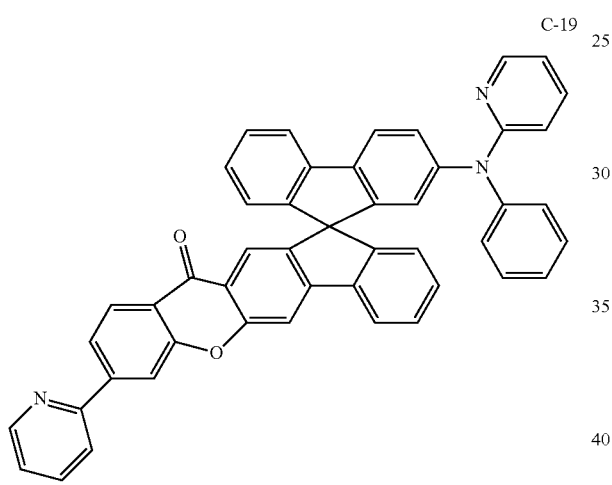
C-20
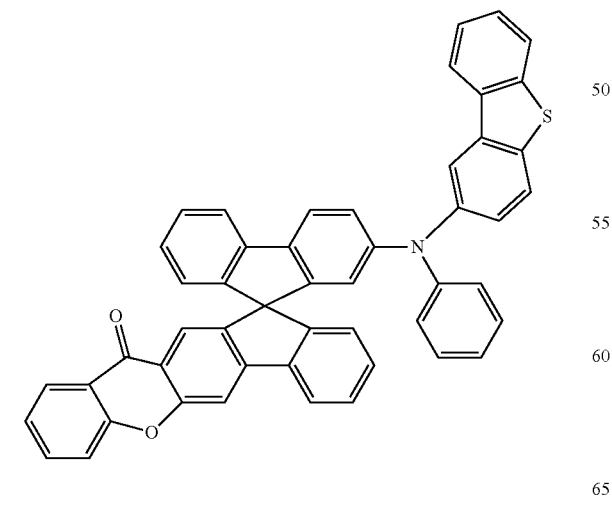
-continued
C-21
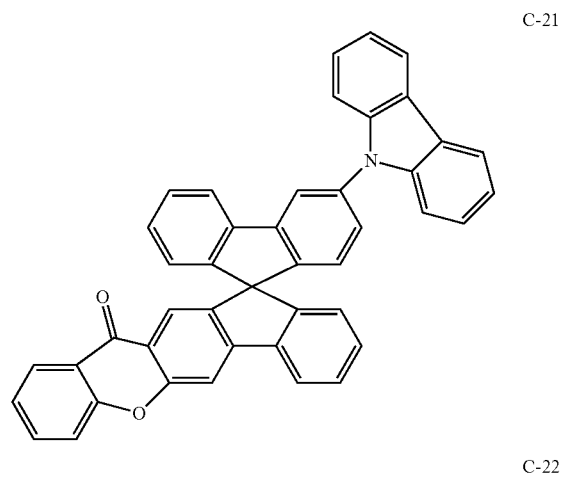
C-22
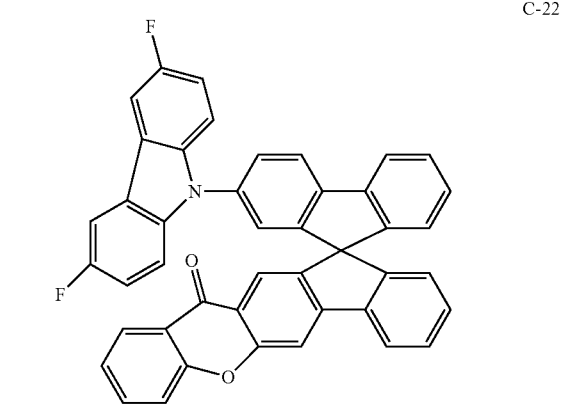
C-23
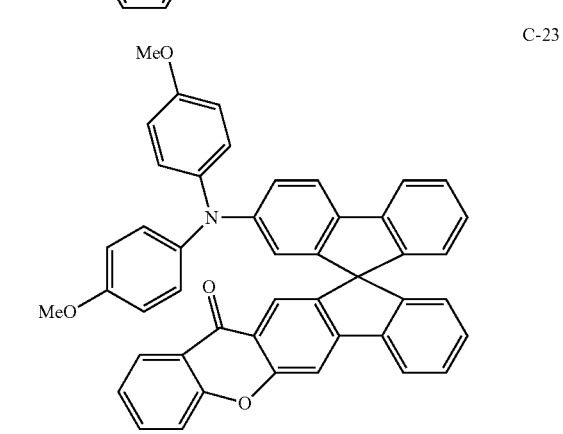
C-24
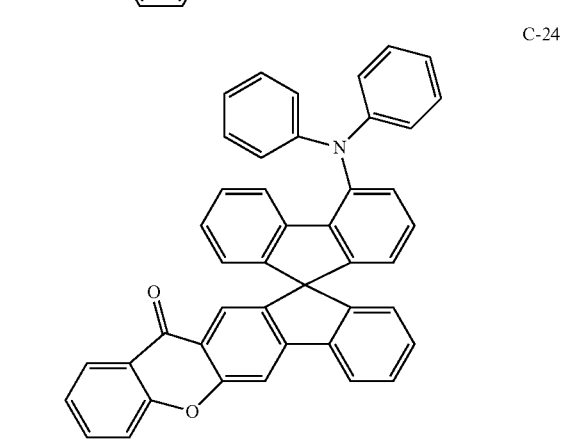

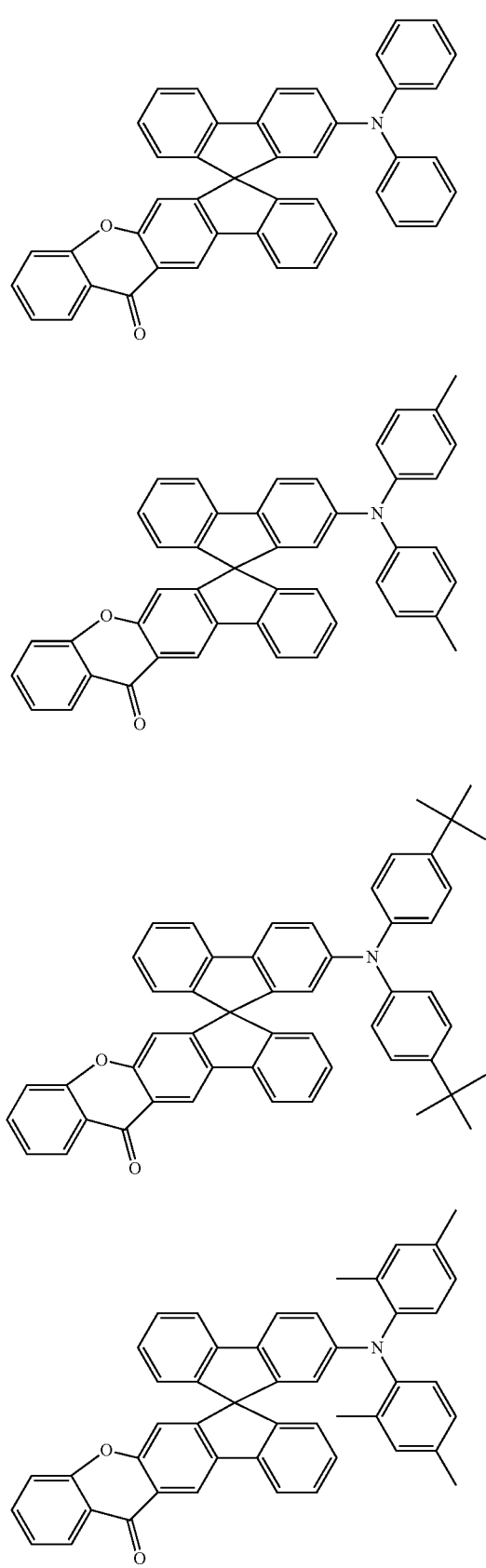
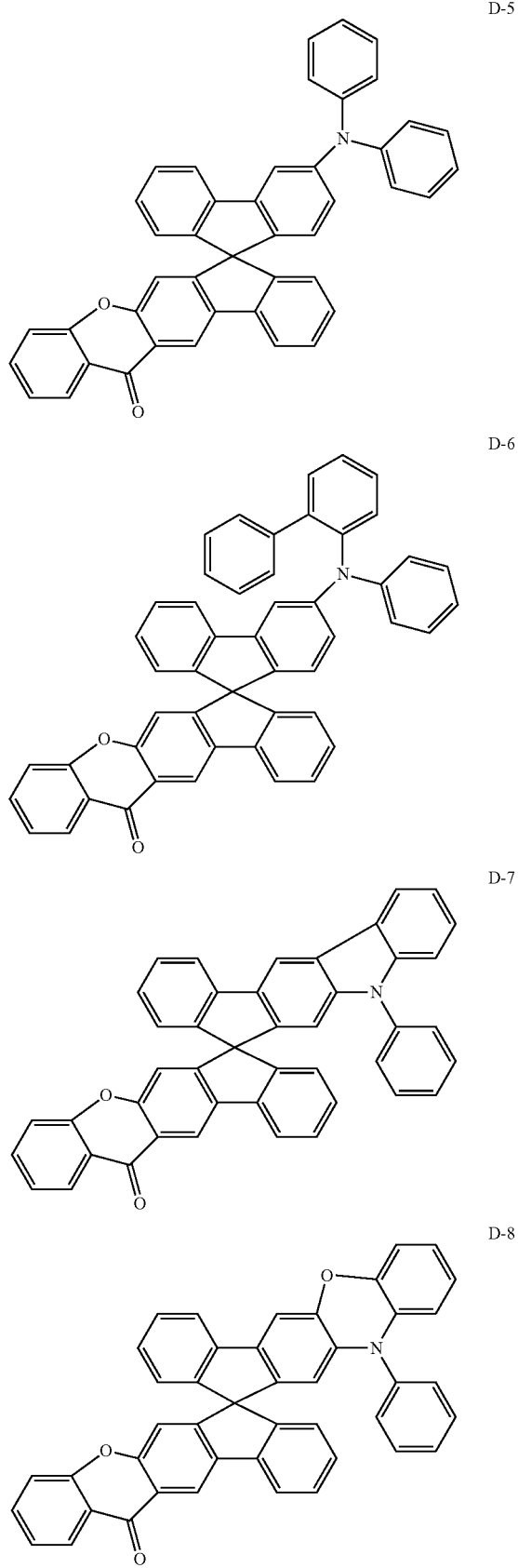

-continued
D-9
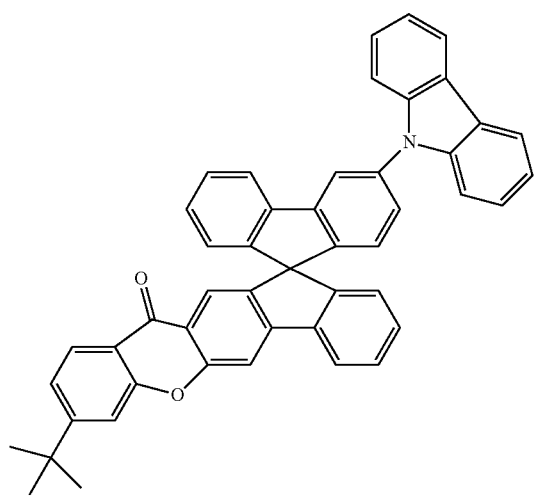
D-10
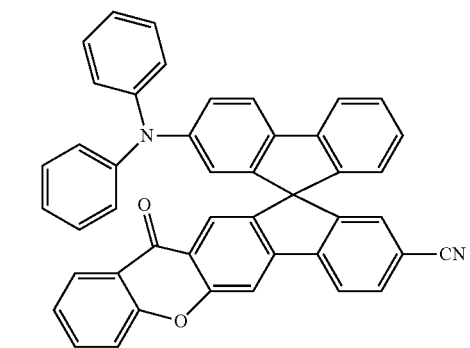
D-11
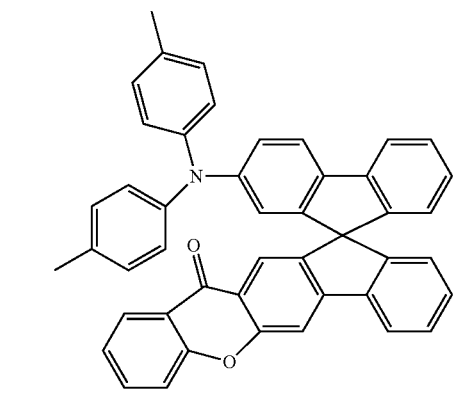
D-12
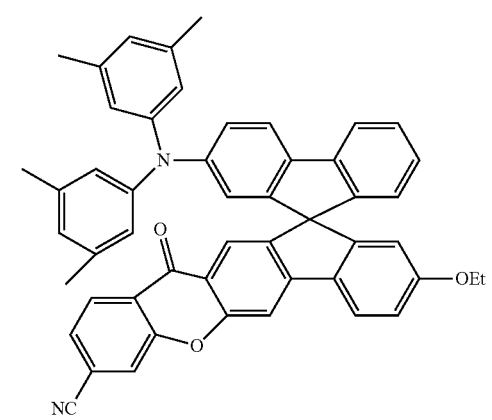
-continued
E-1
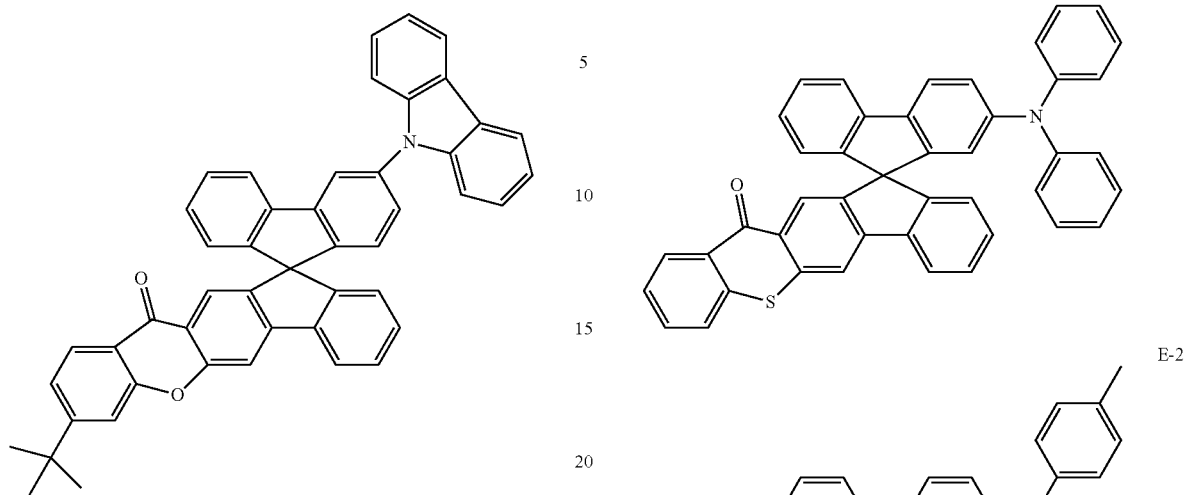
E-2
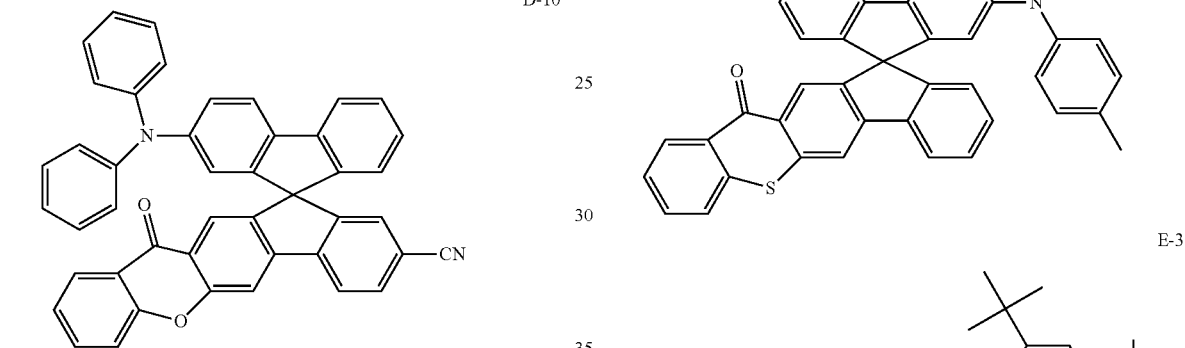
E-3
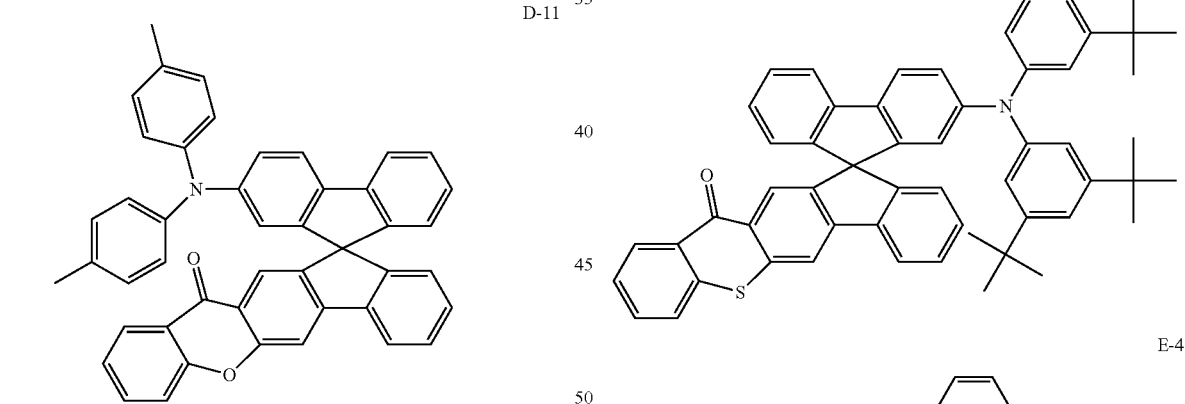
E-4
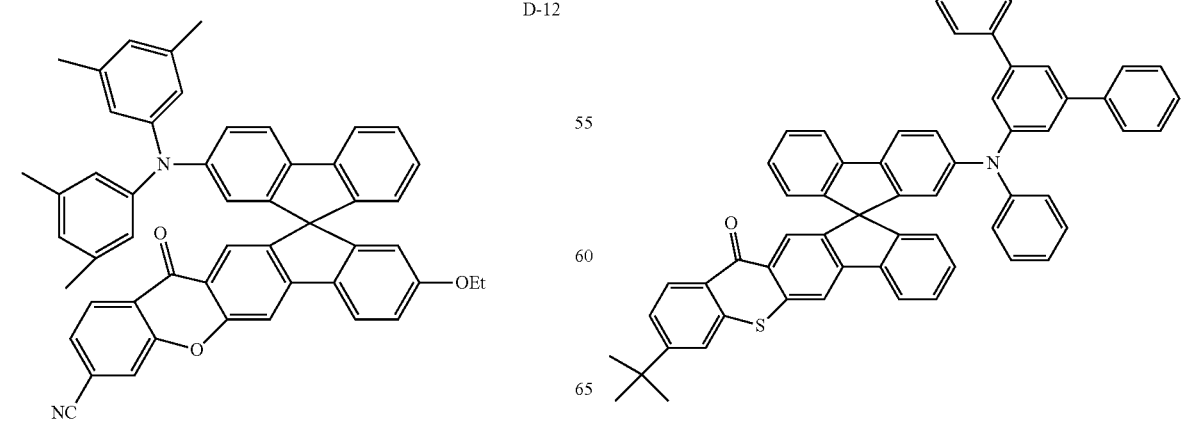

E-5
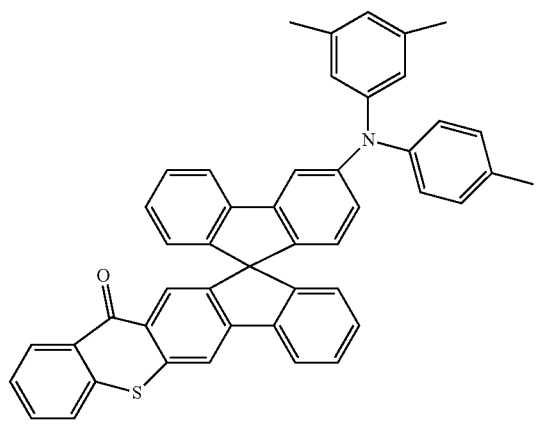
E-6
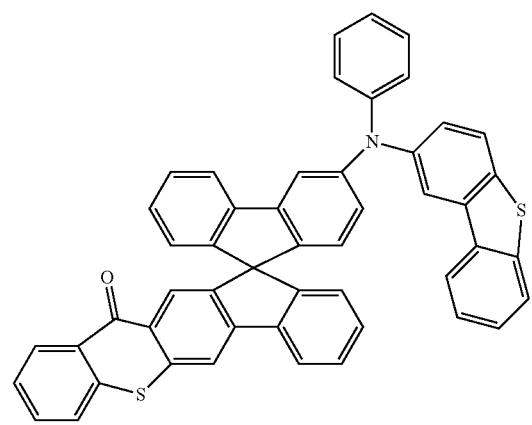
E-7
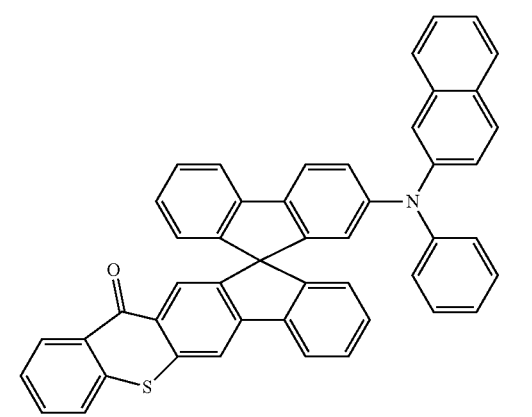
E-8
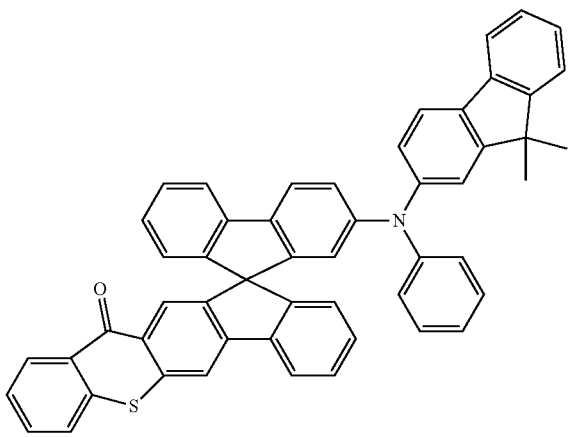
E-9
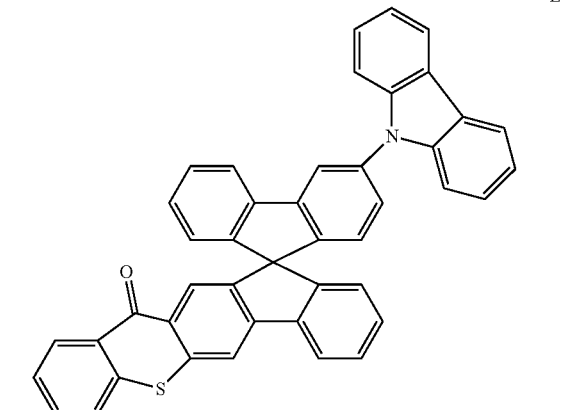
E-10
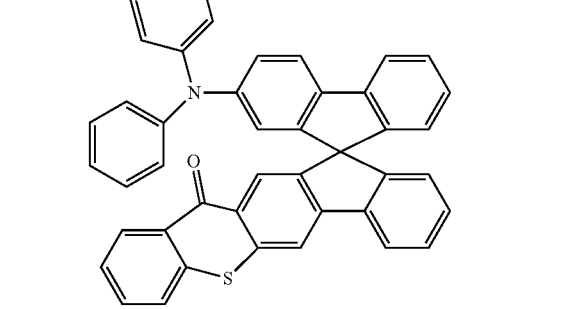
E-11
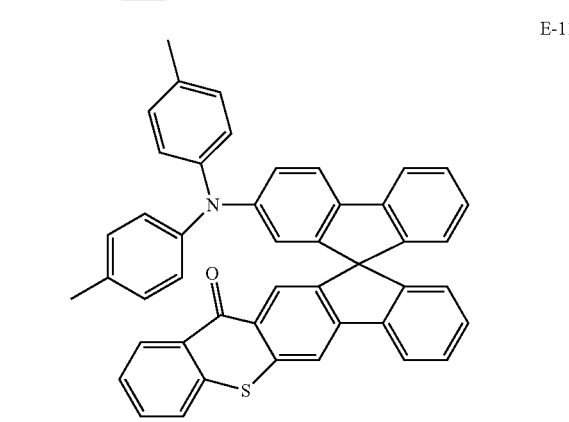

E-12
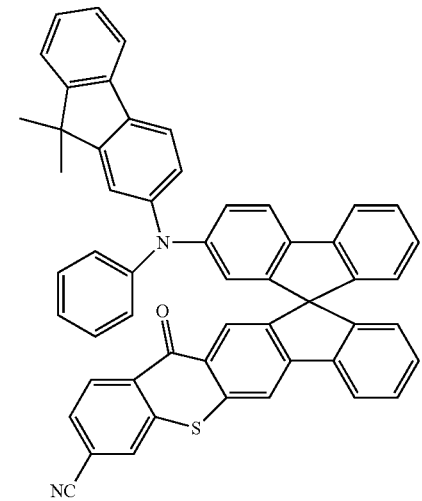
E-13
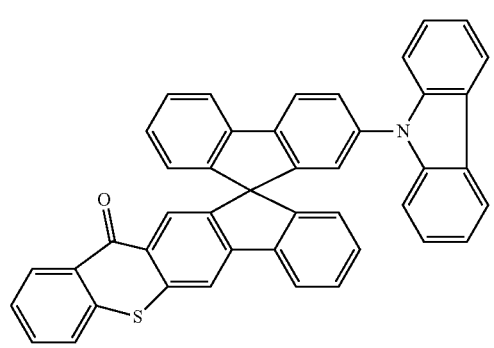
E-14
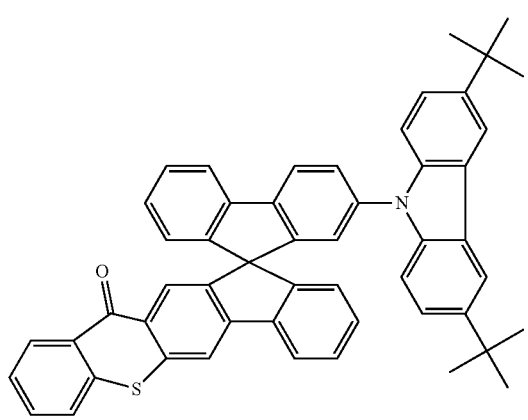
E-15
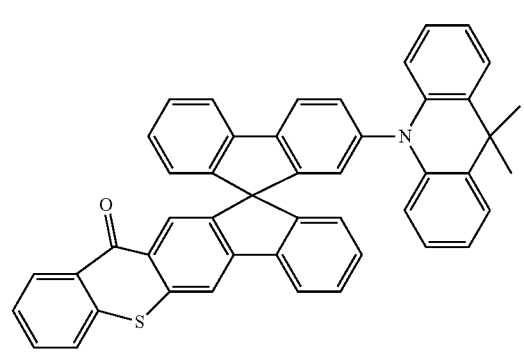
E-16
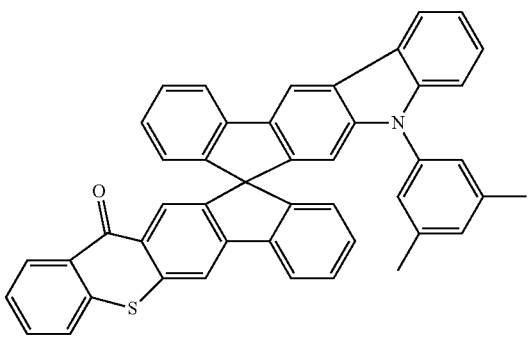
E-17
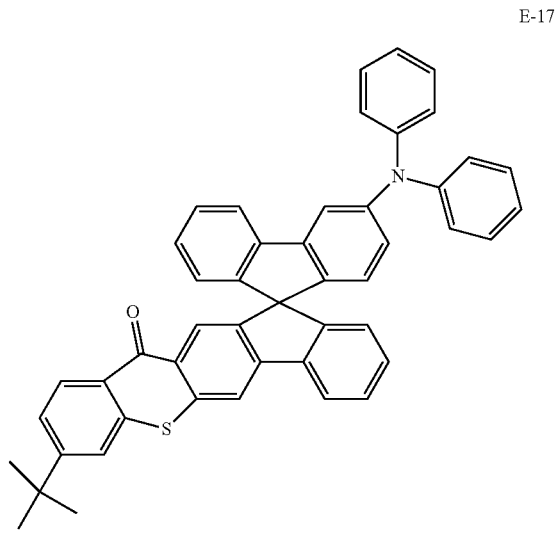
E-18
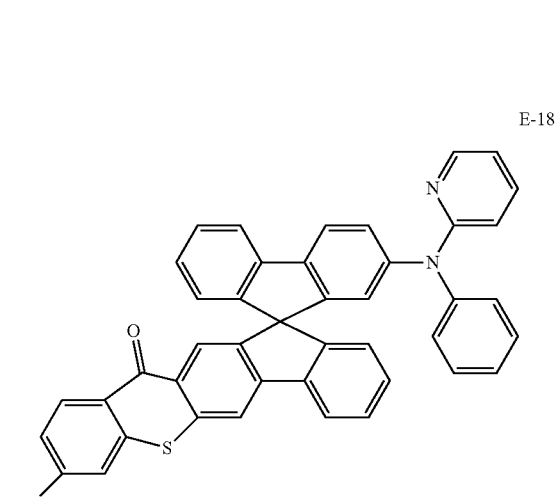

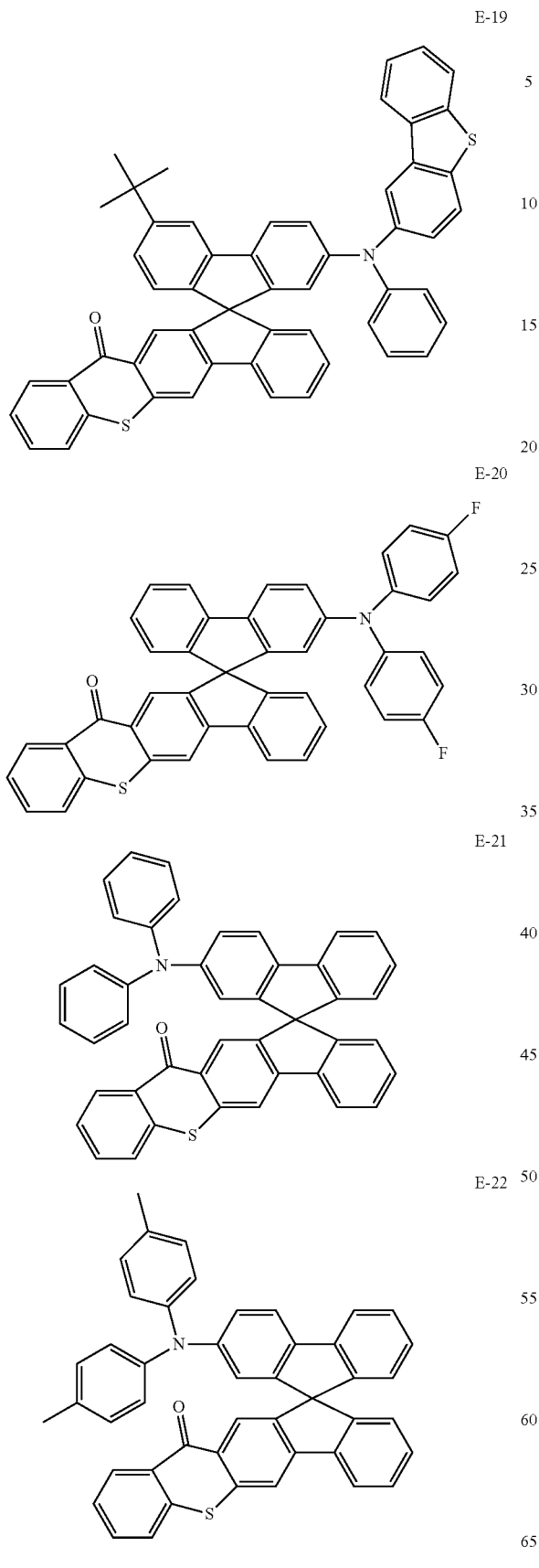
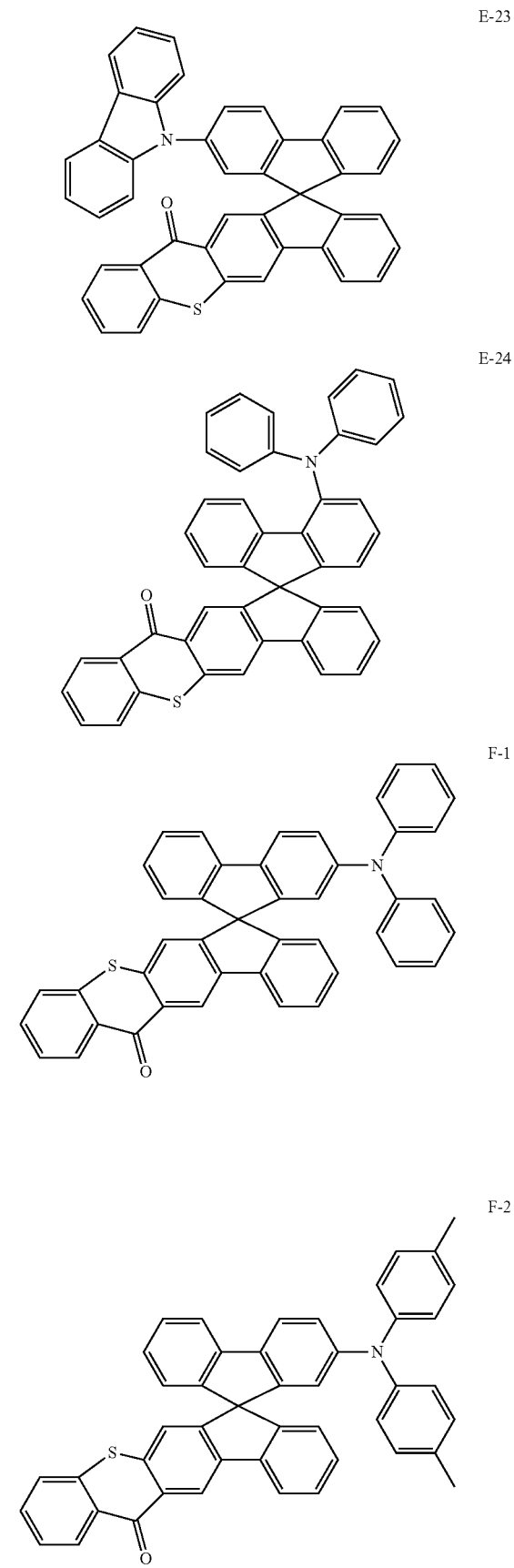

-continued
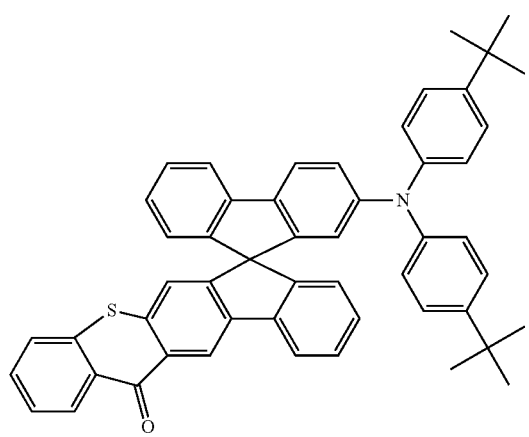
F-3
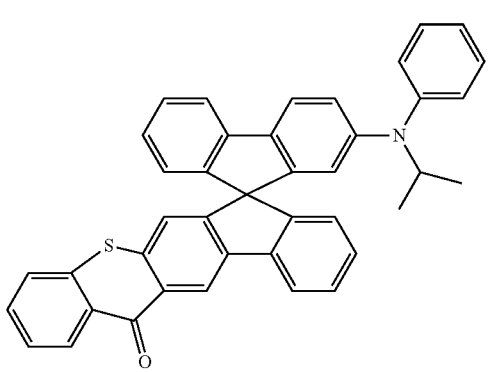
F-4
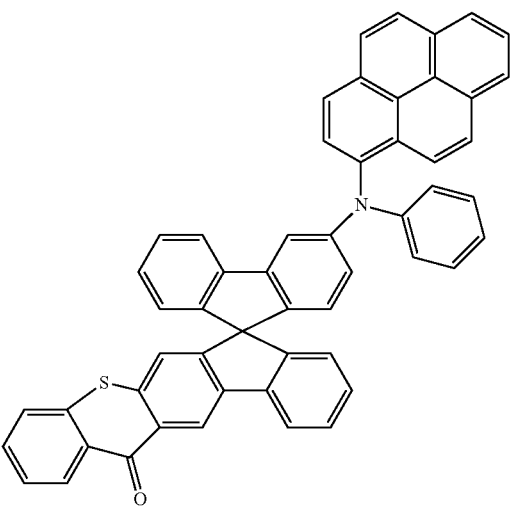
F-5
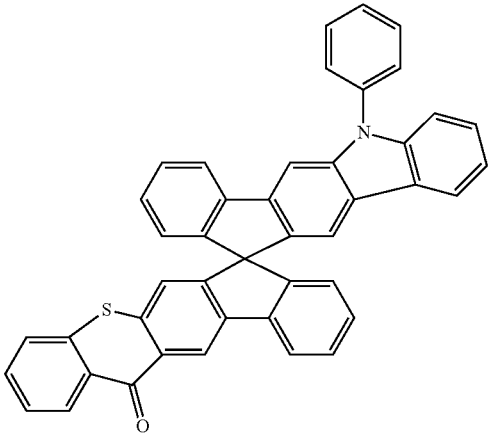
F-6
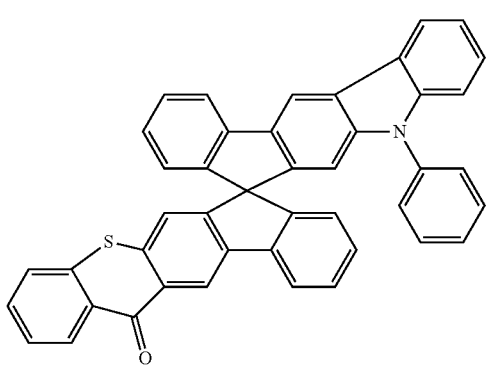
F-7
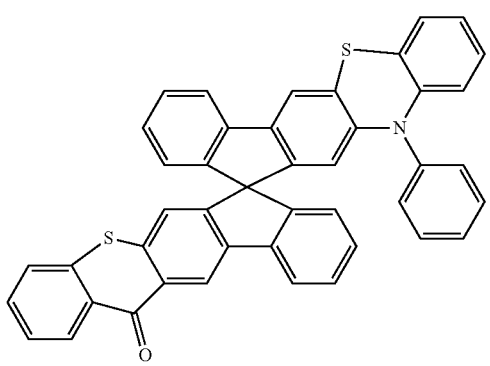
F-8
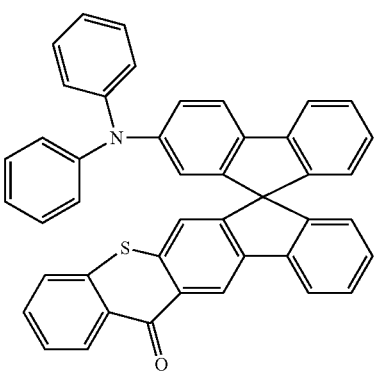
F-9

F-10
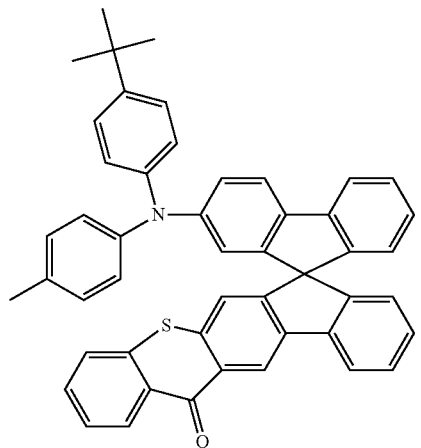
F-11
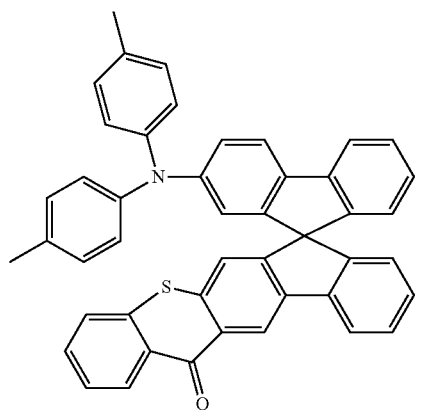
F-12
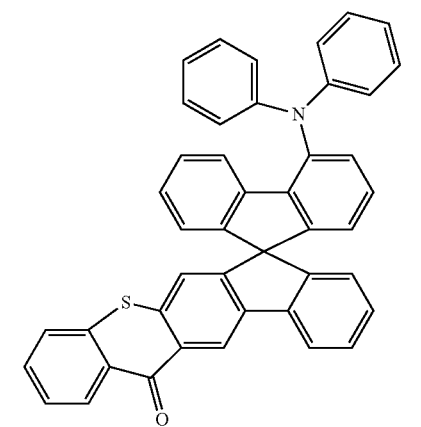
G-1
G-2
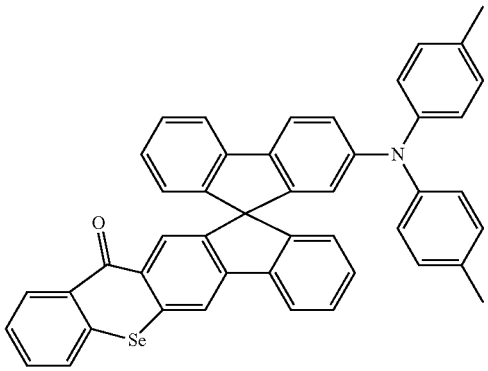
G-3
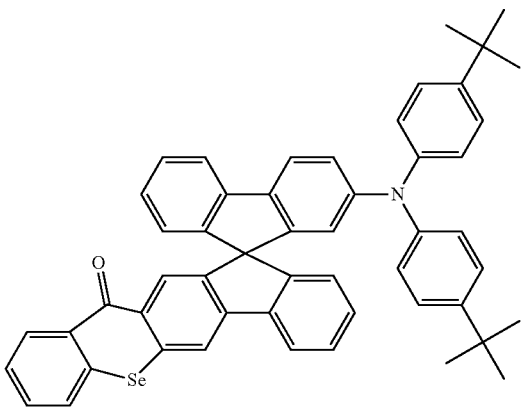
G-4
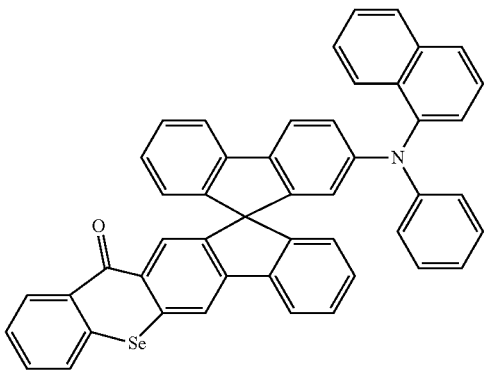
G-5
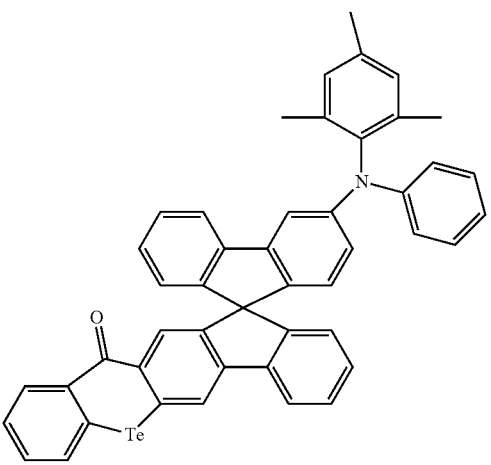

-continued
G-6
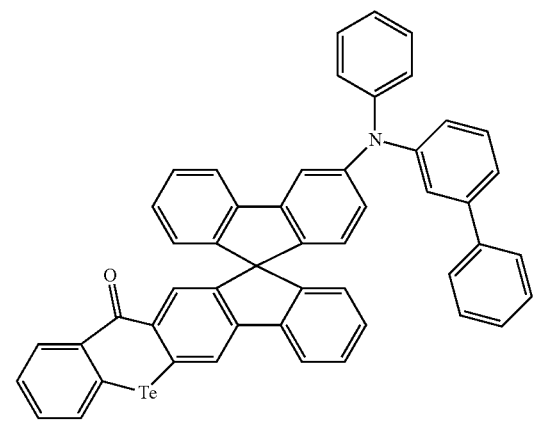
G-7
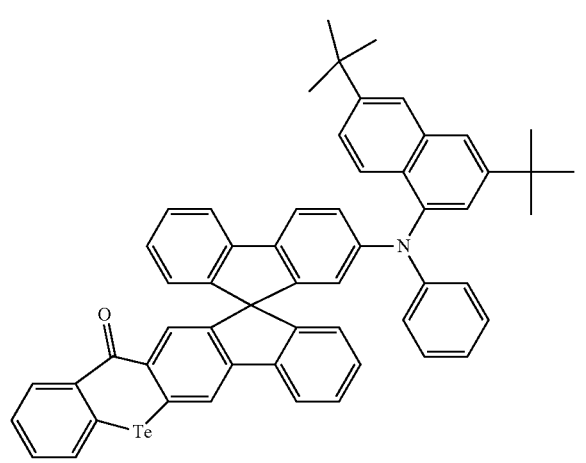
G-8
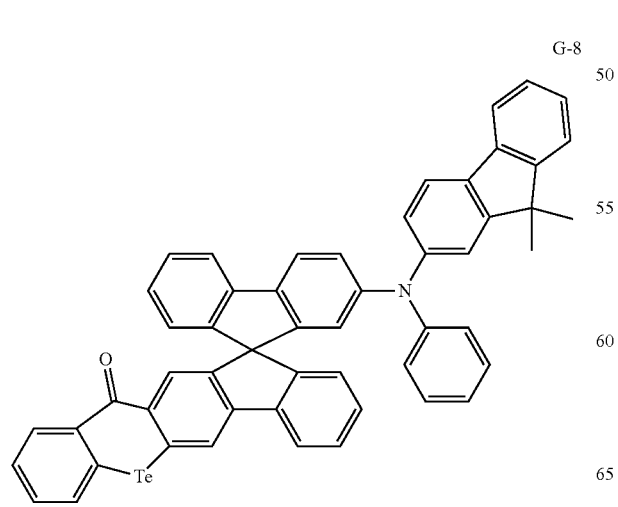
-continued
G-9
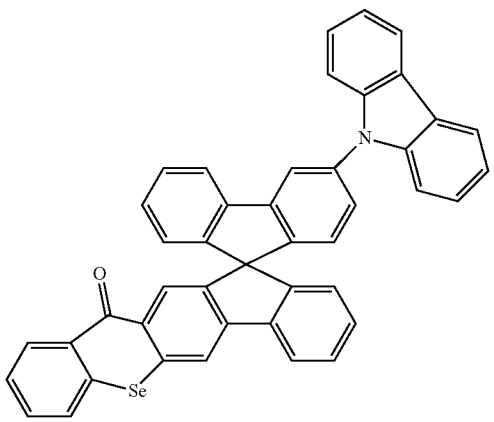
G-10
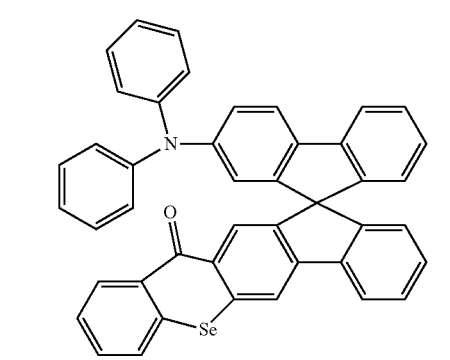
G-11
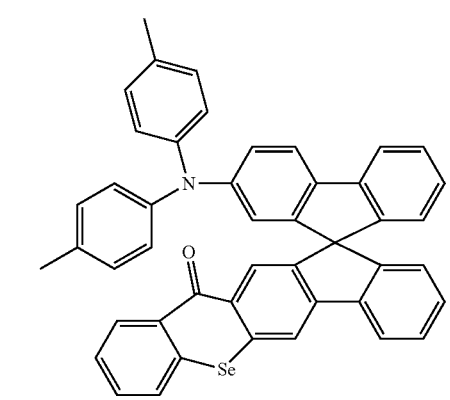
G-12
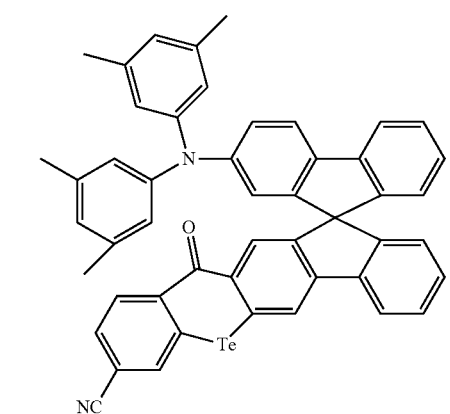

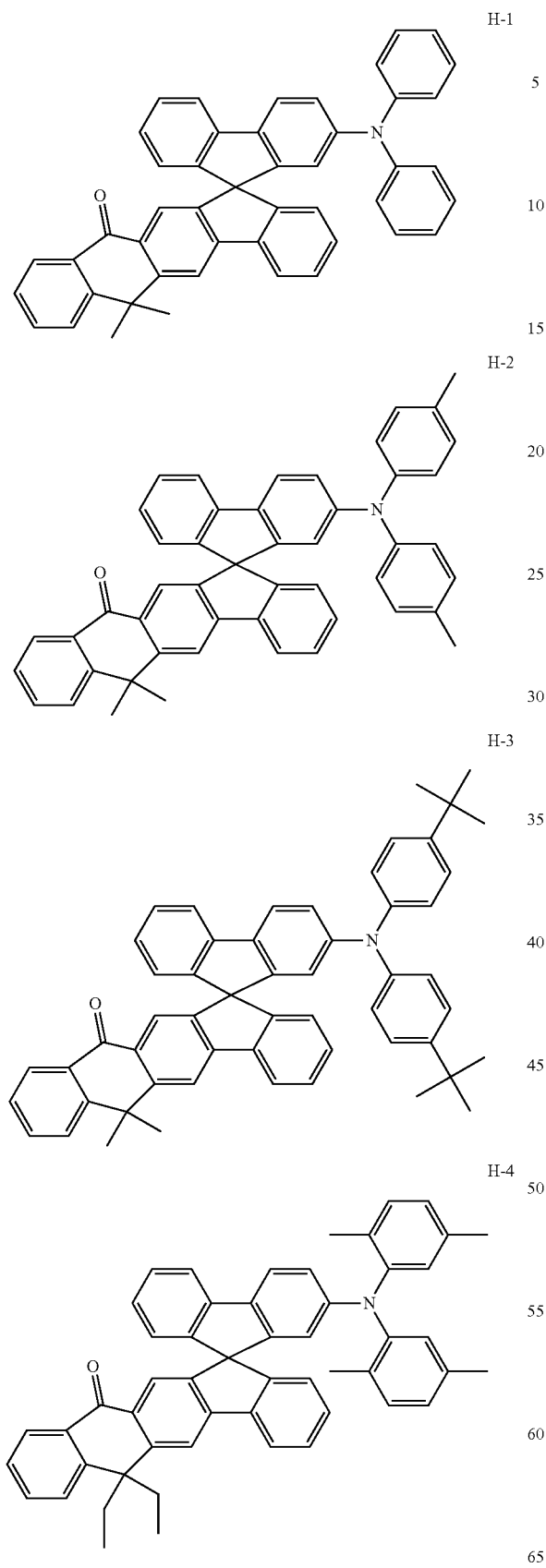
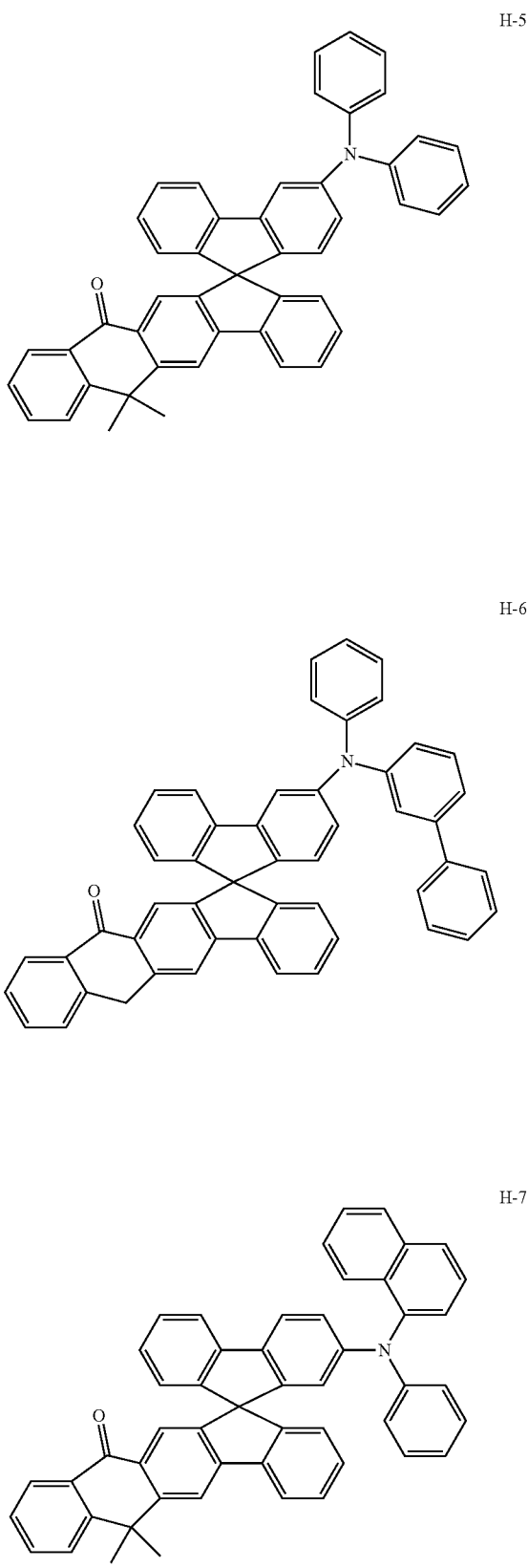

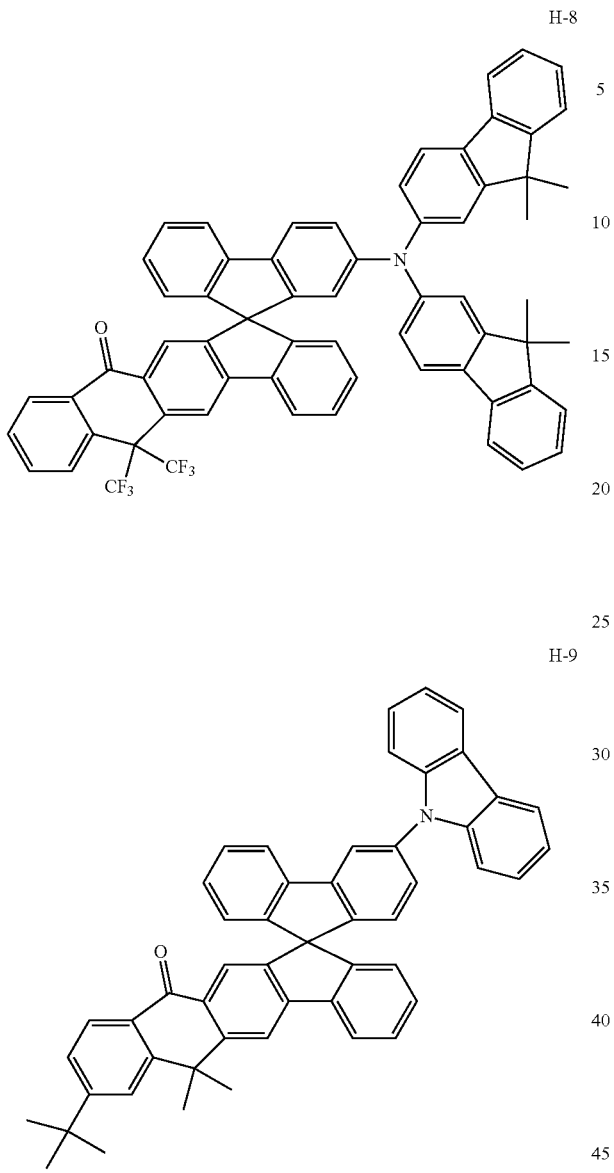

H-8

H-9

H-10

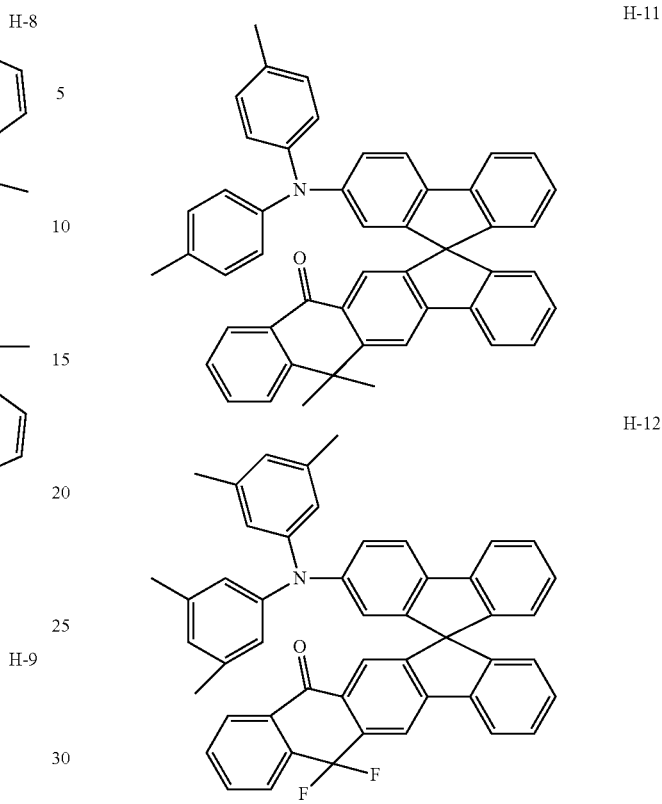

H-11

H-12

Compounds belonging to group C are each a compound in which Y is oxygen in the compound represented by formula [1]. Compounds belonging to group D are each a compound in which Y is oxygen in the compound represented by formula [2]. The fact that Y is oxygen inhibits the occurrence of a chemical reaction, such as oxidation, and thus provides a chemically stable compound.

Compounds belonging to group E are each a compound in which Y is sulfur in the compound represented by formula [1]. Compounds belonging to group F are each a compound in which Y is sulfur in the compound represented by formula [2]. When Y is sulfur, because the elemental radius of sulfur is larger than that of oxygen, the six-membered ring formed has a distorted structure, lowering the degree of flatness of the molecule. Thus, the concentration quenching is even less likely to occur.

Compounds belonging to group G are each a compound in which Y is selenium or tellurium in the compound represented by formula [1] or [2]. When Y is selenium or tellurium, because the element has a d-orbital and metallic properties, resulting in high electron mobility.

Compounds belonging to group H are each a compound in which Y is a $CR_1CR_2$ group in the compound represented by formula [1] or [2]. When $R_1$ and $R_2$ are introduced, especially when $R_1$ and $R_2$ are groups other than hydrogen, the degree of flatness of the molecule is reduced. Thus, the concentration quenching is even less likely to occur. Organic Light-Emitting Device The organic light-emitting device according to the embodiment will be described below.

The organic light-emitting device according to the embodiment at least includes an anode and a cathode, which are a pair of electrodes, and an organic compound layer disposed between these electrodes. In the organic light-emitting device according to the embodiment, the organic compound layer may be formed of a single layer or a multilayer stack including multiple layers, as long as it includes a light-emitting layer. In the case where the organic compound layer is formed of a multilayer stack including multiple layers, the organic compound layer may include, in addition to the light-emitting layer, a hole injection layer, a hole transport layer, an electron-blocking layer, a hole/exciton-blocking layer, an electron transport layer, an electron injection layer, and so forth. The light-emitting layer may be formed of a single layer or a multilayer stack including multiple layers.

In the organic light-emitting device according to the embodiment, at least one organic compound layer contains the organic compound according to the embodiment. Specifically, the organic compound according to the embodiment is contained in any of the light-emitting layer, the hole injection layer, the hole transport layer, the electron-blocking layer, the hole/exciton-blocking layer, the electron transport layer, the electron injection layer, and so forth described above. The organic compound according to the embodiment can be contained in the light-emitting layer. The light-emitting layer can emit green light or red light. The emission color is not limited thereto.

In the organic light-emitting device according to the embodiment, in the case where the organic compound according to the embodiment is contained in the light-emitting layer, the light-emitting layer may consist of only the organic compound according to the embodiment or may be composed of the organic compound according to the embodiment and another compound. In the case where the light-emitting layer is composed of the organic compound according to the embodiment and another compound, the organic compound according to the embodiment may be used as a host or a guest in the light-emitting layer. The organic compound may be used as an assist material that can be contained in the light-emitting layer. The term "host" used here refers to a compound having the highest proportion by mass in compounds constituting the light-emitting layer. The term "guest" refers to a compound that has a lower proportion by mass than the host in the compounds constituting the light-emitting layer and that is responsible for main light emission. The term "assist material" refers to a compound that has a lower proportion by mass than the host in the compounds constituting the light-emitting layer and that assists the light emission of the guest.

In the case where the organic compound according to the embodiment is used as a guest in the light-emitting layer, the concentration of the guest is preferably 0.01% or more by mass and 20% or less by mass, more preferably 1% or more by mass and 15% or less by mass, based on the entire light-emitting layer. In the case where the organic compound according to the embodiment is used as an assist material in the light-emitting layer, the concentration of the assist material is preferably 0.1% or more by mass and 45% or less by mass, more preferably 1% or more by mass and 30% or less by mass, based on the entire light-emitting layer.

In the case where the organic compound according to the embodiment is used as a guest in the light-emitting layer, a material having a higher LUMO level than the organic compound according to the embodiment (a material having a LUMO level closer to the vacuum level) can be used as a host. The reason for this is as follows: The organic compound according to the embodiment tends to have a low LUMO level. Thus, when a material having a higher LUMO level than the organic compound according to the embodiment is used as a host, the organic compound according to the embodiment can receive more electrons supplied to the host of the light-emitting layer.

In the case where the organic compound according to the embodiment is used as an assist material in the light-emitting layer, a material having a higher LUMO level than the organic compound according to the embodiment (a material having a LUMO level closer to the vacuum level) can be used as a guest. The reason for this is as follows: The organic compound according to the embodiment tends to have a low LUMO level. Thus, when a material having a higher LUMO level than the organic compound according to the embodiment is used as a light-emitting material (guest), the organic compound according to the embodiment receives more electrons supplied to the host of the light-emitting layer, and the assist material is responsible for exciton recombination. This enables efficient energy transfer to the light-emitting material (guest).

The inventors have conducted various studies and have found that when the organic compound according to the embodiment is used as a host, guest, or assist material of a light-emitting layer, especially as a guest of a light-emitting layer, a device that emits light with high efficiency and high luminance, and is extremely durable can be provided. The inventors have further found that when the organic compound according to the embodiment is used as an assist material in the light-emitting layer, a device that emits light with high efficiency and high luminance, and is extremely durable can be provided. The light-emitting layer may be formed of a single layer or multiple layers, and can contain multiple light-emitting materials. The term "multiple layers" may include a state in which the light-emitting layer and another light-emitting layer are stacked, or a state in which an intermediate layer is stacked between multiple light-emitting layers. Tandem devices or stacked devices are also acceptable. In these cases, the emission color of the organic light-emitting device is not limited to a single color. More specifically, the emission color may be white or an intermediate color. A film-forming method is vapor deposition or coating. Details will be described in examples below.

The organic compound according to the embodiment can be used as a constituent material of an organic compound layer other than the light-emitting layer included in the organic light-emitting device according to the embodiment. Specifically, the organic compound may be used as a constituent material of the electron transport layer, the electron injection layer, the hole transport layer, the hole injection layer, the hole-blocking layer, and so forth.

For example, a hole injection compound, a hole transport compound, a compound to be used as a host, a light-emitting compound, an electron injection compound, or an electron transport compound, which is known and has a low or high molecular weight, can be used together with the organic compound according to the embodiment, as needed. Examples of these compounds will be described below.

As a hole injection-transport material, a material having a high hole mobility can be used so as to facilitate the injection of holes from the anode and to transport the injected holes to the light-emitting layer. To reduce a deterioration in film quality, such as crystallization, in the organic light-emitting device, a material having a high glass transition temperature can be used. Examples of a low- or high-molecular-weight material having the ability to inject and transport holes include triarylamine derivatives, aryl carbazole derivatives, phenylenediamine derivatives, stilbene derivatives, phthalocyanine derivatives, porphyrin derivatives, poly(vinyl carbazole), polythiophene, and other conductive polymers. Moreover, the hole injection-transport material can be used for the electron-blocking layer. Non-limiting specific examples of a compound used as the hole injection-transport material will be illustrated below.

HT1 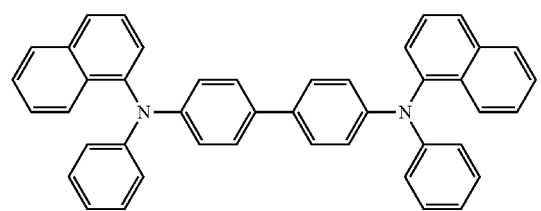
HT2 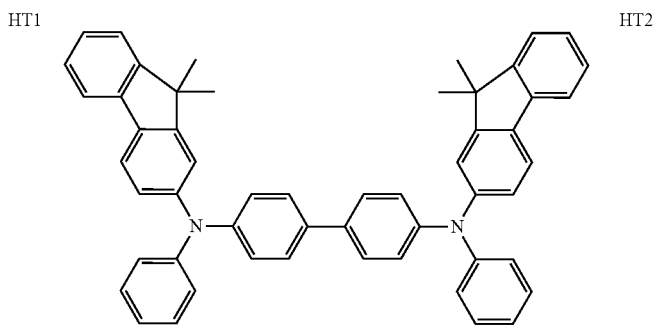
HT3 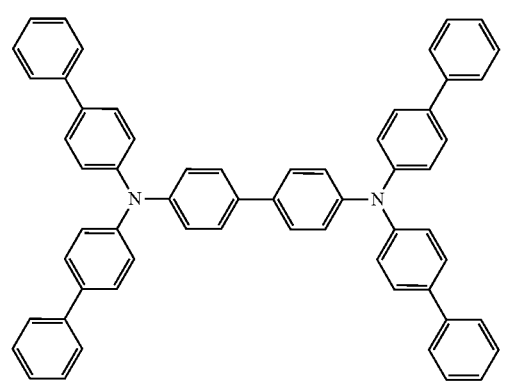
HT4 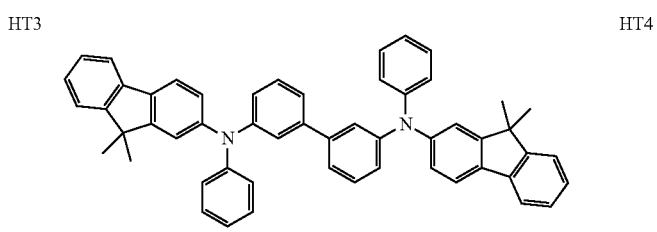
HT5 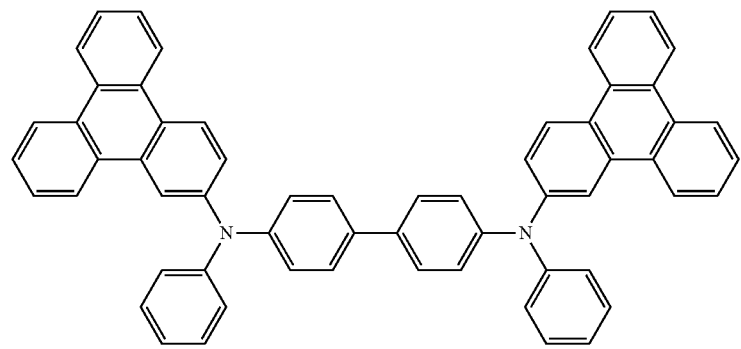
HT6 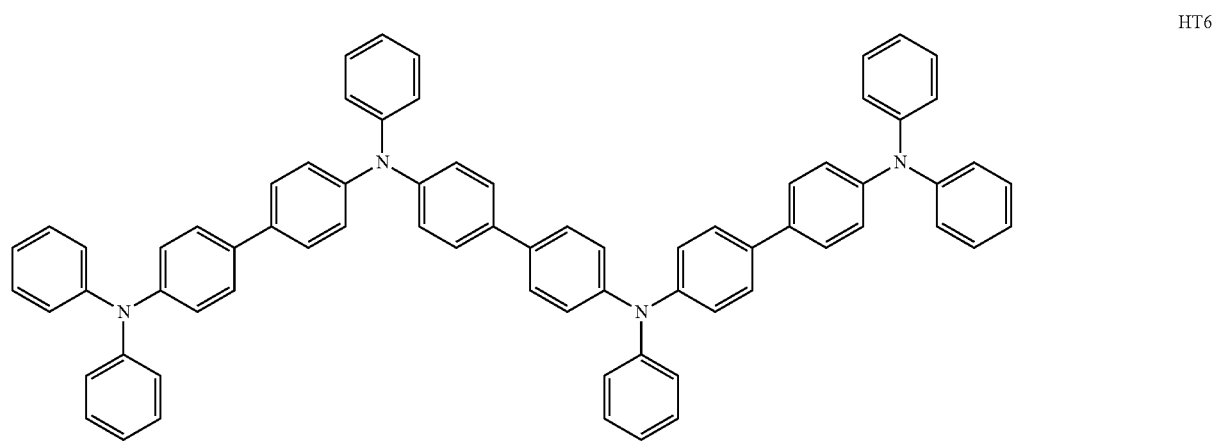

-continued
HT7
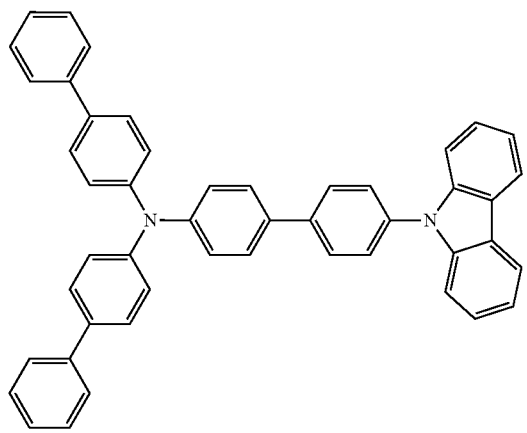
HT8
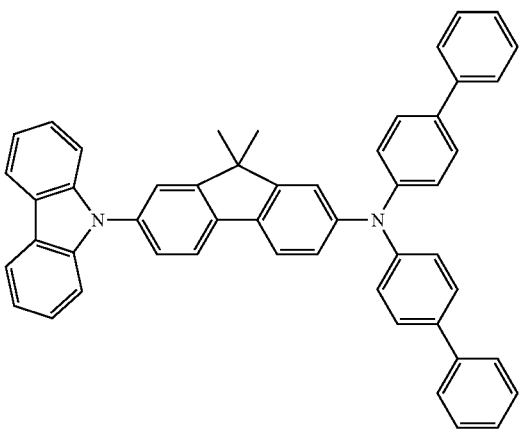
HT9
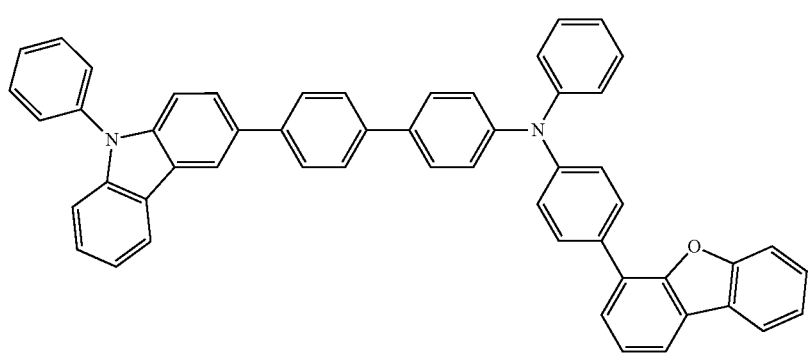
HT10
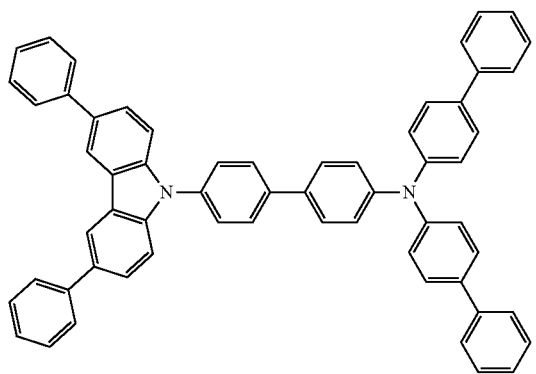
HT11
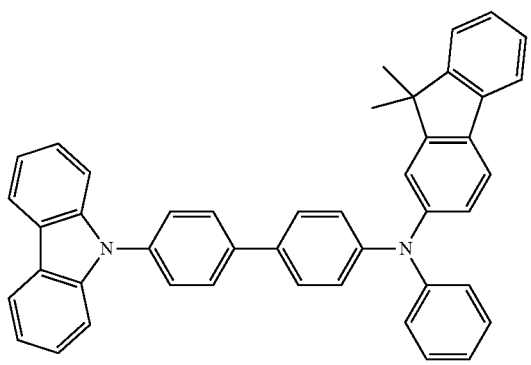
HT12
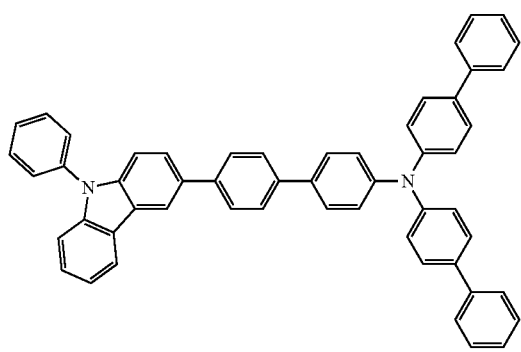
HT13
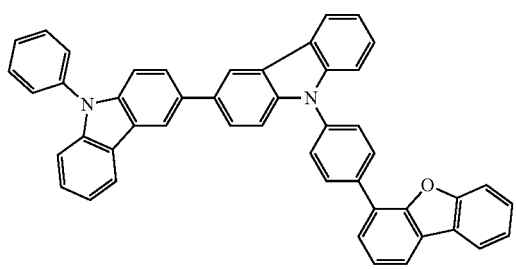

HT14
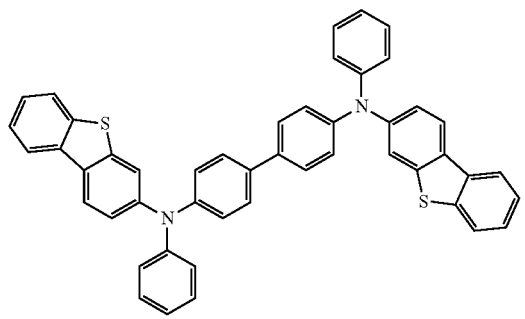

HT15
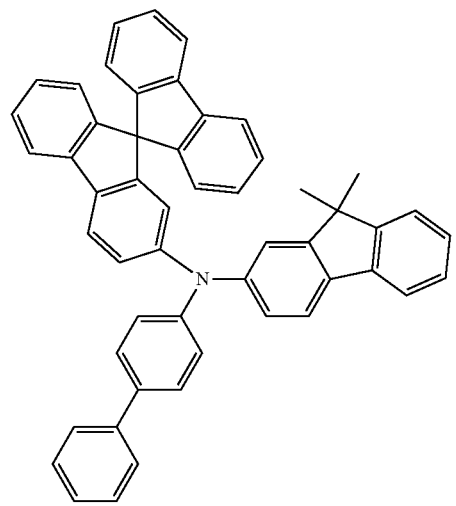

HT16
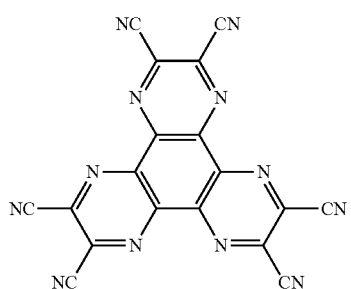

HT17
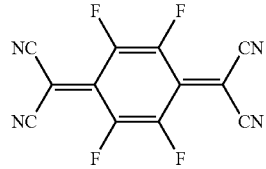

HT18
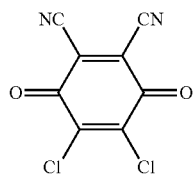

HT19
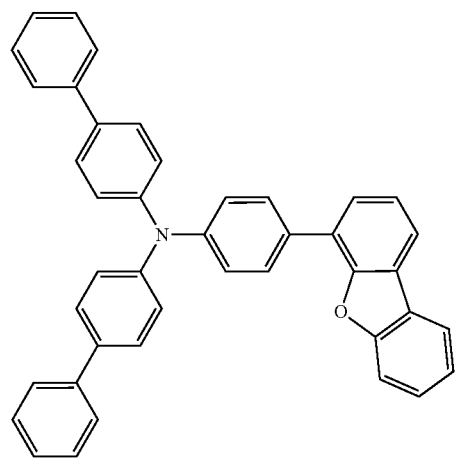

Among the hole transport materials illustrated above, HT16 to HT18 can be used in the layer in contact with the anode to reduce the driving voltage. HT16 is widely used in organic light-emitting devices. HT2, HT3, HT4, HT5, HT6, HT10, and HT12 may be used in an organic compound layer adjacent to HT16. Multiple materials may be used in a single organic compound layer.

Examples of a light-emitting material mainly associated with a light-emitting function include, in addition to the organic compounds represented by formulae [1] and [2], fused-ring compounds, such as fluorene derivatives, naphthalene derivatives, pyrene derivatives, perylene derivatives, tetracene derivatives, anthracene compounds, and rubrene, quinacridone derivatives, coumarin derivatives, stilbene derivatives, organoaluminum complexes, such as tris(8-quinolinolato)aluminum, iridium complexes, platinum complexes, rhenium complexes, copper complexes, europium complexes, ruthenium complexes, and polymer derivatives, such as poly(phenylene vinylene) derivatives, polyfluorene derivatives, and polyphenylene derivatives. Non-limiting specific examples of a compound used as a light-emitting material are illustrated below.

BD1
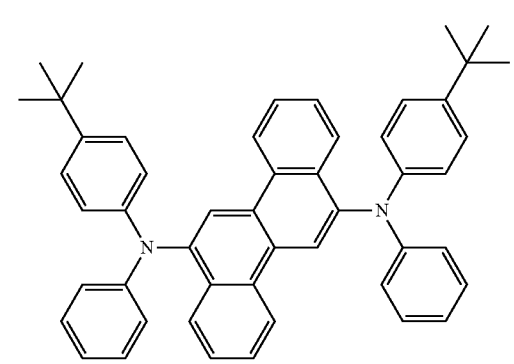
BD5
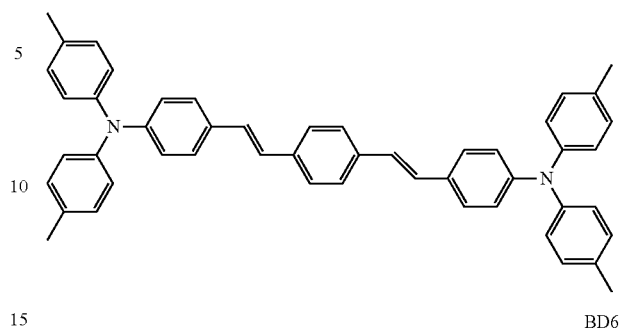
BD2
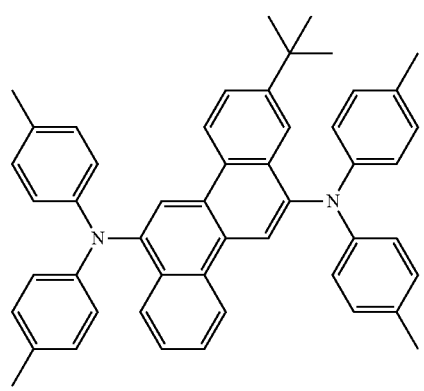
BD6
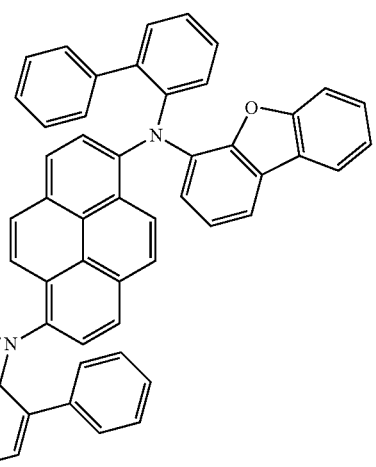
BD3
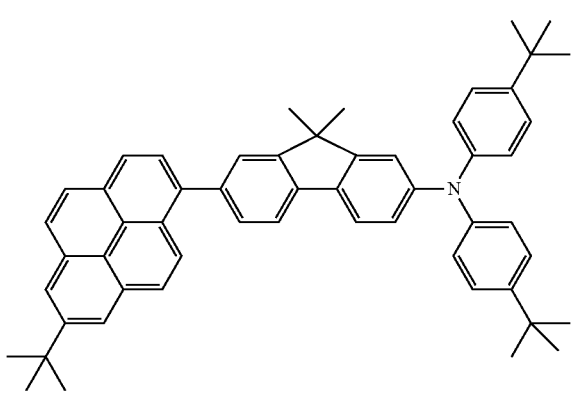
BD7
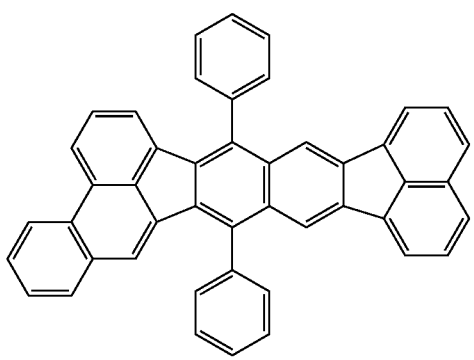
BD4
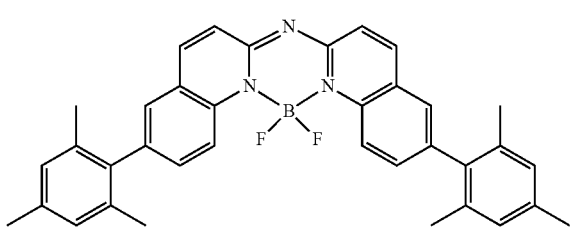
BD8
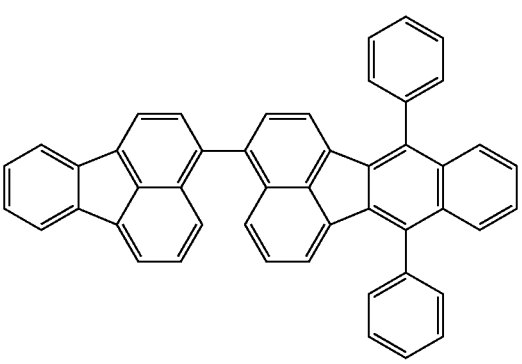

BD9
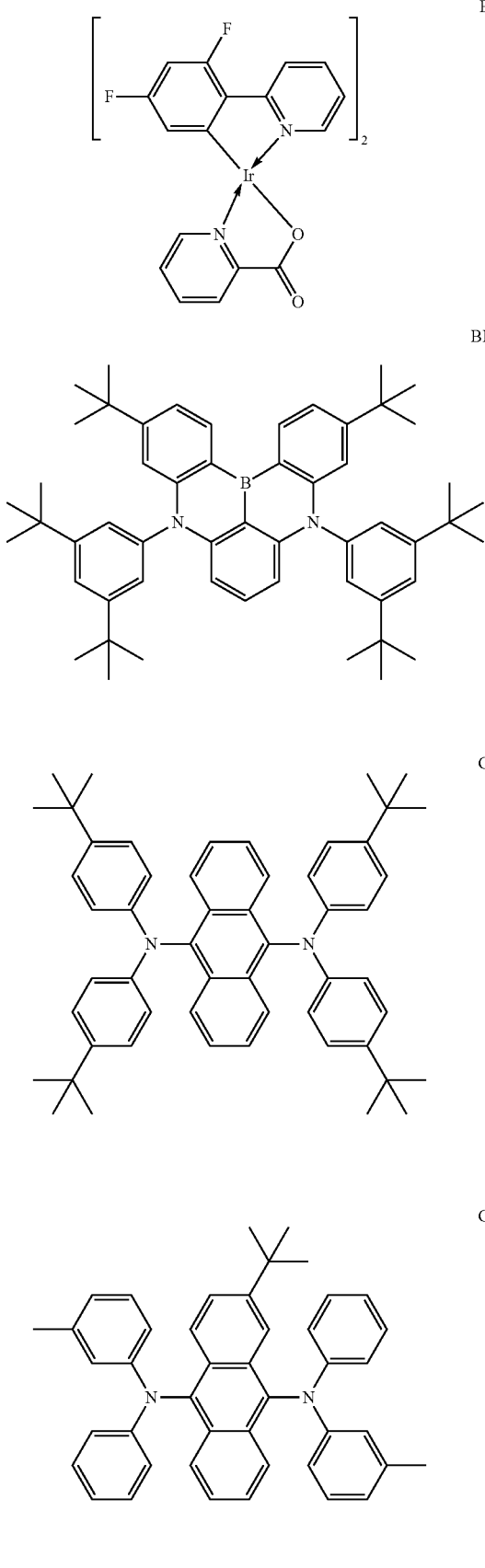
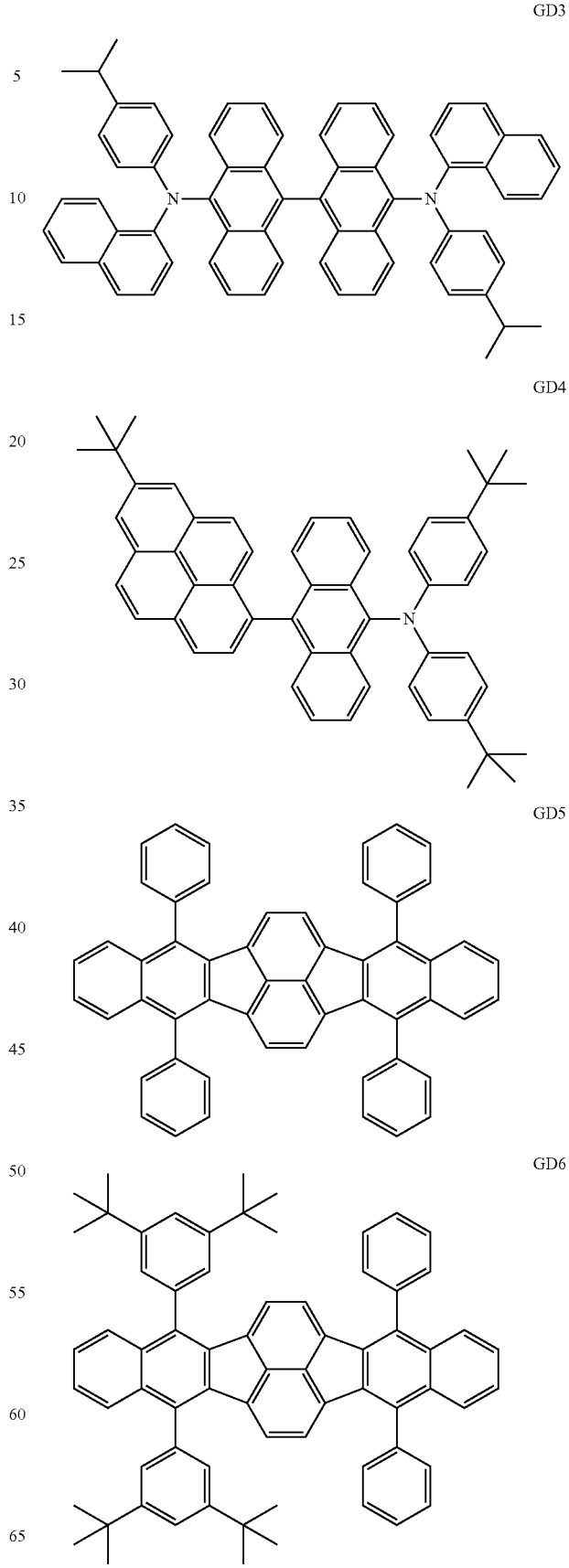

-continued
GD7
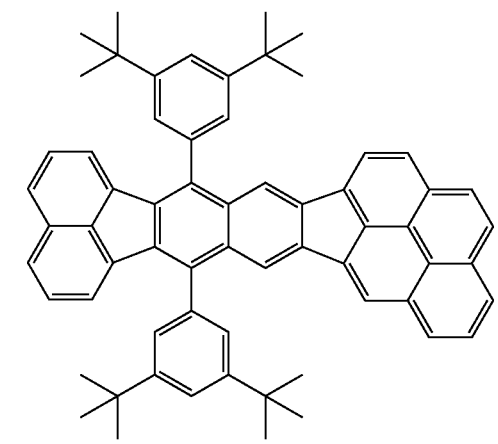
GD8
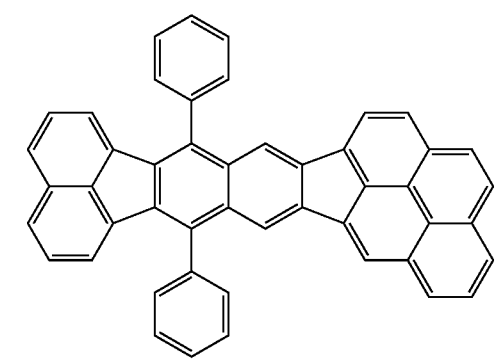
GD9
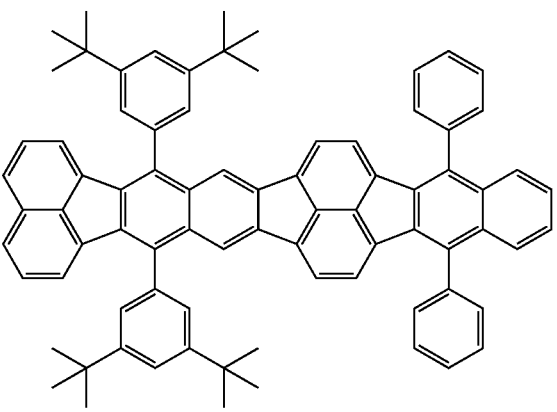
GD10
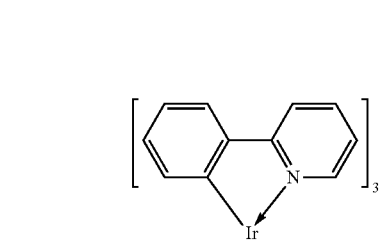
-continued
GD11
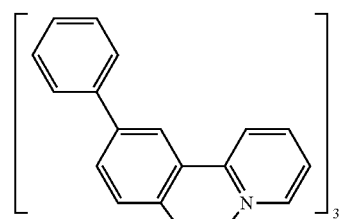
GD12
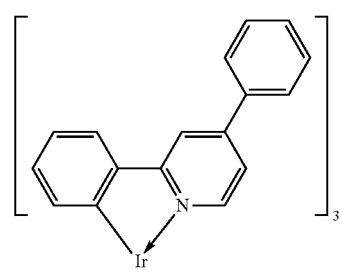
GD13
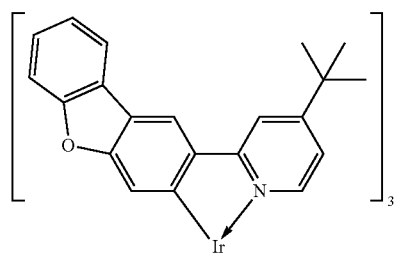
GD14
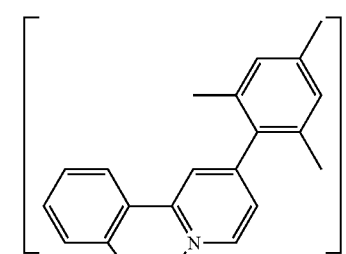
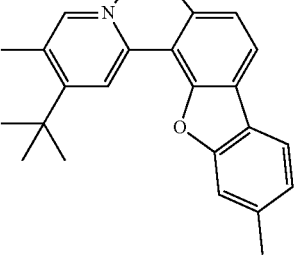

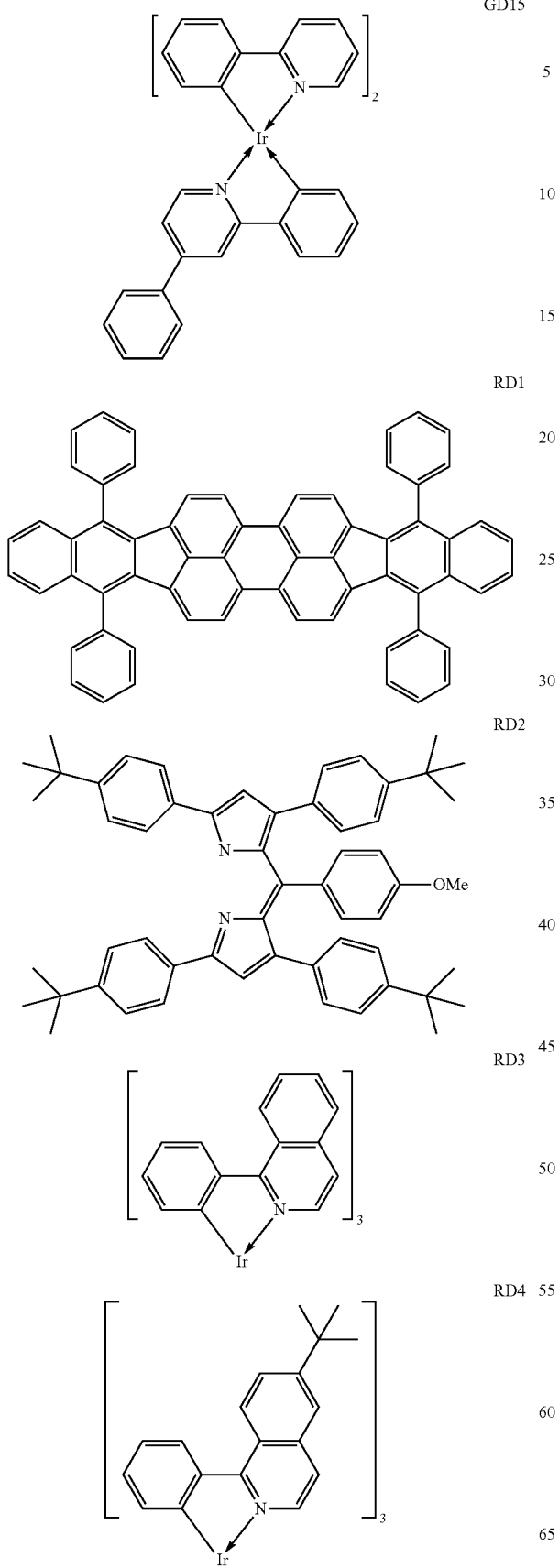
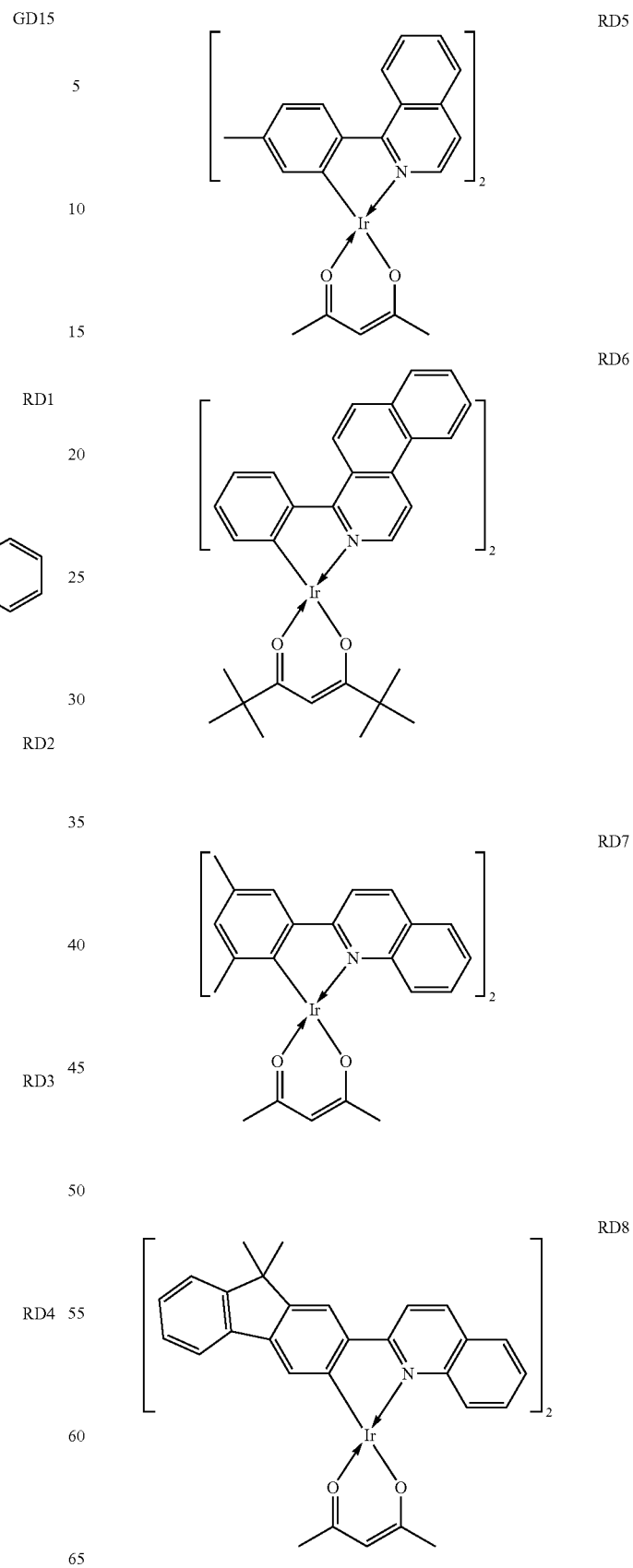

-continued

RD9
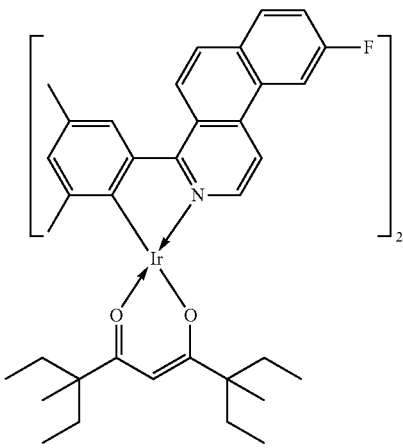

RD10
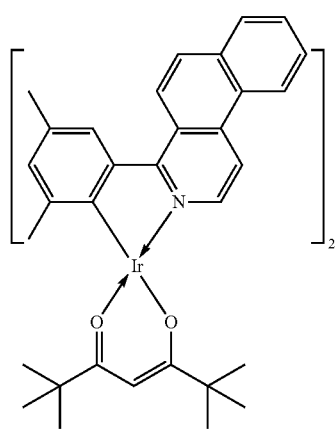

When the light-emitting material is a hydrocarbon compound, the material can prevent a decrease in luminous efficiency due to exciplex formation and a deterioration in color purity due to changes in the emission spectrum of the light-emitting material. The term "hydrocarbon compound" refers to a compound consisting of only carbon and hydrogen, and BD7, BD8, GD5 to GD9, and RD1 are hydrocarbon compounds. When the light-emitting material is a five-membered ring-containing fused polycyclic compound, the material has a high ionization potential and high resistance to oxidation. This can provide a highly durable device with a long lifetime. BD7, BD8, GD5 to GD9, and RD1 are five-membered ring-containing fused polycyclic compounds.

Examples of a host or an assist material in the light-emitting layer include aromatic hydrocarbon compounds and derivatives thereof, carbazole derivatives, dibenzofuran derivatives, dibenzothiophene derivatives, organoaluminum complexes, such as tris(8-quinolinolato)aluminum, and organoberyllium complexes. Non-limiting specific examples of a compound used as a host or an assist material in the light-emitting layer will be illustrated below.

EM1
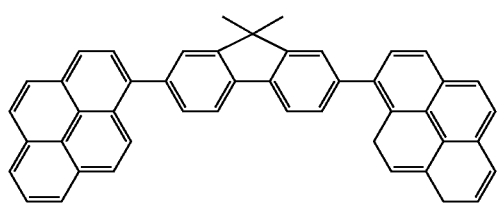

EM2
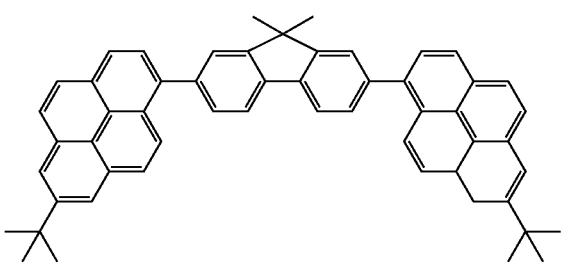

EM3
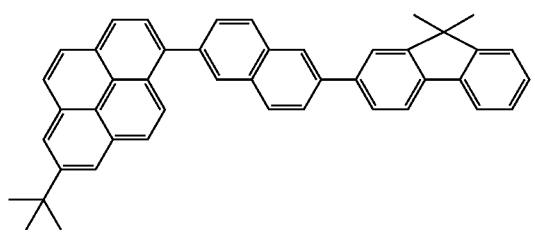

EM4
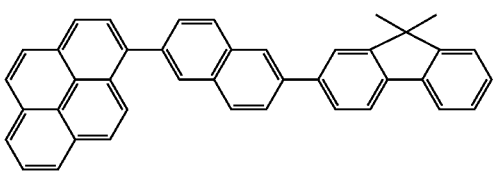

-continued
EM5                                                 EM6
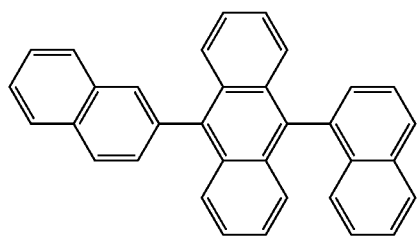 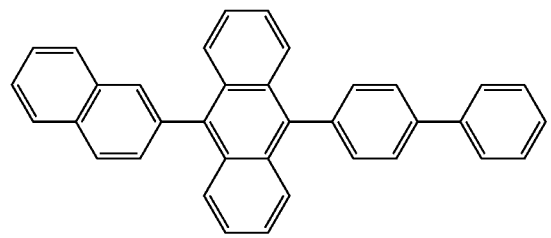
EM7                                                 EM8
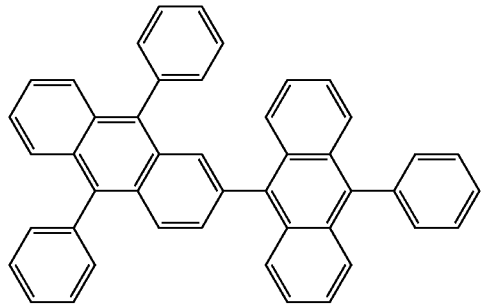 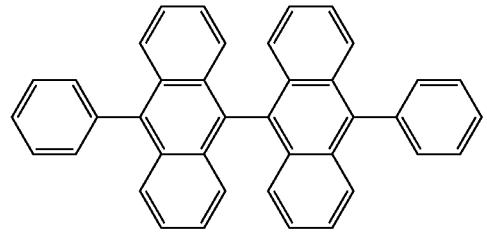
EM9                                                 EM10
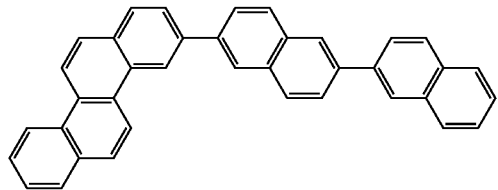 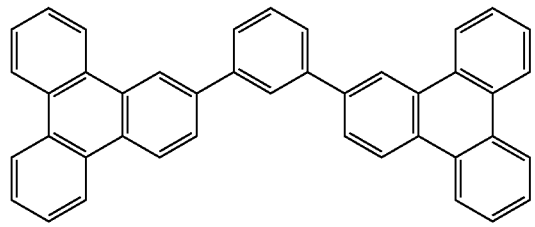
EM11                                                EM12
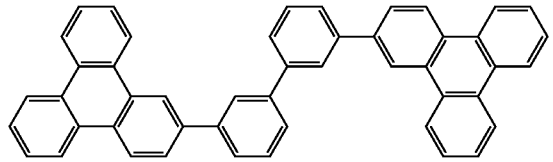 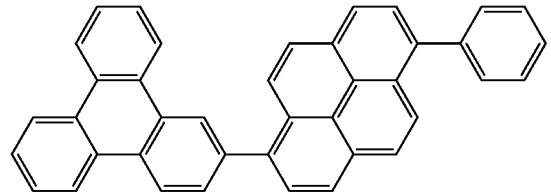
EM13                                                EM14
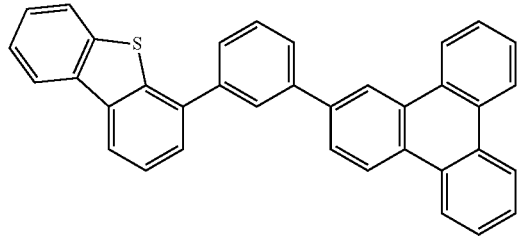 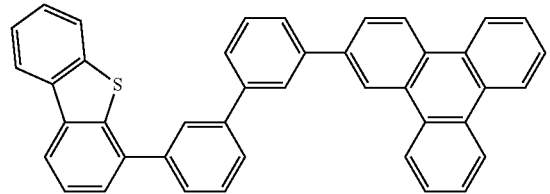
EM15
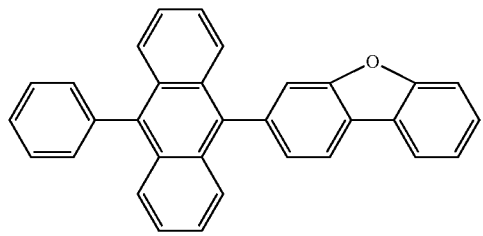

EM16
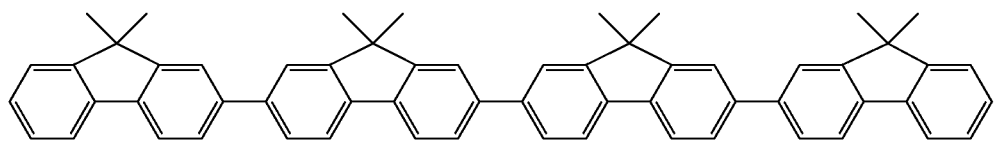
EM17
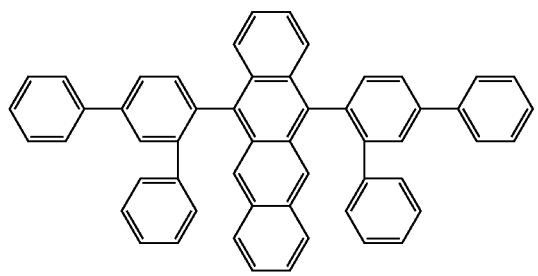
EM18
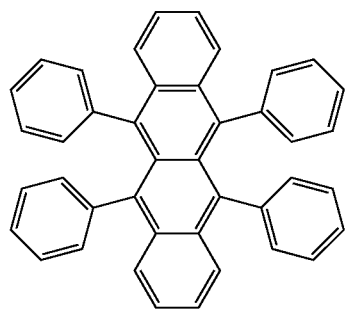
EM19
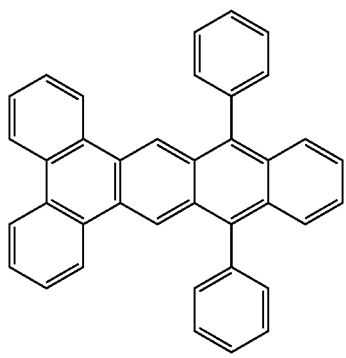
EM20
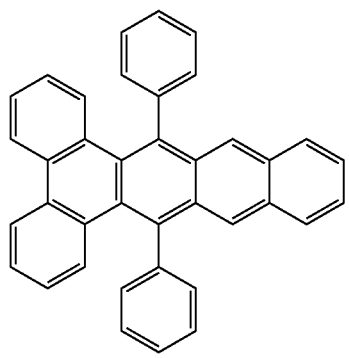
EM21
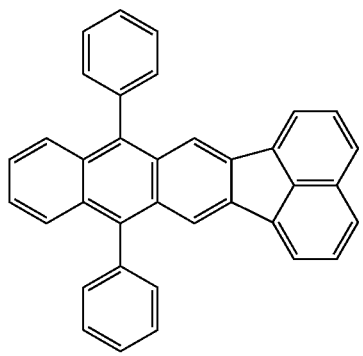
EM22
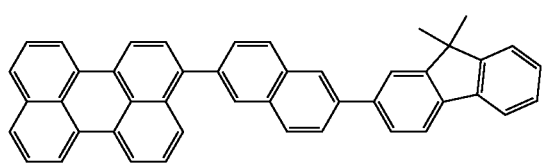
EM23
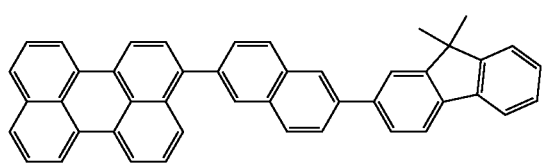
EM24
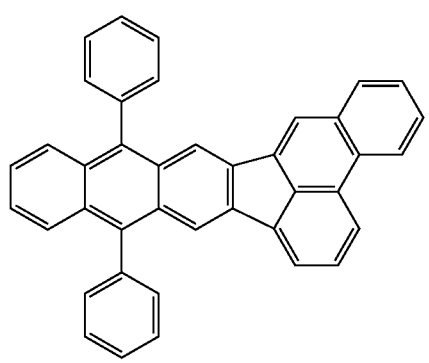

-continued
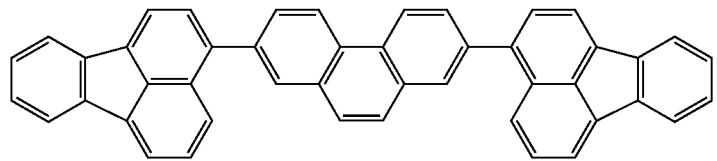
EM25
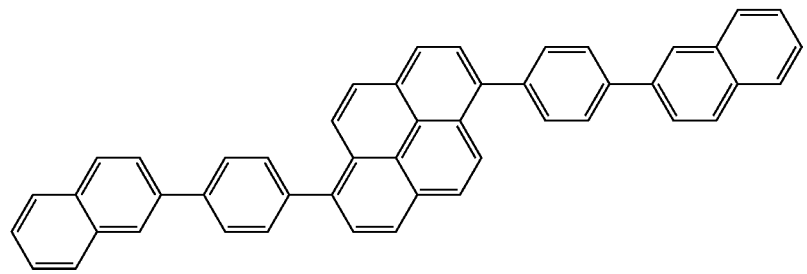
EM26
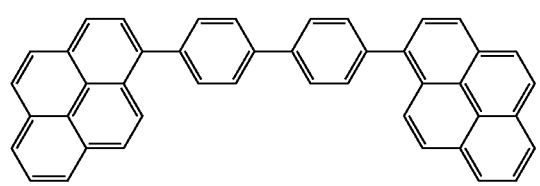
EM27
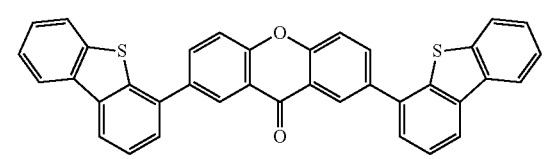
EM28
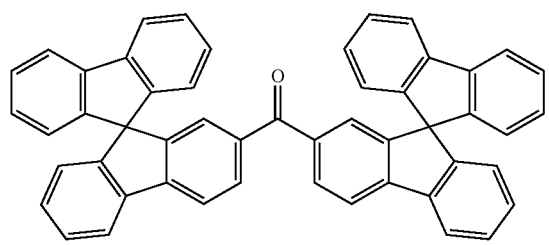
EM29
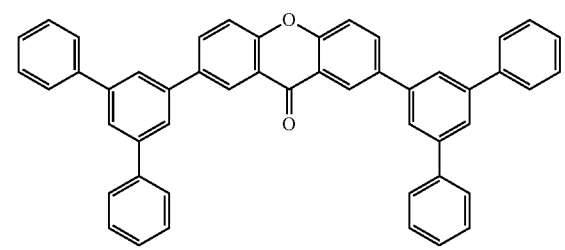
EM30
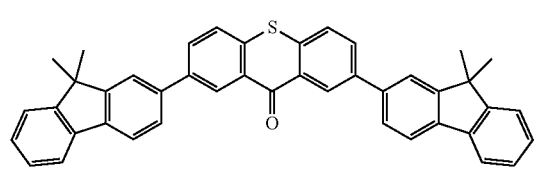
EM31
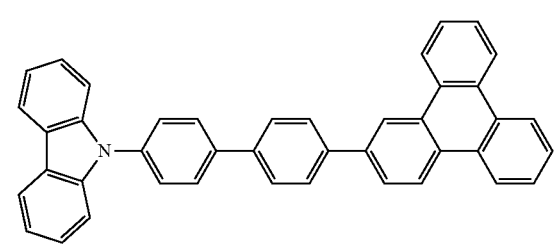
EM32
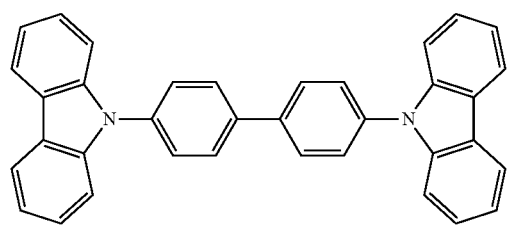
EM33
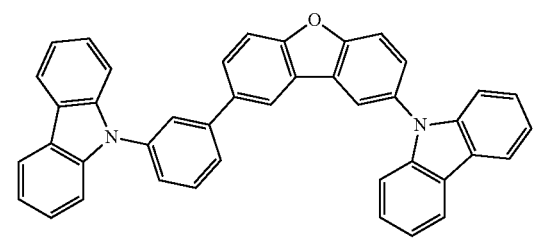
EM34

EM35
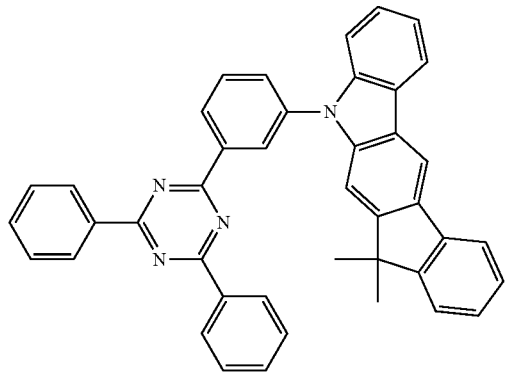

EM36
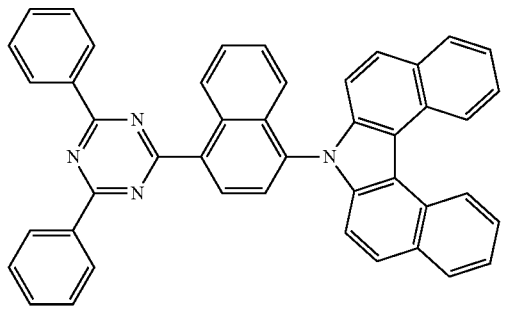

EM37
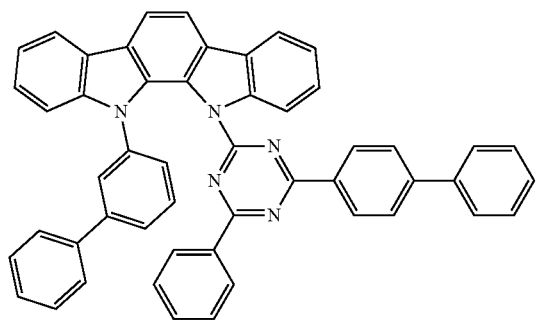

EM38
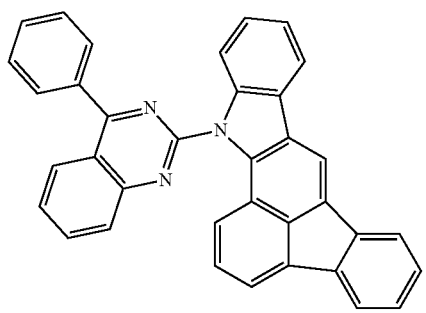

EM39
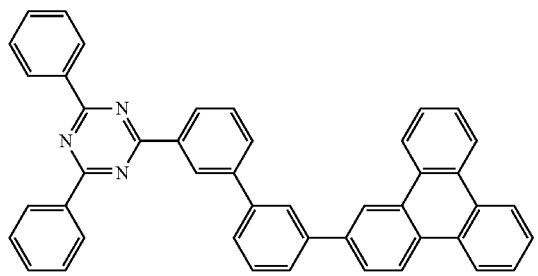

EM40
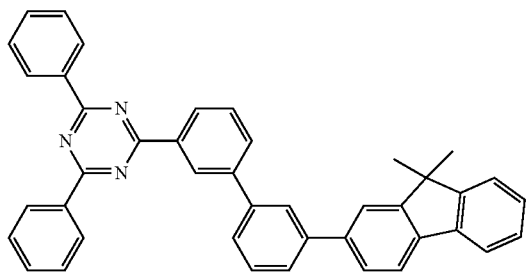

When the host material is a hydrocarbon compound, the compound according to the embodiment can easily trap electrons and holes to contribute to higher efficiency. The term "hydrocarbon compound" refers to a compound consisting of only carbon and hydrogen, and EM1 to EM12 and EM16 to EM27 are hydrocarbon compounds.

The electron transport material can be freely-selected from materials capable of transporting electrons injected from the cathode to the light-emitting layer and is selected in consideration of, for example, the balance with the hole mobility of the hole transport material. Examples of a material having the ability to transport electrons include oxadiazole derivatives, oxazole derivatives, pyrazine derivatives, triazole derivatives, triazine derivatives, quinoline derivatives, quinoxaline derivatives, phenanthroline derivatives, organoaluminum complexes, and condensed-ring compounds, such as fluorene derivatives, naphthalene derivatives, chrysene derivatives, and anthracene derivatives. The electron transport materials can be used for the hole-blocking layer. Non-limiting specific examples of a compound used as the electron transport material will be illustrated below.

ET1
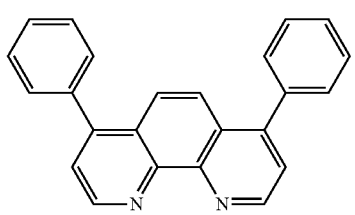

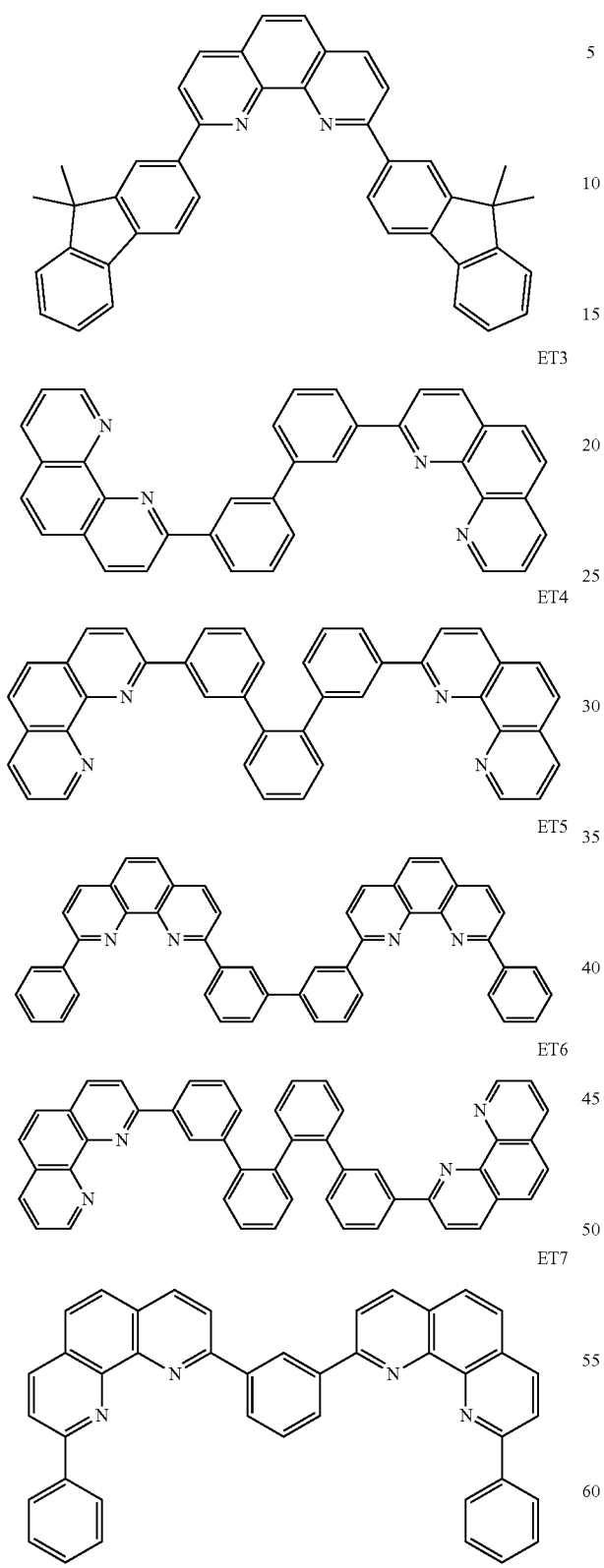
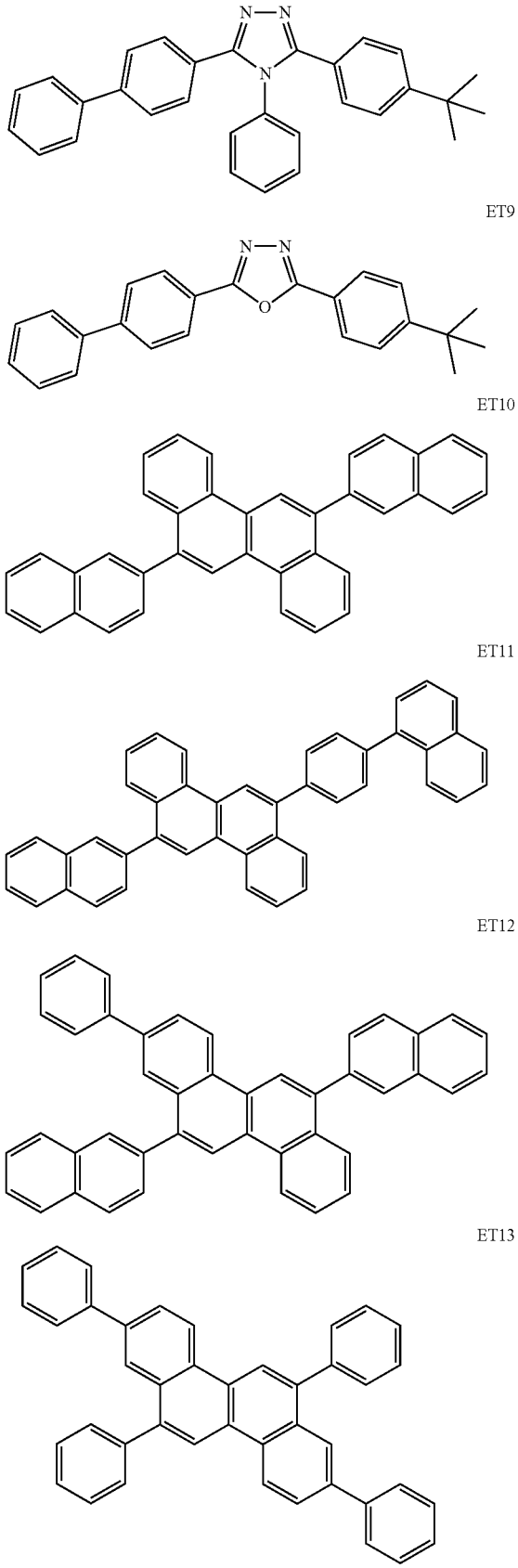

ET14
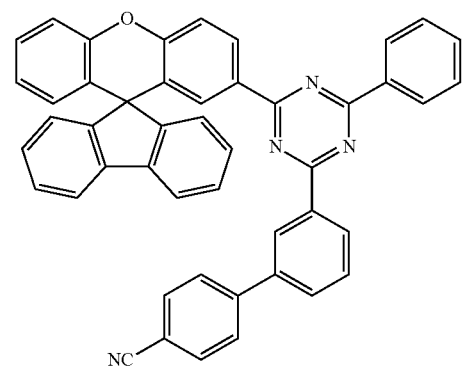
ET15
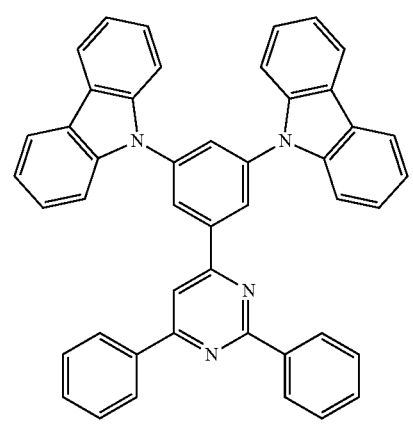
ET16
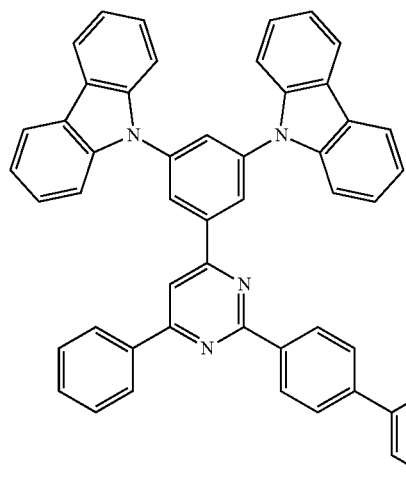
ET17
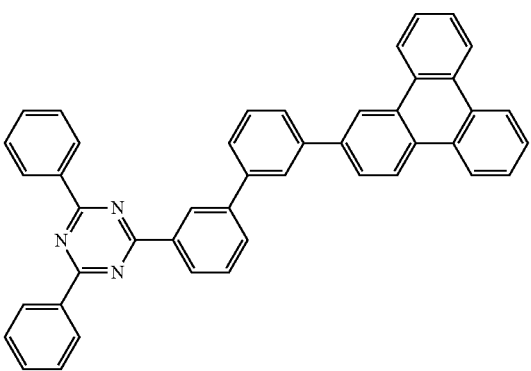
ET18
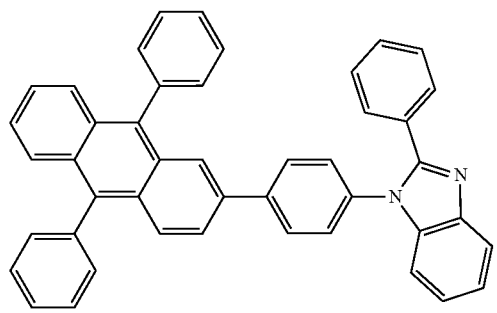
ET19
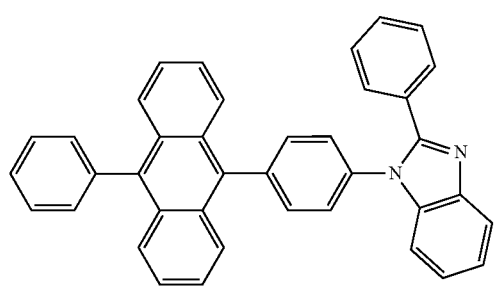
ET20
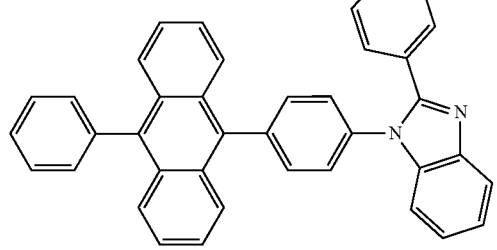
ET21
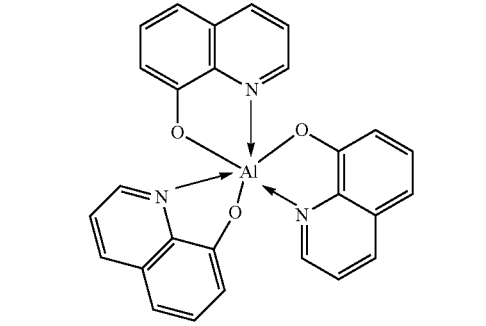
ET22
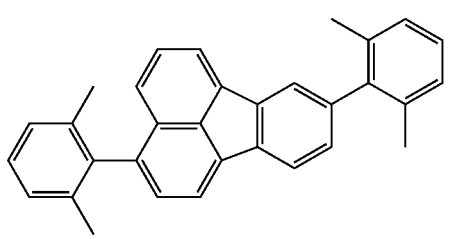

ET23

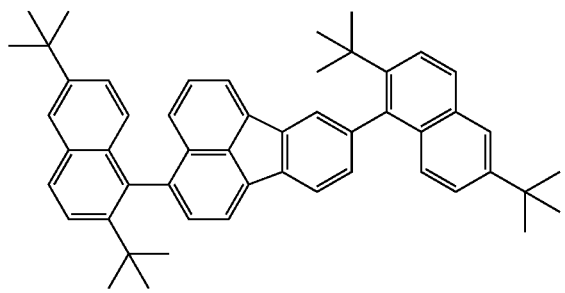

ET24

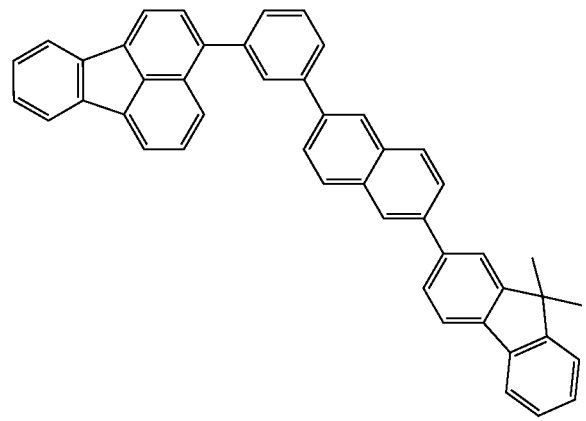

ET25

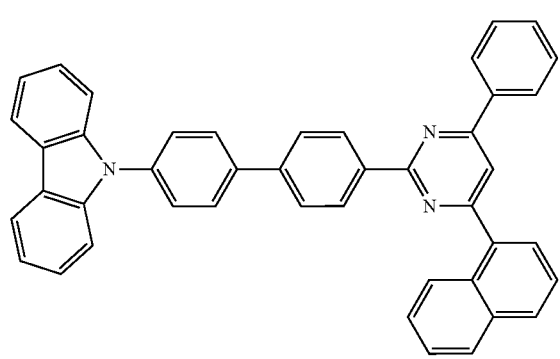

ET26

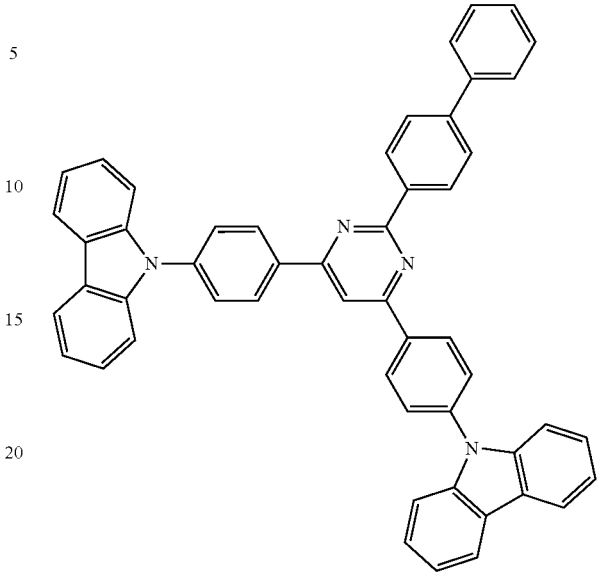

ET27

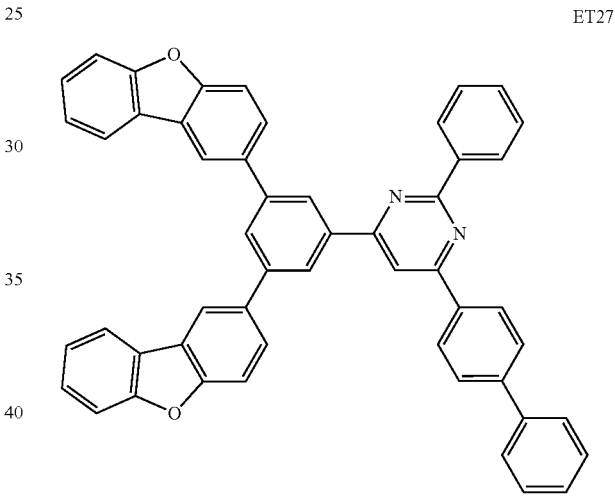

An electron injection material can be freely-selected from materials capable of easily injecting electrons from the cathode and is selected in consideration of, for example, the balance with the hole-injecting properties. As the organic compound, n-type dopants and reducing dopants are also included. Examples thereof include alkali metal-containing compounds, such as lithium fluoride, lithium complexes, such as lithium quinolinolate, benzimidazolidene derivatives, imidazolidene derivatives, fulvalene derivatives, and acridine derivatives.

Configuration of Organic Light-Emitting Device

The organic light-emitting device is provided by disposing an anode, the organic compound layer, and a cathode on a substrate. A protective layer, a color filter, and so forth may be disposed on the cathode. In the case of disposing the color filter, a planarization layer may be disposed between the protective layer and the color filter. The planarization layer can be composed of, for example, an acrylic resin.

Substrate

Examples of the substrate include silicon wafers, quartz substrates, glass substrates, resin substrates, and metal substrates. The substrate may include switching devices such as a transistor, a line, and an insulating layer thereon. As the insulating layer, any material can be used as long as a contact hole can be formed to establish the electrical connection between the anode and the line and as long as insulation with a non-connected line can be ensured. For example, a resin such as polyimide, silicon oxide, or silicon nitride can be used.

Electrode

A pair of electrodes can be used. The pair of electrodes may be an anode and a cathode. In the case where an electric field is applied in the direction in which the organic light-emitting device emits light, an electrode having a higher potential is the anode, and the other is the cathode. It can also be said that the electrode that supplies holes to the light-emitting layer is the anode and that the electrode that supplies electrons is the cathode.

As the constituent material of the anode, a material having a work function as high as possible can be used. Examples of the material that can be used include elemental metals, such as gold, platinum, silver, copper, nickel, palladium, cobalt, selenium, vanadium, and tungsten, mixtures thereof, alloys of combinations thereof, and metal oxides, such as tin oxide, zinc oxide, indium oxide, indium-tin oxide (ITO), and indium-zinc oxide. Additionally, conductive polymers, such as polyaniline, polypyrrole, and polythiophene, may be used.

These electrode materials may be used alone or in combination of two or more. The anode may be formed of a single layer or multiple layers.

In the case where the anode is used as a reflective electrode, for example, chromium, aluminum, silver, titanium, tungsten, molybdenum, an alloy thereof, or a stack thereof may be used. In the case where the anode is used as a transparent electrode, a transparent conductive oxide layer composed of, for example, indium-tin oxide (ITO) or indium-zinc oxide may be used; however, the anode is not limited thereto. The electrode may be formed by photolithography.

As the constituent material of the cathode, a material having a lower work function can be used. Examples thereof include elemental metals such as alkali metals, e.g., lithium, alkaline-earth metals, e.g., calcium, aluminum, titanium, manganese, silver, lead, and chromium, and mixtures thereof. Alloys of combinations of these elemental metals may also be used. For example, magnesium-silver, aluminum-lithium, aluminum-magnesium, silver-copper, and zinc-silver may be used. Metal oxides such as indium-tin oxide (ITO) may also be used. These electrode materials may be used alone or in combination of two or more. The cathode may have a single-layer structure or a multilayer structure. In particular, silver can be used. To reduce the aggregation of silver, a silver alloy can be used. Any alloy ratio may be used as long as the aggregation of silver can be reduced. For example, 1:1 may be used.

A top emission device may be provided using the cathode formed of a conductive oxide layer composed of, for example, ITO. A bottom emission device may be provided using the cathode formed of a reflective electrode composed of, for example, aluminum (Al). The cathode is not particularly limited. Any method for forming the cathode may be used. For example, a direct-current or alternating-current sputtering technique can be employed because good film coverage is obtained and thus the resistance is easily reduced.

Protective Layer

A protective layer may be disposed on the cathode. For example, a glass member provided with a moisture absorbent can be bonded to the cathode to reduce the entry of, for example, water into the organic compound layer, thereby suppressing the occurrence of display defects. In another embodiment, a passivation film composed of, for example, silicon nitride may be disposed on the cathode to reduce the entry of, for example, water into the organic compound layer. For example, after the formation of the cathode, the substrate may be transported to another chamber without breaking the vacuum, and a silicon nitride film having a thickness of 2 μm may be formed by a chemical vapor deposition (CVD) method to provide a protective layer. After the film deposition by the CVD method, a protective layer may be formed by an atomic layer deposition (ALD) method.

Color Filter

A color filter may be disposed on the protective layer. For example, a color filter may be disposed on another substrate in consideration of the size of the organic light-emitting device and bonded to the substrate provided with the organic light-emitting device. A color filter may be formed by patterning on the protective layer using photolithography. The color filter may be composed of a polymer.

Planarization Layer

A planarization layer may be disposed between the color filter and the protective layer. The planarization layer may be composed of an organic compound. A low- or high-molecular-weight organic compound may be used. A high-molecular-weight organic compound can be used.

The planarization layers may be disposed above and below (or on) the color filter and may be composed of the same or different materials. Specific examples thereof include poly(vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

Opposite Substrate

An opposite substrate may be disposed on the planarization layer. The opposite substrate is disposed at a position corresponding to the substrate described above and thus is called an opposite substrate. The opposite substrate may be composed of the same material as the substrate described above.

Organic Layer

The organic compound layer, such as the hole injection layer, the hole transport layer, the electron-blocking layer, the light-emitting layer, the hole-blocking layer, the electron transport layer, or the electron injection layer, included in the organic light-emitting device according to an embodiment of the present disclosure is formed by a method described below.

For the organic compound layer included in the organic light-emitting device according to an embodiment of the present disclosure, a dry process, such as a vacuum evaporation method, an ionized evaporation method, sputtering, or plasma, may be employed. Alternatively, instead of the dry process, it is also possible to employ a wet process in which a material is dissolved in an appropriate solvent and then a film is formed by a known coating method, such as spin coating, dipping, a casting method, a Langmuir-Blodgett (LB) technique, or an ink jet method.

In the case where the layer is formed by, for example, the vacuum evaporation method or the solution coating method, crystallization and so forth are less likely to occur, and good stability with time is obtained. In the case of forming a film by the coating method, the film may be formed in combination with an appropriate binder resin.

Non-limiting examples of the binder resin include poly(vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

These binder resins may be used alone as a homopolymer or copolymer or in combination as a mixture of two or more. Furthermore, additives, such as a known plasticizer, antioxidant, and ultraviolet absorber, may be used, as needed.

Application of Organic Light-Emitting Device According to Embodiment of the Present Disclosure The organic light-emitting device according to an embodiment of the present disclosure can be used as component member of a display apparatus or a lighting device. Other applications include exposure light sources for electrophotographic image-forming apparatuses, backlights for liquid crystal displays, and light-emitting devices including white light sources and color filters.

The display apparatus may be an image information-processing unit having an image input unit that receives image information from an area or linear CCD sensor, a memory card, or any other source, an information-processing unit that processes the input information, and a display unit that displays the input image. The display apparatus includes multiple pixels, and at least one of the multiple pixels may include the organic light-emitting device according to the embodiment and a transistor coupled to the organic light-emitting device.

The display unit of an image pickup apparatus or an inkjet printer may have a touch panel function. The driving mode of the touch panel function may be, but is not limited to, an infrared mode, an electrostatic capacitance mode, a resistive film mode, or an electromagnetic inductive mode. The display apparatus may also be used for a display unit of a multifunction printer.

Figure 2:
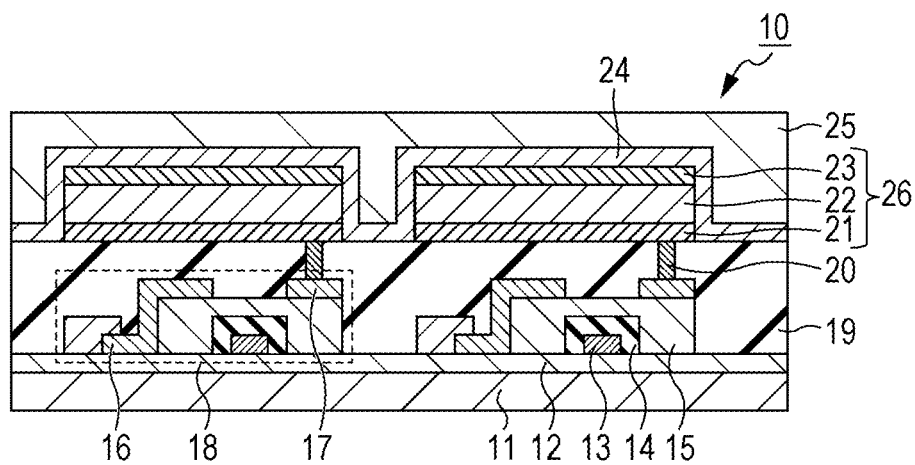
FIG. 2 is a schematic cross-sectional view of an example of a display apparatus including organic light-emitting devices according to an embodiment of the present disclosure.

The following describes a display apparatus according to the embodiment with reference to the attached drawings. FIG. 2 is a schematic cross-sectional view of an example of a display apparatus including organic light-emitting devices and thin-film transistor (TFT) devices coupled to the respective organic light-emitting devices. Each of the TFT devices is an example of active devices.

A display apparatus 10 illustrated in FIG. 2 includes a substrate 11 composed of, for example, glass and a moisture-proof film 12 disposed thereon, the moisture-proof film 12 being configured to protect the TFT devices or the organic compound layers. Reference numeral 13 denotes a gate electrode composed of a metal. Reference numeral 14 denotes a gate insulating film. Reference numeral 15 denotes a semiconductor layer.

TFT devices 18 each include the semiconductor layer 15, a drain electrode 16, and a source electrode 17. An insulating film 19 is disposed on the TFT devices 18. An anode 21 included in an organic light-emitting device 26 is coupled to the source electrode 17 through a contact hole 20.

The way of electric coupling between the electrodes (the anode 21 and a cathode 23) included in each of the organic light-emitting devices 26 and the electrodes (the source electrode 17 and the drain electrode 16) included in a corresponding one of the TFT devices 18 is not limited to the configuration illustrated in FIG. 2. It is sufficient that one of the anode 21 and the cathode 23 is electrically coupled to one of the source electrode 17 and the drain electrode 16 of the TFT device 18.

In the display apparatus 10 illustrated in FIG. 2, each organic compound layer 22 is illustrated as a single layer; however, the organic compound layer 22 may be formed of multiple layers. A first protective layer 24 and a second protective layer 25 are disposed on the cathodes 23 in order to reduce the deterioration of the organic light-emitting devices 26.

In the display apparatus 10 illustrated in FIG. 2, the transistors are used as switching devices; however, metal-insulator-metal (MIM) devices may be used as switching devices.

The transistors used in the display apparatus 10 illustrated in FIG. 2 are not limited to transistors formed using a single-crystal silicon wafer and may be thin-film transistors each having an active layer on the insulating surface of a substrate. Examples of the material of the active layer include single-crystal silicon, non-single-crystal silicon materials, such as amorphous silicon and microcrystalline silicon, and non-single-crystal oxide semiconductors, such as indium-zinc oxide and indium-gallium-zinc oxide. Thin-film transistors are also referred to as TFT devices.

The transistors in the display apparatus 10 illustrated in FIG. 2 may be formed in the substrate such as a Si substrate. The expression "formed in the substrate" indicates that the transistors are produced by processing the substrate such as a Si substrate. In the case where the transistors are formed in the substrate, the substrate and the transistors can be deemed to be integrally formed.

In the organic light-emitting device according to the embodiment, the luminance is controlled by the TFT devices, which are an example of switching devices; thus, an image can be displayed at respective luminance levels by arranging multiple organic light-emitting devices in the plane. The switching devices according to the embodiment are not limited to the TFT devices and may be low-temperature polysilicon transistors or active-matrix drivers formed on a substrate such as a Si substrate. The expression "on a substrate" can also be said to be "in the substrate". Whether transistors are formed in the substrate or TFT devices are used is selected in accordance with the size of a display unit. For example, in the case where the display unit has a size of about 0.5 inches, organic light-emitting devices can be disposed on a Si substrate.

Figure 3:
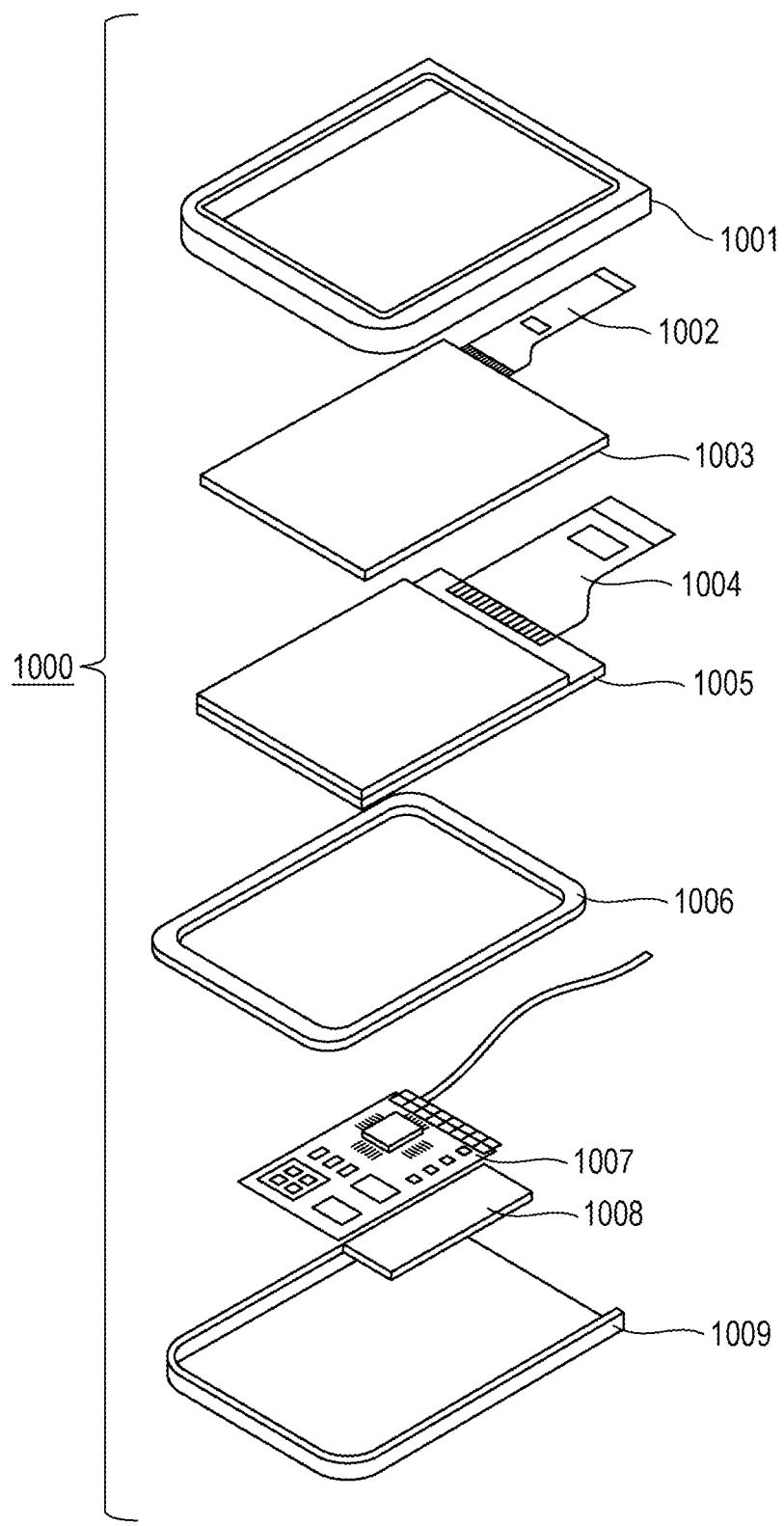
FIG. 3 is a schematic view of an example of a display apparatus according to an embodiment of the present disclosure.

FIG. 3 is a schematic view illustrating an example of a display apparatus according to the embodiment. A display apparatus 1000 may include a touch panel 1003, a display panel 1005, a frame 1006, a circuit substrate 1007, and a battery 1008 disposed between an upper cover 1001 and a lower cover 1009. The touch panel 1003 and the display panel 1005 are coupled to flexible printed circuits FPCs 1002 and 1004, respectively. The circuit substrate 1007 includes printed transistors. The battery 1008 need not be provided unless the display apparatus is a portable apparatus. The battery 1008 may be disposed at a different position even if the display apparatus is a portable apparatus.

The display apparatus according to the embodiment may be used for a display unit of a photoelectric conversion apparatus, such as an image pickup apparatus including an optical unit including multiple lenses and an image pickup device that receives light passing through the optical unit. The image pickup apparatus may include a display unit that displays information acquired by the image pickup device. The display unit may be a display unit exposed to the outside of the image pickup apparatus or a display unit disposed in a finder. The image pickup apparatus may be a digital camera or a digital camcorder.

Figure 4A:
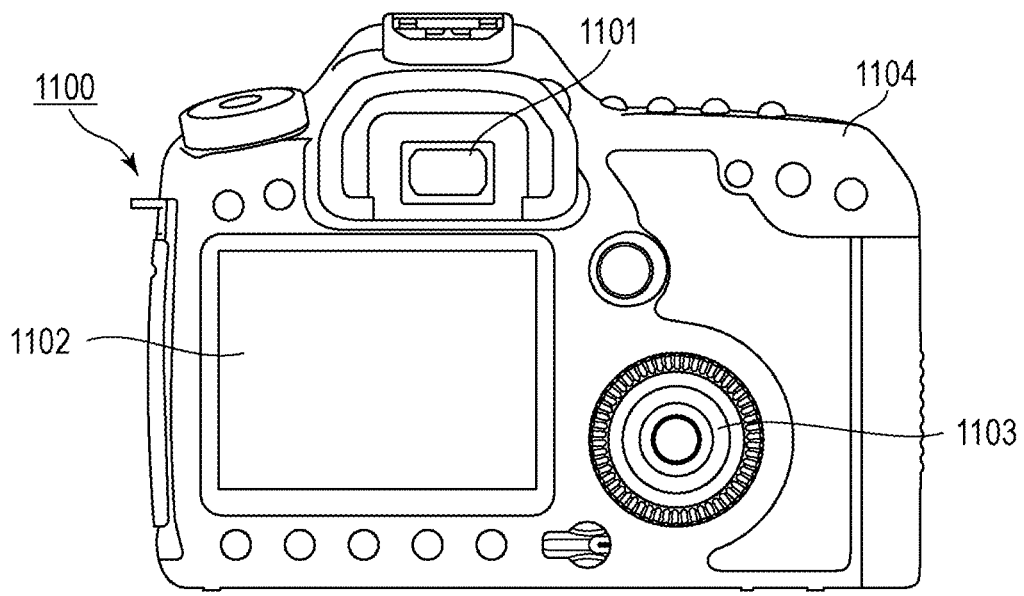
FIG. 4A is a schematic view of an example of an image pickup apparatus according to an embodiment of the present disclosure.

FIG. 4A is a schematic view illustrating an example of an image pickup apparatus according to the embodiment. An image pickup apparatus 1100 may include a viewfinder 1101, a rear display 1102, an operation unit 1103, and a housing 1104. The viewfinder 1101 may include the display apparatus according to the embodiment. In this case, the display apparatus may display environmental information, imaging instructions, and so forth in addition to an image to be captured. The environmental information may include, for example, the intensity of external light, the direction of the external light, the moving speed of a subject, and the possibility that a subject is shielded by a shielding material.

The timing suitable for imaging is only for a short time; thus, the information may be displayed as soon as possible. Accordingly, the display apparatus including the organic light-emitting device according to the embodiment can be used because of its short response time. The display apparatus including the organic light-emitting device can be used more suitably than liquid crystal displays for these units required to have a high display speed.

The image pickup apparatus 1100 includes an optical unit (not illustrated). The optical unit includes multiple lenses and is configured to form an image on an image pickup device in the housing 1104. The relative positions of the multiple lenses can be adjusted to adjust the focal point. This operation can also be performed automatically.

The display apparatus according to the embodiment may include a color filter having red, green, and blue portions. In the color filter, the red, green, and blue portions may be arranged in a delta arrangement.

A display apparatus according to the embodiment may be used for a display unit of an electronic apparatus, such as a portable terminal. In that case, the display apparatus may have both a display function and an operation function. Examples of the portable terminal include cellular phones, such as smartphones, tablets, and head-mounted displays.

Figure 4B:
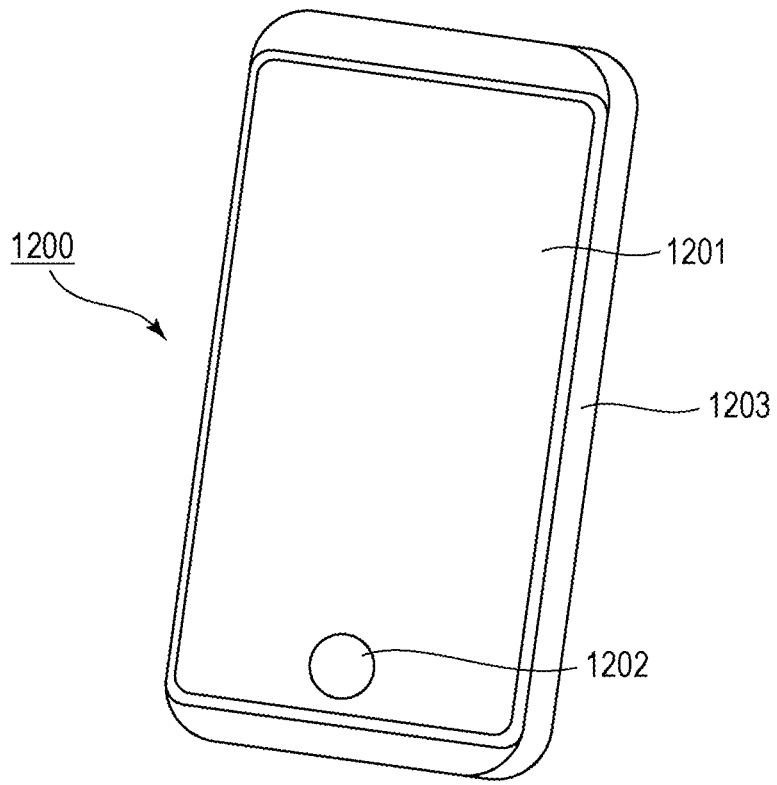
FIG. 4B is a schematic view of an example of an electronic apparatus according to an embodiment of the present disclosure.

FIG. 4B is a schematic view illustrating an example of an electronic apparatus according to the embodiment. An electronic apparatus 1200 includes a display unit 1201, an operation unit 1202, and a housing 1203. The housing 1203 may accommodate a circuit, a printed circuit board including the circuit, a battery, and a communication unit. The operation unit 1202 may be a button or a touch-panel-type reactive unit. The operation unit may be a biometric recognition unit that recognizes a fingerprint to release the lock or the like. An electronic apparatus having a communication unit can also be referred to as a communication apparatus.

Figure 5A:
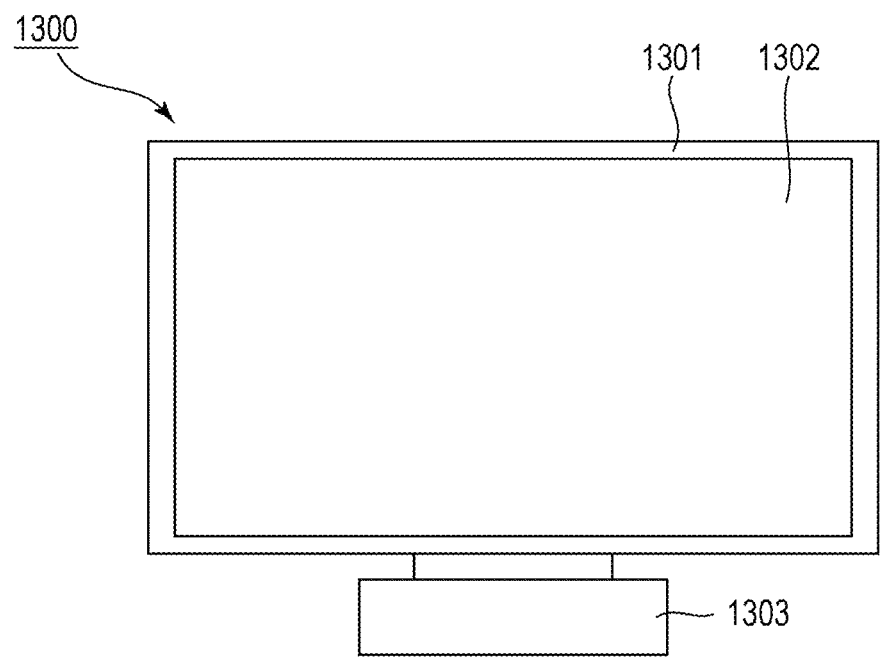
FIG. 5A is a schematic view of an example of a display apparatus according to an embodiment of the present disclosure.
Figure 5B:
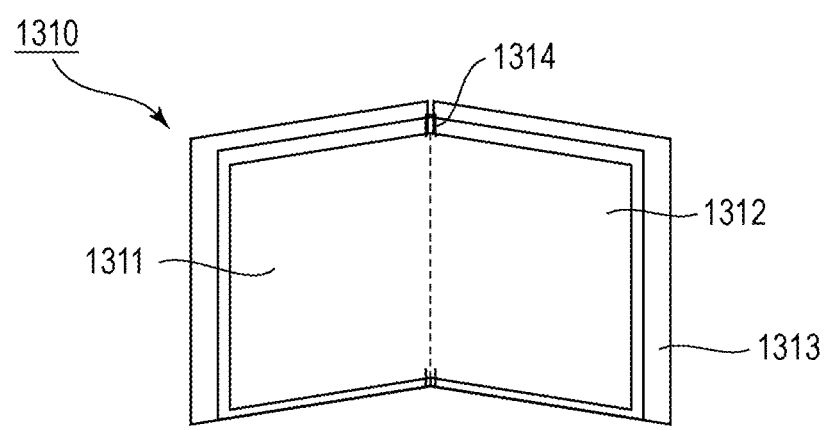
FIG. 5B is a schematic view of an example of a foldable display apparatus according to an embodiment of the present disclosure.

FIGS. 5A and 5B are schematic views illustrating examples of a display apparatus according to the embodiment. FIG. 5A illustrates a display apparatus, such as a television monitor or a personal computer monitor. A display apparatus 1300 includes a frame 1301 and a display unit 1302. The display unit 1302 may include an organic electroluminescent element according to the embodiment. The display device 1300 also includes a base 1303 that supports the frame 1301 and the display unit 1302. The base 1303 is not limited to a form illustrated in FIG. 5A. The lower side of the frame 1301 may also serve as a base. The frame 1301 and the display unit 1302 may be curved and may have a radius of curvature of 5,000 mm or more and 6,000 mm or less.

FIG. 5B is a schematic view illustrating another example of a display apparatus according to the embodiment. A display apparatus 1310 illustrated in FIG. 5B can be folded and is what is called a foldable display apparatus. The display apparatus 1310 includes a first display portion 1311, a second display portion 1312, a housing 1313, and an inflection point 1314. The first display portion 1311 and the second display portion 1312 may include a light-emitting device according to the embodiment. The first display portion 1311 and the second display portion 1312 may be a single, seamless display apparatus. The first display portion 1311 and the second display portion 1312 can be divided from each other at the inflection point. The first display portion 1311 and the second display portion 1312 may display different images from each other. Alternatively, a single image may be displayed in the first and second display portions.

Figure 6A:
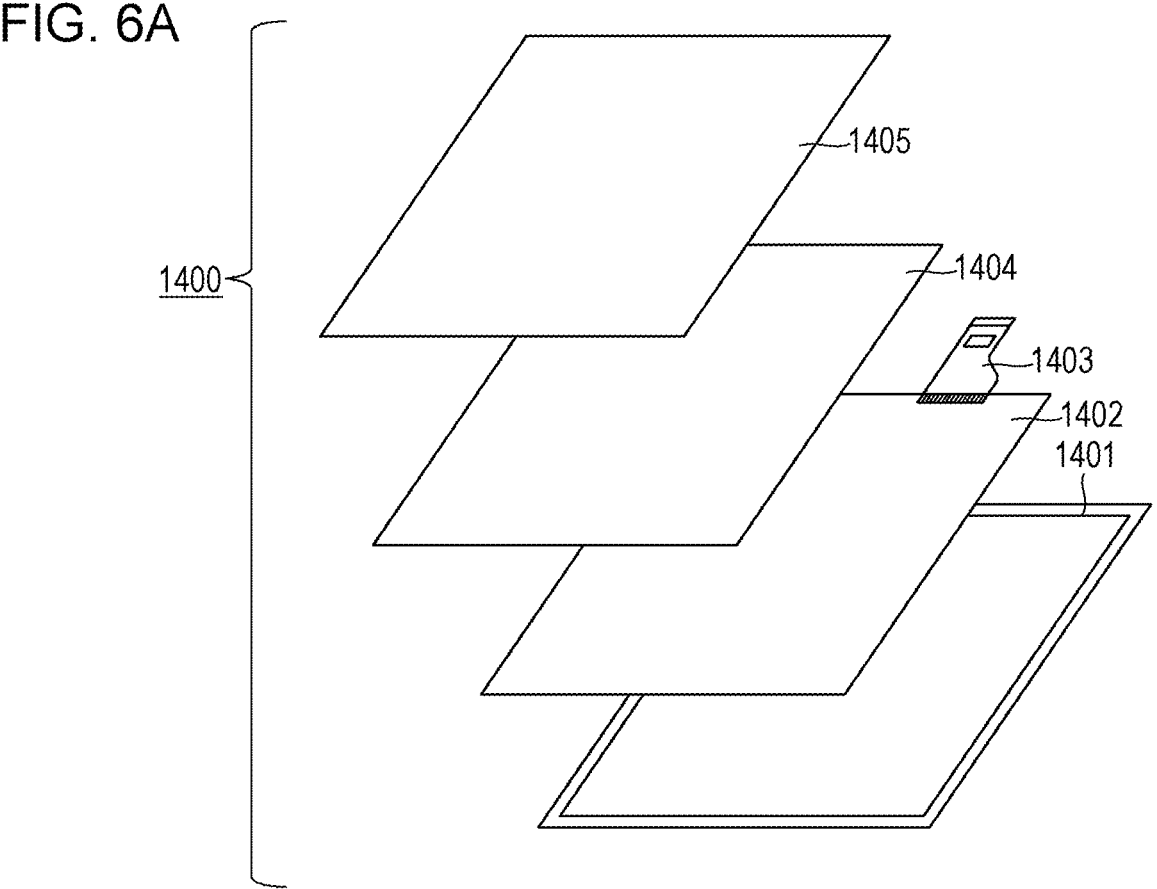
FIG. 6A is a schematic view of an example of a lighting device according to an embodiment of the present disclosure.

FIG. 6A is a schematic view illustrating an example of a lighting device according to the embodiment. A lighting device 1400 may include a housing 1401, a light source 1402, a circuit board 1403, an optical filter 1404 that transmits light emitted from the light source 1402, and a light diffusion unit 1405. The light source 1402 may include an organic light-emitting device according to the embodiment. The optical filter 1404 may be a filter that improves the color rendering properties of the light source. The light diffusion unit 1405 can effectively diffuse light from the light source to deliver the light to a wide range when used for illumination and so forth. The optical filter 1404 and the light diffusion unit 1405 may be disposed at the light emission side of the lighting device. A cover may be disposed at the outermost portion, as needed.

The lighting device is, for example, a device that lights a room. The lighting device may emit light of white, neutral white, or any color from blue to red. A light control circuit that controls the light may be provided. The lighting device may include the organic light-emitting device according to the embodiment and a power supply circuit coupled thereto. The power supply circuit is a circuit that converts an AC voltage into a DC voltage. The color temperature of white is 4,200 K, and the color temperature of neutral white is 5,000 K. The lighting device may include a color filter.

The lighting device according to the embodiment may include a heat dissipation unit. The heat dissipation unit is configured to release heat in the device to the outside of the device and is composed of, for example, a metal having a high specific heat and liquid silicone.

Figure 6B:
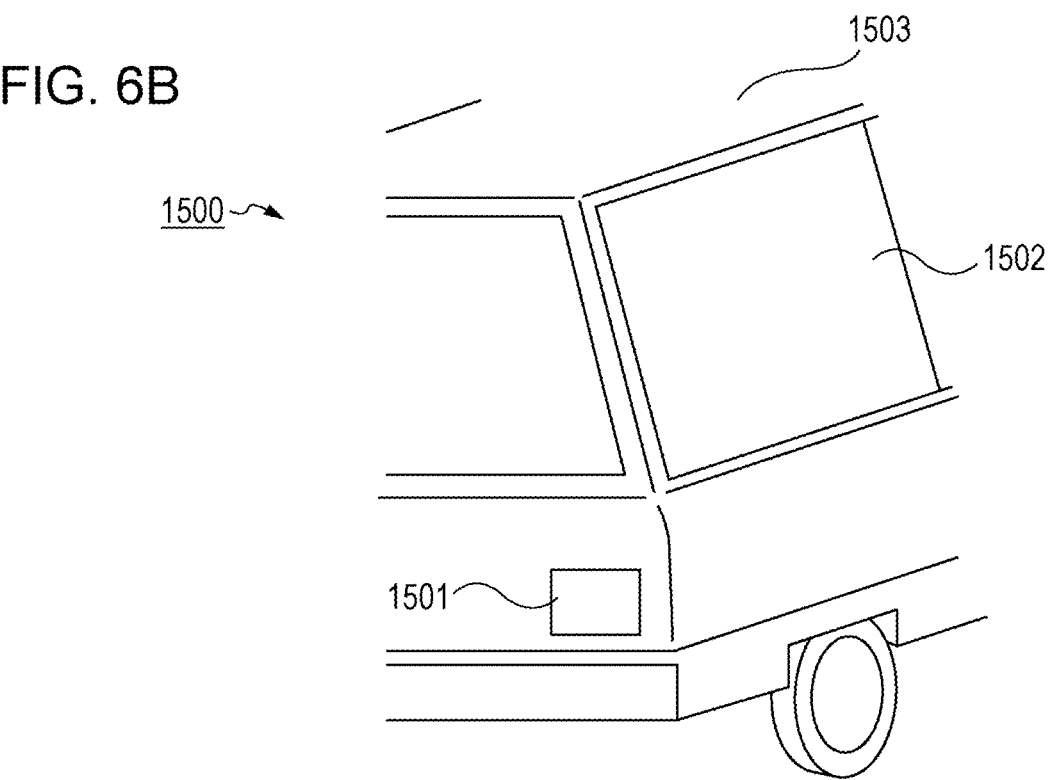
FIG. 6B is a schematic view of an example of an automobile including an automotive lighting unit according to an embodiment of the present disclosure.

FIG. 6B is a schematic view illustrating an automobile as an example of a moving object. The automobile includes a tail lamp, which is an example of lighting units. An automobile 1500 includes a tail lamp 1501 and may be configured to light the tail lamp when a brake operation or the like is performed.

The tail lamp 1501 may include an organic light-emitting device according to the embodiment. The tail lamp 1501 may include a protective member that protects the organic light-emitting device. The protective member may be composed of any transparent material having high strength to some extent and can be composed of, for example, polycarbonate. The polycarbonate may be mixed with, for example, a furandicarboxylic acid derivative or an acrylonitrile derivative.

The automobile 1500 may include an automobile body 1503 and windows 1502 attached thereto. The windows 1502 may be transparent displays if the windows are not used to check the front and back of the automobile. The transparent displays may include an organic light-emitting device according to the embodiment. In this case, the components, such as the electrodes, of the organic light-emitting device are formed of transparent members.

The moving object according to the embodiment may be, for example, a ship, an aircraft, or a drone. The moving object may include a body and a lighting unit attached to the body. The lighting unit may emit light to indicate the position of the body. The lighting unit includes the organic light-emitting device according to the embodiment.

Figure 7:
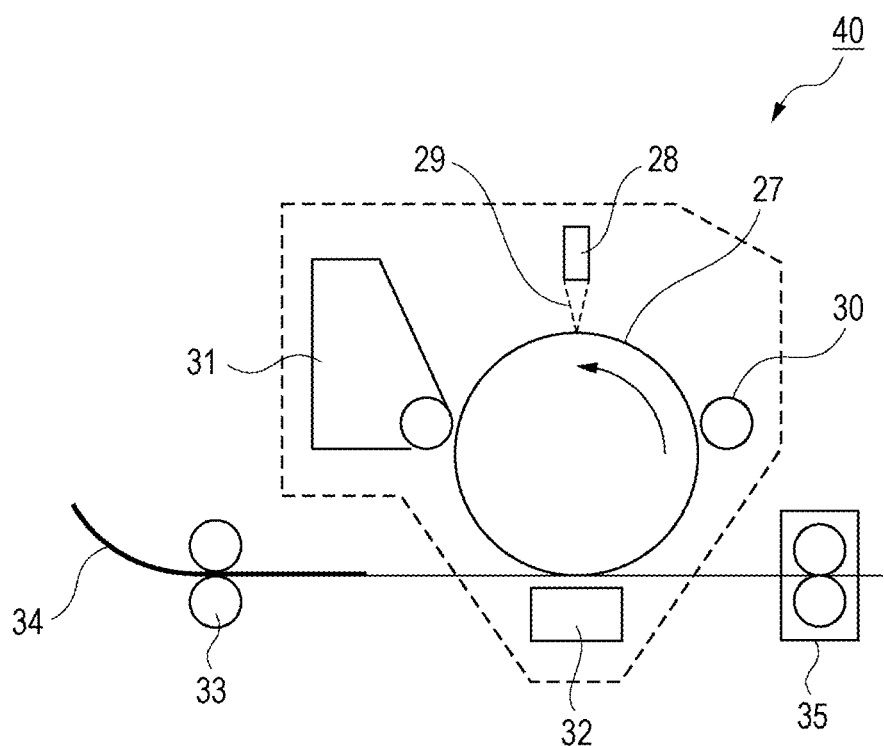
FIG. 7 is a schematic view of an example of an image-forming apparatus according to an embodiment of the present disclosure.

FIG. 7 is a schematic view of an example of an image-forming apparatus. An image-forming apparatus 40 is an electrophotographic image-forming apparatus and includes a photoconductor 27, an exposure light source 28, a charging unit 30, a developing unit 31, a transfer unit 32, a transport roller 33, and a fusing unit 35. Light 29 is emitted from the exposure light source 28 and forms an electrostatic latent image on the surface of the photoconductor 27. The exposure light source 28 includes the organic light-emitting device according to the embodiment. The developing unit 31 contains, for example, a toner. The charging unit 30 charges the photoconductor 27. The transfer unit 32 transfers the developed image to a recording medium 34. The transport roller 33 transports the recording medium 34. The recording medium 34 is paper, for example. The fusing unit 35 fixes the image formed on the recording medium 34.

FIGS. 8A and 8B each illustrate the exposure light source 28 and are each a schematic view illustrating multiple light-emitting portions 36 arranged on a long substrate. Arrows 37 each represent the row direction in which the organic light-emitting devices are arranged. The row direction is the same as the direction of the axis on which the photoconductor 27 rotates. This direction can also be referred to as the long-axis direction of the photoconductor 27. FIG. 8A illustrates a configuration in which the light-emitting portions 36 are arranged in the long-axis direction of the photoconductor 27. FIG. 8B is different from FIG. 8A in that the light-emitting portions 36 are arranged alternately in the row direction in a first row and a second row. The first row and the second row are located at different positions in the column direction. In the first row, the multiple light-emitting portions 36 are spaced apart. The second row has the light-emitting portions 36 at positions corresponding to the positions between the light-emitting portions 36 in the first row. In other words, the multiple light-emitting portions 36 are also spaced apart in the column direction. The arrangement in FIG. 8B can be rephrased as, for example, a lattice arrangement, a staggered arrangement, or a checkered pattern.

As described above, the use of an apparatus including the organic light-emitting device according to the embodiment enables a stable display with good image quality even for a long time.

EXAMPLES

While the present disclosure will be described below by examples, the present disclosure is not limited these examples.

Example 1: Synthesis of Exemplified Compound C-1

Exemplified compound C-1 was synthesized according to the following scheme.

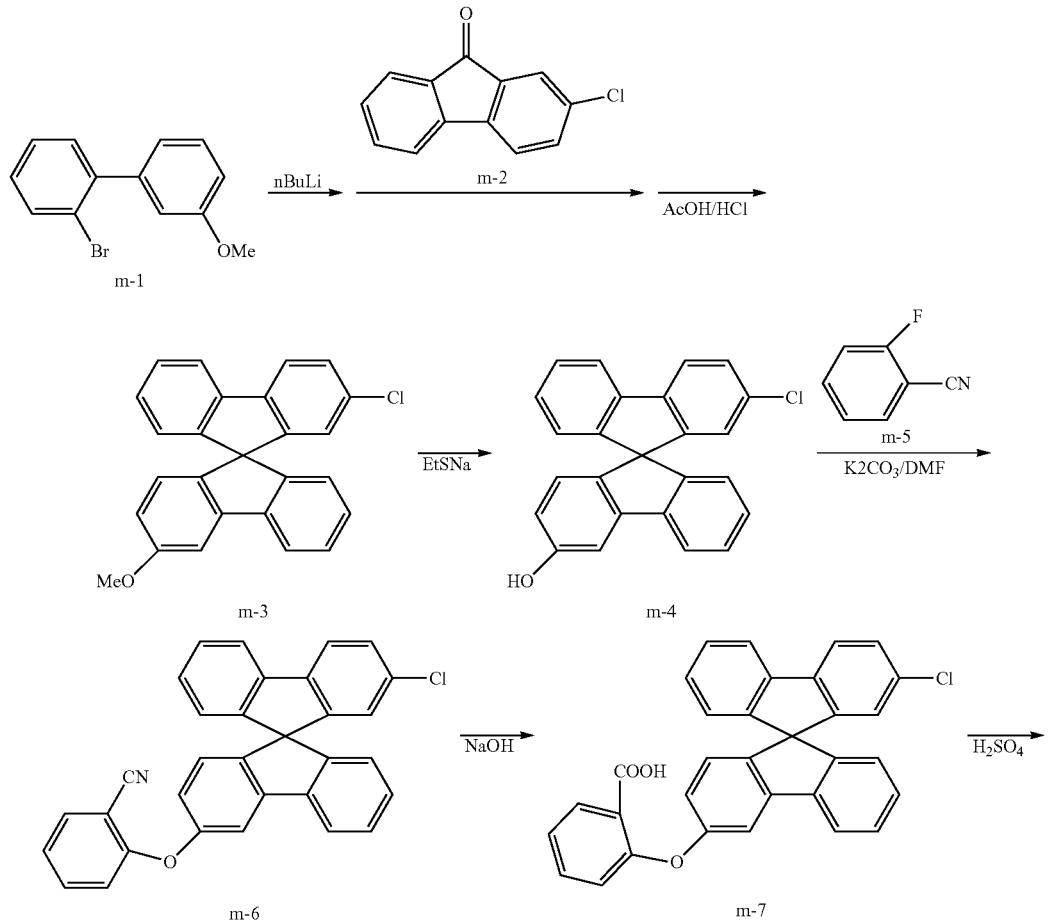

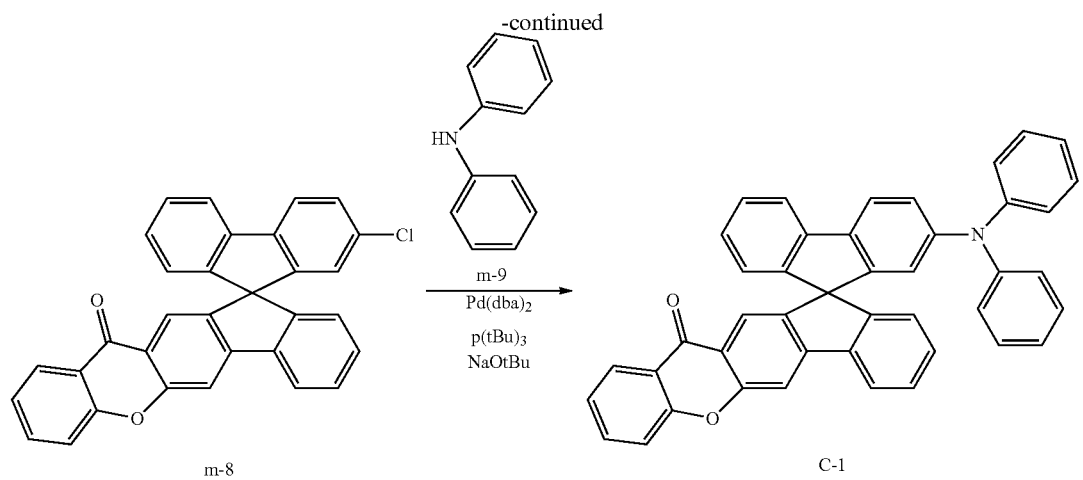

(1) Synthesis of Compound m-3

The following reagent and solvent were placed in a 500-mL recovery flask.
Compound m-1: 5.26 g (20.0 mmol)
THF: 150 mL The reaction solution was cooled to −78° C. under a stream of nitrogen, and then 35 mL (21.0 mmol) of n-BuLi (0.6 M) was added dropwise thereto. After the dropwise addition, the reaction solution was stirred at room temperature for 2 hours. The reaction solution was cooled to −78° C. again, and then 30 mL of a solution of 4.7 g (22.0 mmol) of compound m-2 in THF was added dropwise thereto. After the dropwise addition, the reaction solution was stirred at room temperature for 2 hours. The reaction solution was poured into ice water and extracted with toluene. The organic layer was concentrated to dryness to give a solid.

The solid was dissolved in 150 mL of acetic acid under a stream of nitrogen, and then 3 mL of concentrated hydrochloric acid was added dropwise thereto at room temperature. The reaction solution was stirred at room temperature for 5 hours. After the completion of the reaction, the reaction solution was poured into ice water, and the precipitated solid was filtered. The resulting solid was purified by silica gel column chromatography (toluene-ethyl acetate mixture) to give 4.6 g (yield: 62%) of m-3.

(2) Synthesis of Compound m-4

The following reagents and solvent were placed in a 300-mL recovery flask.
Compound m-3: 4.5 g (12.2 mmol)
Sodium ethanethiolate: 2.05 g (24.4 mmol)
DMF: 140 mL The reaction solution was heated and stirred at 60° C. for 24 hours under a stream of nitrogen. After the completion of the reaction, 100 mL of dilute hydrochloric acid was added, followed by filtration to give 4.5 g (yield: 96%) of m-4.

(3) Synthesis of Compound m-6

The following reagents and solvent were placed in a 200-mL recovery flask.
Compound m-4: 4.5 g (11.7 mmol)
Compound m-5: 1.6 g (12.9 mmol)
Potassium carbonate: 4.8 g (35.1 mmol)
DMF: 90 mL The reaction solution was heated and stirred at 100° C. for 24 hours under a stream of nitrogen. After the completion of the reaction, 100 mL of water was added, and then the mixture was filtered. The resulting solid was purified by silica gel column chromatography (toluene-ethyl acetate mixture) to give 3.4 g (yield: 63%) of m-6.

(4) Synthesis of Compound m-7

The following reagents and solvents were placed in a 200-mL recovery flask.
Compound m-6: 3.4 g (7.26 mmol)
Sodium hydroxide: 2.1 g (52.4 mmol)
Ethanol: 35 mL
Water: 35 mL The reaction solution was heated to reflux for 7 hours with stirring under a stream of nitrogen. After the completion of the reaction, 100 mL of water was added. The mixture was extracted with ethyl acetate, and then the organic layer was concentrated to dryness. The resulting solid was dispersed and washed with toluene to give 2.7 g of m-7 (yield: 75%).

(5) Synthesis of Compound m-8

The following reagent and solvent were placed in a 200-mL recovery flask.
Compound m-7: 2.7 g (5.45 mmol)
Sulfuric acid: 30 mL The reaction solution was stirred at 100° C. for 7 hours under a stream of nitrogen. After the completion of the reaction, the reaction solution was poured into ice water and filtered. The resulting solid was purified by silica gel column chromatography (chlorobenzene-ethyl acetate mixture) to give 1.2 g (yield: 45%) of m-8.

(6) Synthesis of Compound C-1

The following reagents and solvent were placed in a 500-mL recovery flask.
Compound m-8: 1.2 g (2.45 mmol)
Compound m-9: 0.497 g (2.94 mmol)
Sodium tert-butoxide: 0.47 g (4.90 mmol)
Pd(dba)$_2$: 70 mg
Tri-tert-butylphosphine: 74 mg
o-Xylene: 30 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 1.1 g (yield: 73%) of yellow solid C-1.

Exemplified compound C-1 was subjected to mass spectrometry with MALDI-TOF-MS (Bruker Autoflex LRF).

[MALDI-TOF-MS]
Measured value: m/z=601, calculated value: $C_{44}H_{27}NO_2$=601

Examples 2 to 11: Syntheses of Exemplified Compounds

As presented in Table 2, exemplified compounds of Examples 2 to 11 were each synthesized as in Example 1, except that raw material m-1 in Example 1 was changed to raw material 1, raw material m-2 was changed to raw material 2, raw material m-5 was changed to raw material 3, and raw material m-9 was changed to raw material 4. The resulting exemplified compounds were subjected to mass spectrometry as in Example 1. The measured values (m/z) are presented below.

TABLE 2

| Example | Exemplified compound | Raw material 1 | Raw material 2 |
|---|---|---|---|
| 2 | C-2 | 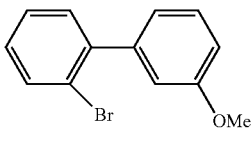 [SMILES: COc1cccc(-c2ccccc2Br)c1] | 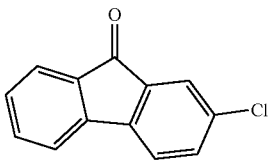 [SMILES: O=C1c2ccccc2-c2ccc(Cl)cc21] |
| 3 | C-3 | 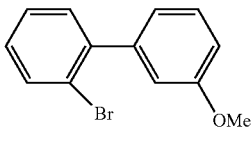 [SMILES: COc1cccc(-c2ccccc2Br)c1] | 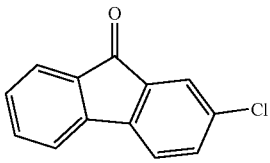 [SMILES: O=C1c2ccccc2-c2ccc(Cl)cc21] |
| 4 | C-5 | 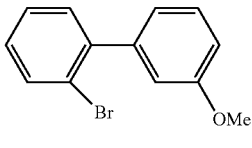 [SMILES: COc1cccc(-c2ccccc2Br)c1] | 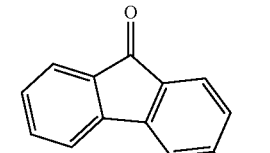 |
| 5 | C-8 | 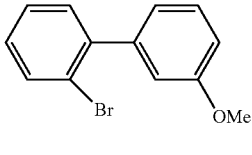 | 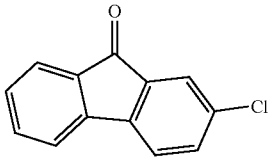 |
| 6 | C-9 | 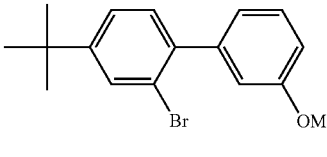 | 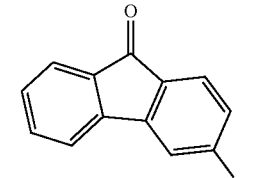 |
| 7 | C-13 | 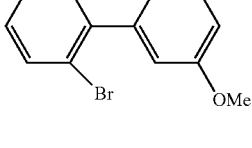 | 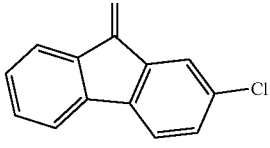 |
| 8 | C-15 | 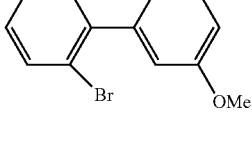 | 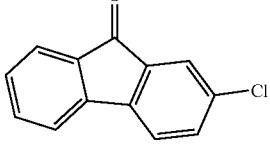 |

TABLE 2-continued
| | | Raw material 1 | Raw material 2 |
|---|---|---|---|
| 9 | D-1 | 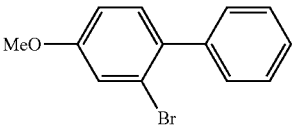 | 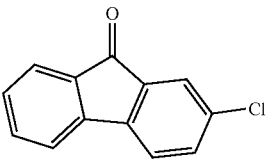 |
| 10 | D-3 | 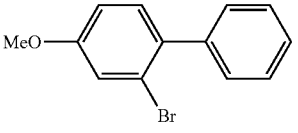 [SMILES: COc1ccc(-c2ccccc2)c(Br)c1] | 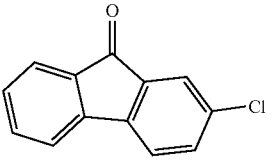 |
| 11 | D-6 | 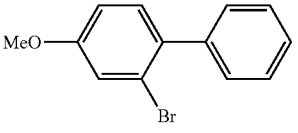 [SMILES: COc1ccc(-c2ccccc2)c(Br)c1] | 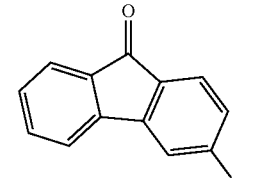 |
| Example | Raw material 3 | Raw material 4 | m/z |
|---|---|---|---|
| 2 | 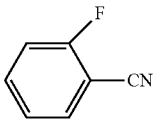 | 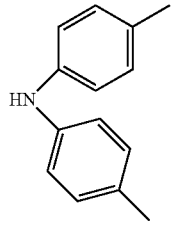 | 629 |
| 3 | 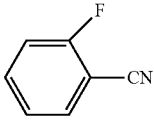 | 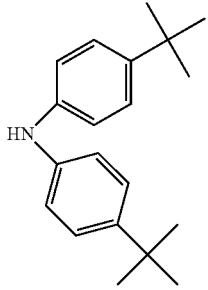 [SMILES: CC(C)(C)c1ccc(Nc2ccc(C(C)(C)C)cc2)cc1] | 713 |
| 4 | 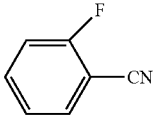 | 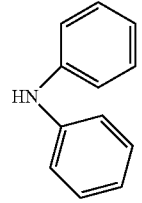 | 601 |
| 5 | 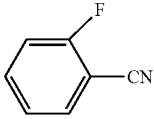 | 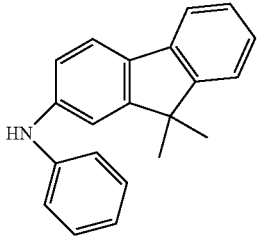 [SMILES: CC1(C)c2ccccc2-c2ccc(Nc3ccccc3)cc21] | 717 |

TABLE 2-continued
| | | | |
|---|---|---|---|
| 6 | 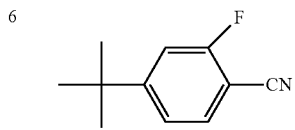 | 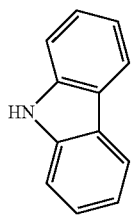 | 711 |
| 7 | 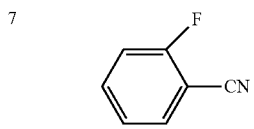 | 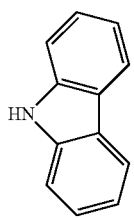 | 706 |
| 8 | 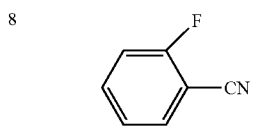 | 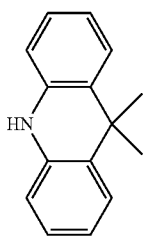 [SMILES: CC1(C)c2ccccc2Nc2ccccc21] | 678 |
| 9 | 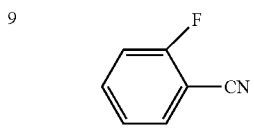 | 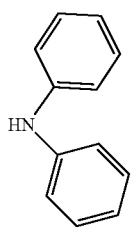 | 601 |
| 10 | 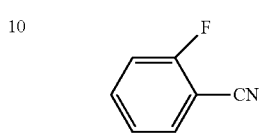 | 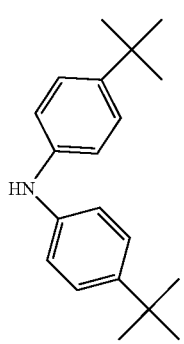 [SMILES: CC(C)(C)c1ccc(Nc2ccc(C(C)(C)C)cc2)cc1] | 713 |
| 11 | 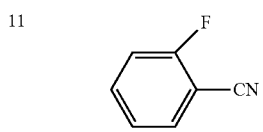 | 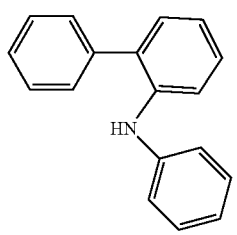 [SMILES: c1ccc(Nc2ccccc2-c2ccccc2)cc1] | 677 |

Example 12: Synthesis of Exemplified Compound F-1

Exemplified compound F-1 was synthesized according to the following scheme.

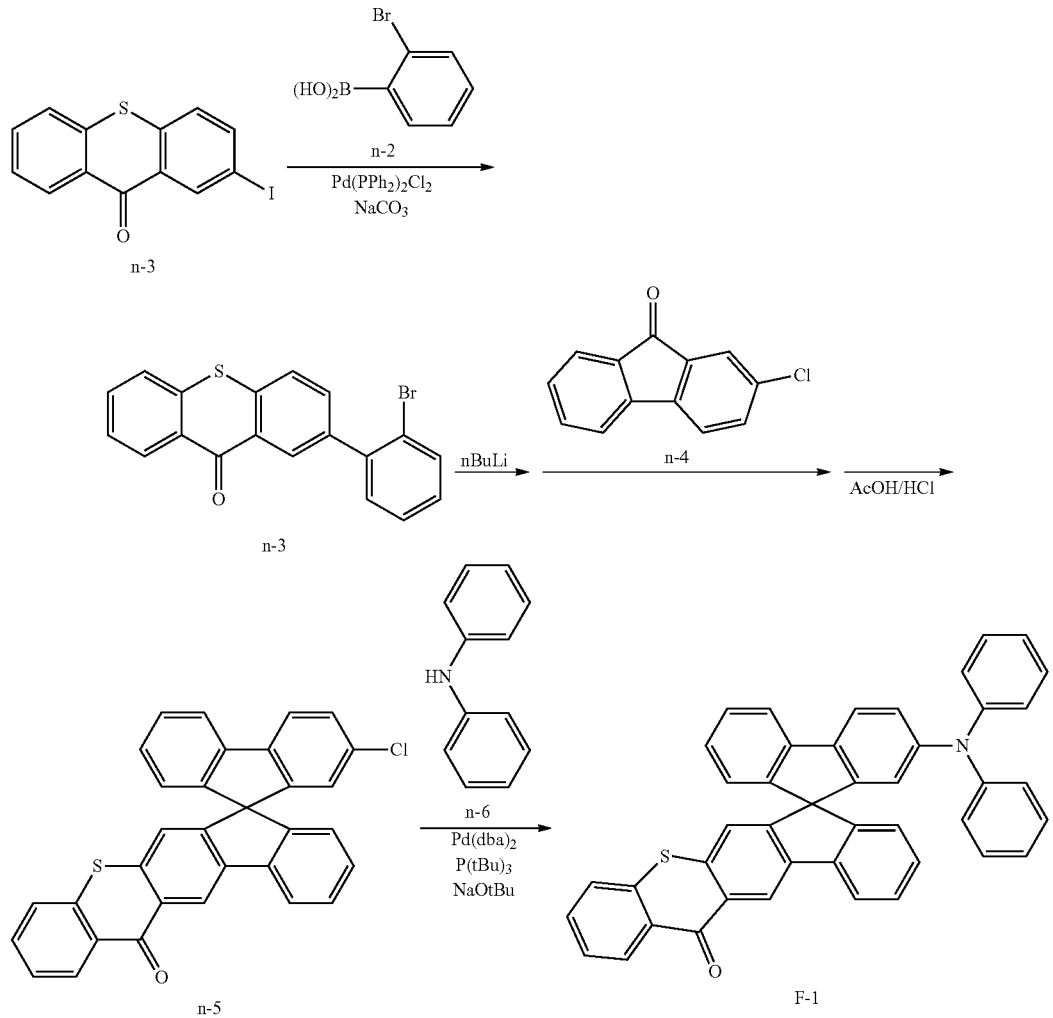

(1) Synthesis of Compound n-3

The following reagents and solvents were placed in a 200-mL recovery flask.

Compound n-1: 3.4 g (10.0 mmol)
Compound n-2: 2.2 g (11.0 mmol)
Sodium carbonate: 5.3 g (50.0 mmol)
Pd(PPh$_3$)$_2$Cl$_2$: 35 mg
Toluene: 35 mL
Water: 35 mL
Ethanol: 10 mL The reaction solution was heated and stirred at 60° C. for 5 hours. After the completion of the reaction, filtration was performed through Celite, and then the filtrate was concentrated to dryness. The resulting solid was purified by silica gel column chromatography (toluene-ethyl acetate mixture) to give 1.6 g (yield: 43%) of a yellow solid.

(2) Synthesis of Compound n-5

The following reagent and solvent were placed in a 200-mL recovery flask.

Compound n-3: 1.6 g (4.30 mmol)
THF: 80 mL

The reaction solution was cooled to −78° C. under a stream of nitrogen, and then 8.3 mL (5.00 mmol) of n-BuLi (0.6 M) was added dropwise thereto. After the dropwise addition, the reaction solution was stirred at room temperature for 2 hours. The reaction solution was cooled to −78° C. again, and then 10 mL of a solution of 1.8 g (8.60 mmol) of compound n-4 in THF was added dropwise thereto. After the dropwise addition, the reaction solution was stirred at room temperature for 2 hours. After the reaction, the reaction solution was poured into ice water and then extracted with toluene. The organic layer was concentrated to dryness to give a solid.

The resulting solid was dissolved in 80 mL of acetic acid under a stream of nitrogen, and then 1.5 mL of concentrated hydrochloric acid was added dropwise thereto at room temperature. The reaction solution was stirred at room temperature for 5 hours. After the completion of the reaction, the reaction solution was poured into ice water, and the precipitated solid was filtered. The resulting solid was purified by silica gel column chromatography (toluene-ethyl acetate mixture) to give 1.4 g (yield: 65%) of n-5.

(3) Synthesis of Compound F-1

The following reagents and solvent were placed in a 200-mL recovery flask.
Compound n-5: 1.3 g (2.69 mmol)
Compound n-6: 0.499 g (2.95 mmol)
Sodium tert-butoxide: 0.47 g (4.90 mmol)
Pd(dba)$_2$: 75 mg
Tri-tert-butylphosphine: 82 mg
o-Xylene: 30 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 1.1 g (yield: 68%) of yellow solid F-1.

Exemplified compound F-1 was subjected to mass spectrometry as in Example 1.

[MALDI-TOF-MS]

Measured value: m/z=617, calculated value: $C_{44}H_{27}NSO=617$

Examples 13 to 19: Synthesis of Exemplified Compound

As presented in Table 3, exemplified compounds of Examples 13 to 19 were each synthesized as in Example 12, except that raw material n-1 in Example 1 was changed to raw material 1, raw material n-2 was changed to raw material 2, raw material n-4 was changed to raw material 3, and raw material n-6 was changed to raw material 4. The resulting exemplified compounds were subjected to mass spectrometry as in Example 12. The measured values (m/z) are presented below.

TABLE 3

| Example | Exemplified compound | Raw material 1 | Raw material 2 |
|---|---|---|---|
| 13 | E-1 | 3-iodo-thioxanthone | 2-bromophenylboronic acid |
| 14 | E-6 | 2-iodo-thioxanthone | 2-bromophenylboronic acid |
| 15 | F-3 | 2-iodo-thioxanthone (isomer) | 2-bromophenylboronic acid |
| 16 | F-14 | 2-iodo-thioxanthone (isomer) | 2-bromophenylboronic acid |
| 17 | H-7 | 2-iodo-10,10-dimethylanthracen-9(10H)-one | 2-bromophenylboronic acid |
| 18 | H-14 | 2-iodo-10,10-dimethylanthracen-9(10H)-one (isomer) | 2-bromophenylboronic acid |

TABLE 3-continued
| | | | |
|---|---|---|---|
| 19 | F-12 | 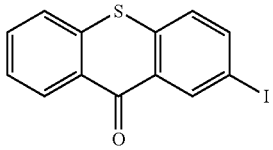 [SMILES: O=c1c2ccccc2sc2ccc(I)cc12] | 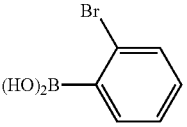 |
| Example | Raw material 3 | Raw material 4 | m/z |
|---|---|---|---|
| 13 | 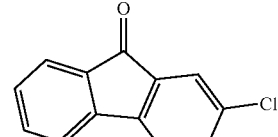 | 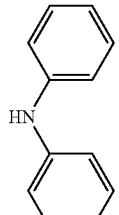 | 617 |
| 14 | 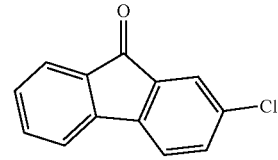 [SMILES: O=C1c2ccccc2-c2ccc(Cl)cc21] | 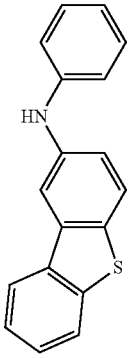 [SMILES: c1ccc(Nc2ccc3sc4ccccc4c3c2)cc1] | 723 |
| 15 | 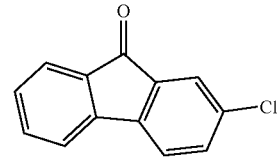 | 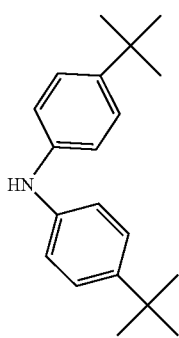 [SMILES: CC(C)(C)c1ccc(Nc2ccc(C(C)(C)C)cc2)cc1] | 729 |
| 16 | 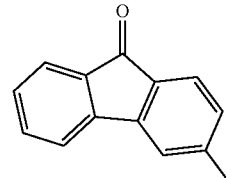 | 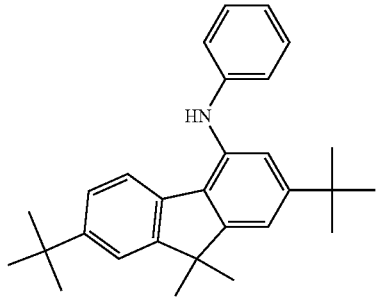 [SMILES: CC(C)(C)c1ccc2c(c1)C(C)(C)c1cc(C(C)(C)C)cc(Nc3ccccc3)c1-2] | 845 |

TABLE 3-continued

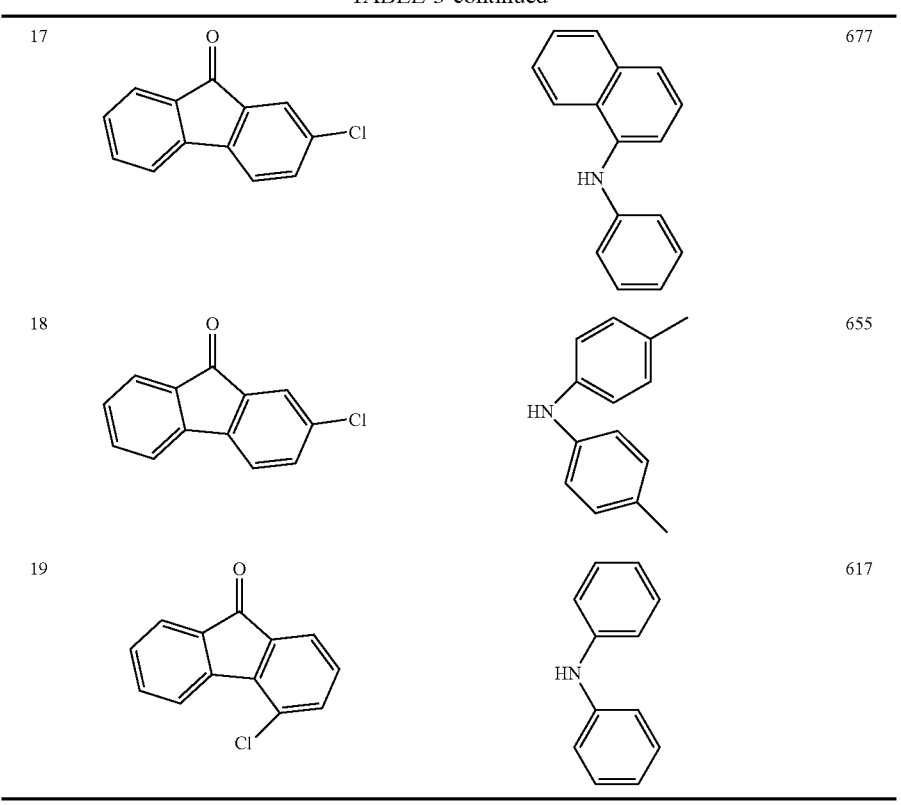

Example 20

In this Example, an organic light-emitting device having a bottom-emission structure was produced in which an anode, a hole injection layer, a hole transport layer, an electron blocking layer, a light-emitting layer, a hole-blocking layer, an electron transport layer, an electron injection layer, and a cathode were sequentially formed on a substrate.

An ITO film was formed on a glass substrate and subjected to desired patterning to form an ITO electrode (anode). The ITO electrode had a thickness of 100 nm. The substrate on which the ITO electrode had been formed in this way was used as an ITO substrate in the following steps. Next, vacuum evaporation was performed by resistance heating in a vacuum chamber to continuously form organic compound layers and electrode layers presented in Table 4 on the ITO substrate. Here, the opposite electrode (metal electrode layer, cathode) had an electrode area of 3 mm$^2$.

TABLE 4

| | Material | | Thickness (nm) |
|---|---|---|---|
| Cathode | Al | | 100 |
| Electron injection layer (EIL) | LiF | | 1 |
| Electron transport layer (ETL) | ET2 | | 15 |
| Hole-blocking layer (HBL) | ET11 | | 15 |
| Light-emitting layer (EML) | host EM11 88 | light-emitting material C-13 12 | 20 |
| Light-emitting layer, percentage (%) | | | |
| Electron-blocking layer (EBL) | HT12 | | 15 |

TABLE 4-continued

| | Material | Thickness (nm) |
|---|---|---|
| Hole transport layer (HTL) | HT3 | 30 |
| Hole injection layer (HIL) | HT16 | 5 |

The characteristics of the resulting device were measured and evaluated. As the initial characteristics associated with the light emission, green light emission with a maximum external quantum efficiency (E.Q.E.) of 5.8% was obtained. With regard to measurement instruments, specifically, the current-voltage characteristics were measured with a Hewlett-Packard 4140B microammeter, and the luminance was measured with a Topcon BM7. The device was subjected to a continuous operation test at a current density of 50 mA/cm$^2$. The time when the percentage of luminance degradation reached 5% (LT95) was measured to be 112 hours.

Examples 21 to 25

Organic light-emitting devices were produced in the same way as in Example 20, except that the compounds listed in Table 5 were used as appropriate. The characteristics of the resulting devices were measured and evaluated in the same way as in Example 20. Table 5 presents the measurement results.

TABLE 5

|  | HTL | EBL | Host | Light-emitting material | HBL | ETL | E.Q.E [%] | LT95 [h] | Emission color |
|---|---|---|---|---|---|---|---|---|---|
| Example 21 | HT3 | HT12 | EM11 | C-3 | ET12 | ET2 | 5.7 | 115 | green |
| Example 22 | HT3 | HT11 | EM10 | F-3 | ET12 | ET2 | 5.6 | 118 | green |
| Example 23 | HT3 | HT12 | EM9 | F-14 | ET12 | ET2 | 5.5 | 112 | green |
| Example 24 | HT2 | HT11 | EM14 | C-15 | ET12 | ET2 | 5.6 | 90 | green |
| Example 25 | HT2 | HT10 | EM32 | H-14 | ET12 | ET5 | 5.6 | 88 | green |

Example 26

An organic light-emitting device was produced in the same way as in Example 17, except that the organic compound layers and the electrode layer listed in Table 6 were continuously deposited.

TABLE 6

|  | Material | Thickness (nm) |
|---|---|---|
| Cathode | Al | 100 |
| Electron injection layer (EIL) | LiF | 1 |
| Electron transport layer (ETL) | ET2 | 15 |
| Hole-blocking layer (HBL) | ET11 | 15 |
| Light-emitting layer (EML) | host / assist material / light-emitting material | 20 |
|  | EM11 / C-3 / GD6 |  |
| Light-emitting layer, percentage (%) | 82 / 15 / 3 |  |
| Electron-blocking layer (EBL) | HT12 | 15 |
| Hole transport layer (HTL) | HT3 | 30 |
| Hole injection layer (HIL) | HT16 | 5 |

The characteristics of the resulting device were measured and evaluated in the same way as in Example 20. As the initial characteristics associated with the light emission, a green light emission with a maximum external quantum efficiency (E.Q.E.) of 6.8% was obtained. The device was subjected to a continuous operation test at a current density of 50 mA/cm². The time when the percentage of luminance degradation reached 5% (LT95) was measured to be 153 hours.

Examples 27 to 44 and Comparative Examples 1 and 2

Organic light-emitting devices were produced in the same way as in Example 26, except that the compounds listed in Table 7 were used as appropriate. The characteristics of the resulting devices were measured and evaluated in the same way as in Example 26. Table 7 presents the measurement results. The guest materials used in the comparative examples are illustrated below.

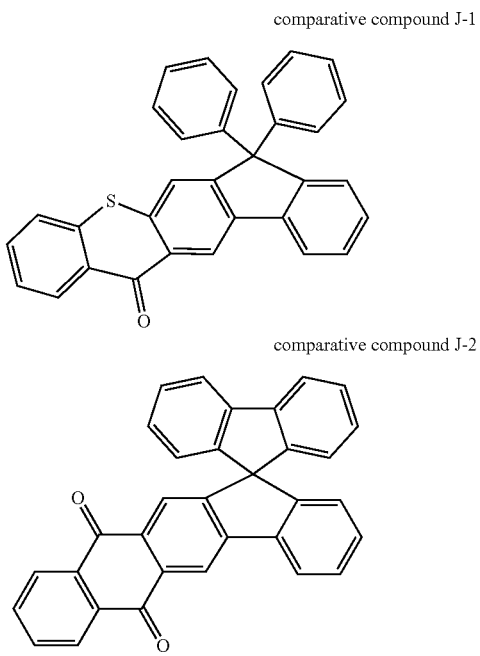

comparative compound J-1 comparative compound J-2

TABLE 7

|  | HTL | EBL | Host | Assist | Light-emitting material | HBL | ETL | E.Q.E [%] | LT95 [h] | Emission color |
|---|---|---|---|---|---|---|---|---|---|---|
| Example 27 | HT3 | HT12 | EM11 | C-2 | GD6 | ET12 | ET2 | 6.8 | 155 | green |
| Example 28 | HT3 | HT11 | EM11 | C-5 | GD6 | ET12 | ET2 | 6.7 | 159 | green |
| Example 29 | HT3 | HT12 | EM10 | C-13 | GD7 | ET12 | ET2 | 6.8 | 162 | green |
| Example 30 | HT2 | HT11 | EM9 | D-3 | GD7 | ET12 | ET2 | 6.7 | 158 | green |
| Example 31 | HT2 | HT10 | EM9 | C-3 | GD6 | ET12 | ET5 | 6.8 | 168 | green |
| Example 32 | HT3 | HT11 | EM14 | E-1 | GD9 | ET12 | ET2 | 7.2 | 132 | green |
| Example 33 | HT3 | HT12 | EM11 | F-3 | GD1 | ET11 | ET2 | 6.3 | 113 | green |
| Example 34 | HT3 | HT11 | EM14 | E-1 | GD1 | ET12 | ET2 | 6.4 | 102 | green |
| Example 35 | HT3 | HT12 | EM32 | F-3 | GD4 | ET11 | ET2 | 6.2 | 103 | green |

TABLE 7-continued

| | | | | EML | | | | | | |
| | HTL | EBL | Host | Assist | Light-emitting material | HBL | ETL | E.Q.E [%] | LT95 [h] | Emission color |
|---|---|---|---|---|---|---|---|---|---|---|
| Example 36 | HT2 | HT12 | EM11 | F-12 | GD6 | ET12 | ET2 | 5.8 | 156 | green |
| Example 37 | HT2 | HT12 | EM11 | C-2 | RD1 | ET12 | ET2 | 6.8 | 180 | red |
| Example 38 | HT3 | HT10 | EM9 | C-3 | RD1 | ET12 | ET2 | 6.8 | 185 | red |
| Example 39 | HT2 | HT12 | EM14 | D-3 | RD1 | ET11 | ET5 | 7.2 | 156 | red |
| Example 40 | HT3 | HT10 | EM32 | E-1 | RD1 | ET12 | ET2 | 7.2 | 154 | red |
| Example 41 | HT2 | HT12 | EM14 | F-3 | RD1 | ET11 | ET5 | 7.3 | 153 | red |
| Example 42 | HT3 | HT11 | EM11 | F-14 | RD2 | ET11 | ET2 | 6.3 | 125 | red |
| Example 43 | HT3 | HT12 | EM14 | H-14 | RD2 | ET12 | ET2 | 6.3 | 105 | red |
| Example 44 | HT3 | HT11 | EM32 | F-12 | RD2 | ET12 | ET2 | 5.7 | 175 | red |
| Comparative example 1 | HT3 | HT11 | EM14 | J-1 | GD9 | ET12 | ET2 | 3.8 | 38 | green |
| Comparative example 2 | HT3 | HT12 | EM14 | J-2 | RD1 | ET12 | ET2 | 3.9 | 35 | red |

Table 7 indicates that in each of Comparative examples 1 and 2, the maximum external quantum efficiency (E.Q.E.) was as low as 4.0 or less. The reason for this is that the large difference between S1 and T1 results in the absence of an emission component based on delayed fluorescence. Each of the devices containing the compounds according to embodiments of the present disclosure had a small difference between S1 and T1 because of the presence of carbonyl and amino groups, and exhibited high luminous efficiency owing to delayed fluorescence. In each of Comparative examples 1 and 2, the 5% degradation lifetime (LT95) was 50 hours or less, indicating poor durability characteristics. This is probably because the high degree of flatness at the center of the molecule results in molecular association. In contrast, in each of the devices containing the compounds according to embodiments of the present disclosure, the 5% degradation lifetime was 100 hours or more, indicating good durability characteristics. The good durability characteristics were provided by the presence of the spiro structure at the molecular center, which is less likely to cause concentration quenching.

The organic compound according to an embodiment of the present disclosure is less likely to cause molecular association, and thus concentration quenching can be reduced. Thus, when the organic compound according to an embodiment of the present disclosure is used in an organic light-emitting device, the organic light-emitting device having excellent luminous efficiency and driving durability characteristics can be provided.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-183751 filed Nov. 2, 2020, which is hereby incorporated by reference herein in its entirety.

What is claimed is:
1. An organic compound represented by formula [1] or [2]:

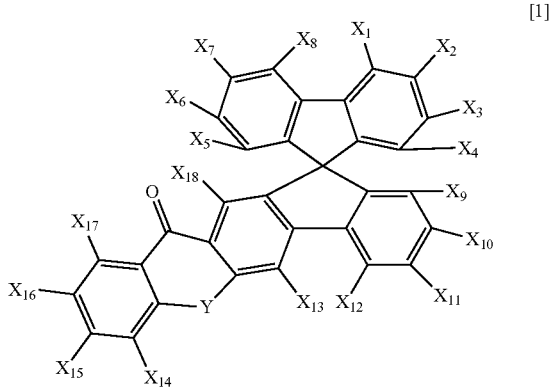

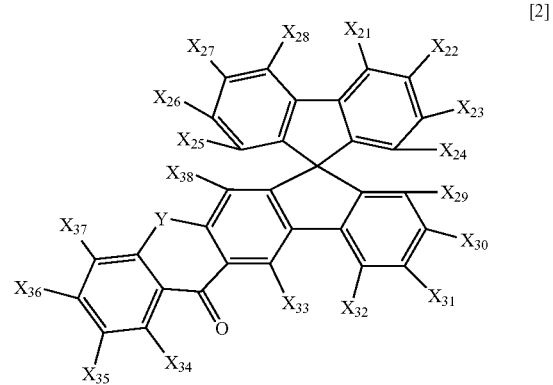

where in formula [1] or [2],
$X_1$ to $X_{18}$ and $X_{21}$ to $X_{38}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a substituted or unsubstituted heteroaryloxy group, a silyl group, and a cyano group, wherein at least one of $X_1$ to $X_8$ and at least one of $X_{21}$ to $X_{28}$ are substituted or unsubstituted amino groups, groups bonded to nitrogen atoms of the substituted or unsubstituted amino groups are optionally taken together to form a ring structure, the groups bonded to the nitrogen atoms of the substituted or unsubstituted amino groups are each optionally taken together with any of adjacent $X_1$ to $X_8$ or any of adjacent $X_{21}$ to $X_{28}$ to form a ring, and the groups bonded to the nitrogen atoms of the substituted or unsubstituted amino groups are each optionally taken together with any of adjacent $X_1$ to $X_8$ or any of adjacent $X_{21}$ to $X_{28}$ with oxygen or sulfur provided therebetween to form a ring; and each Y is oxygen, sulfur, selenium, tellurium, or a $CR_1CR_2$ group and are optionally the same or different, wherein $R_1$ and $R_2$ are each independently selected from a hydrogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a substituted or unsubstituted heteroaryloxy group, a silyl group, and a cyano group.

2. The organic compound according to claim 1, wherein at least one of $X_2$, $X_3$, $X_6$, and $X_7$ and at least one of $X_{22}$, $X_{23}$, $X_{26}$, and $X_{27}$ are each a substituted or unsubstituted amino group.

3. The organic compound according to claim 1, wherein at least one of $X_1$, $X_4$, $X_5$, and $X_8$ and at least one of $X_{21}$, $X_{24}$, $X_{25}$, and $X_{28}$ are each a substituted or unsubstituted amino group.

4. The organic compound according to claim 1, wherein each Y is oxygen.

5. An organic light-emitting device, comprising:
an anode;
a cathode; and
at least one organic compound layer disposed between the anode and the cathode,
wherein at least one layer of the at least one organic compound layer contains the organic compound according to claim 1.

6. The organic light-emitting device according to claim 5, wherein the layer containing the organic compound is a light-emitting layer.

7. The organic light-emitting device according to claim 6, wherein the light-emitting layer further contains a host material.

8. The organic light-emitting device according to claim 7, wherein the host material is a hydrocarbon compound.

9. The organic light-emitting device according to claim 7, wherein the light-emitting layer further contains a light-emitting material.

10. The organic light-emitting device according to claim 9, wherein the light-emitting material is a hydrocarbon compound.

11. The organic light-emitting device according to claim 6, wherein the light-emitting layer emits green light or red light.

12. A display apparatus, comprising:
multiple pixels,
at least one of the multiple pixels including:
the organic light-emitting device according to claim 5; and
a transistor connected to the organic light-emitting device.

13. A photoelectric conversion apparatus, comprising:
an optical unit including multiple lenses;
an image pickup device that receives light passing through the optical unit; and
a display unit that displays an image captured by the image pickup device,
wherein the display unit includes the organic light-emitting device according to claim 5.

14. An electronic apparatus, comprising:
a display unit including the organic light-emitting device according to claim 5;
a housing provided with the display unit; and
a communication unit being disposed in the housing and communicating with an outside.

15. A lighting device, comprising:
a light source including the organic light-emitting device according to claim 5; and
a light diffusion unit or an optical filter that transmits light emitted from the light source.

16. A moving object, comprising:
a lighting unit including the organic light-emitting device according to claim 5; and
a body provided with the lighting unit.

17. An exposure light source for an electrophotographic image-forming apparatus, comprising:
the organic light-emitting device according to claim 5.

* * * * *